US011352387B2

(12) United States Patent
Griffith et al.

(10) Patent No.: US 11,352,387 B2
(45) Date of Patent: *Jun. 7, 2022

(54) 2' AND/OR 5' AMINO-ACID ESTER PHOSPHORAMIDATE 3'-DEOXY ADENOSINE DERIVATIVES AS ANTI-CANCER COMPOUNDS

(71) Applicant: NuCana plc, Edinburgh (GB)

(72) Inventors: Hugh Griffith, Edinburgh (GB); Christopher McGuigan, Cardiff (GB); Valentina Ferrari, Cardiff (GB); Michaela Serpi, Cardiff (GB); Carmen Jimenez Antunez, Cardiff (GB)

(73) Assignee: NuCana plc, Edinburgh (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/782,952

(22) Filed: Feb. 5, 2020

(65) Prior Publication Data

US 2020/0181189 A1    Jun. 11, 2020

Related U.S. Application Data

(63) Continuation of application No. 15/518,527, filed as application No. PCT/GB2015/053628 on Nov. 27, 2015, now Pat. No. 10,570,168.

(30) Foreign Application Priority Data

Nov. 28, 2014 (GB) .................................. 1421211
Nov. 2, 2015 (GB) .................................. 1519316

(51) Int. Cl.
*C07H 19/20* (2006.01)
*C07H 19/173* (2006.01)

(52) U.S. Cl.
CPC ........... *C07H 19/20* (2013.01); *C07H 19/173* (2013.01)

(58) Field of Classification Search
CPC ........ C07H 19/20; C07H 19/173; A61P 31/12
See application file for complete search history.

(56) References Cited

U.S. PATENT DOCUMENTS

| | | | |
|---|---|---|---|
| 4,357,324 A | 11/1982 | Montgomery et al. | |
| 7,951,787 B2 | 5/2011 | McGuigan | |
| 8,263,575 B2 | 9/2012 | McGuigan et al. | |
| 8,658,616 B2 | 2/2014 | McGuigan et al. | |
| 8,759,318 B2 | 6/2014 | Chamberlain et al. | |
| 8,871,737 B2 | 10/2014 | Smith et al. | |
| 8,933,053 B2 | 1/2015 | McGuigan et al. | |
| 9,090,642 B2 | 7/2015 | Cho et al. | |
| 9,221,866 B2 | 12/2015 | McGuigan et al. | |
| 9,321,798 B2 | 4/2016 | McGuigan | |
| 9,655,915 B2 | 5/2017 | McGuigan et al. | |
| 10,022,390 B2 | 7/2018 | McGuigan et al. | |
| 10,149,859 B2 | 12/2018 | Liotta et al. | |
| 10,570,168 B2 * | 2/2020 | Griffith | C07H 19/16 |
| 2009/0306007 A1 | 12/2009 | Wagner | |
| 2012/0052046 A1 | 3/2012 | Chamberlain et al. | |
| 2012/0070411 A1 * | 3/2012 | Beigelman | C07H 19/067 424/85.4 |
| 2017/0095498 A1 | 4/2017 | Griffith et al. | |
| 2018/0289733 A1 | 10/2018 | Griffith et al. | |
| 2018/0369266 A1 | 12/2018 | Kennovin et al. | |
| 2019/0022118 A1 | 1/2019 | Griffith et al. | |
| 2019/0201432 A1 | 7/2019 | McGuigan et al. | |
| 2020/0181189 A1 | 6/2020 | Griffith et al. | |
| 2020/0181190 A1 | 6/2020 | Dammalapati et al. | |

FOREIGN PATENT DOCUMENTS

| | | |
|---|---|---|
| CN | 105646629 A | 6/2016 |
| WO | WO-2005/012327 A2 | 2/2005 |
| WO | WO-2006/063149 A1 | 6/2006 |
| WO | 2006/100439 A1 | 9/2006 |
| WO | WO-2006/100439 A1 | 9/2006 |
| WO | WO-2010091386 A2 | 8/2010 |
| WO | WO-2010108140 A1 | 9/2010 |
| WO | WO-2012/040126 A1 | 3/2012 |
| WO | WO-2012040127 A1 | 3/2012 |
| WO | WO-2012/045999 A1 | 4/2012 |
| WO | WO-2012/117246 A1 | 9/2012 |
| WO | WO-2013070887 A1 | 5/2013 |
| WO | WO-2015/038596 A1 | 3/2015 |
| WO | WO-2015/081133 A2 | 6/2015 |
| WO | WO-2015/198059 A1 | 12/2015 |
| WO | WO-2016/083830 A1 | 6/2016 |
| WO | 2016/145142 A1 | 9/2016 |

(Continued)

OTHER PUBLICATIONS

U.S. Appl. No. 15/279,611.
U.S. Appl. No. 16/305,153.
U.S. Appl. No. 16/305,159.
U.S. Appl. No. 16/305,162.
Birkus et al., "Cathepsin A Is the Major Hydrolase Catalyzing the Intracellular Hydrolysis of the Antiretroviral Nucleotide Phosphonoamidate Prodrugs GS-7340 and GS-9130," Antimicrob Agents Chemother 51(2):543-550 (2004).
Cahard et al, "Ary Ioxy Phosphoramidate Triesters as Pro-Tides" Mini-Reviews in Medicinal Chemistry 4:371-382 (2004).
Derudas et al.,"The Application of Phosphoramidate Protide Technology to Acyclovir Confers Anti-HIV Inhibition," J Med Chem 52:5520-553 (2009).
Galmarini et al., "Nucleoside analogues and nucleobases in cancer treatment," Lancet Oncol 3:415-24 (2002).

(Continued)

*Primary Examiner* — Pancham Bakshi
(74) *Attorney, Agent, or Firm* — Knowles Intellectual Property Strategies, LLC

(57) ABSTRACT

Disclosed are chemical compounds, the compounds for use in a method of treatment, particularly in a method of prophylaxis or treatment for cancer, a process for preparation of the compounds and pharmaceutical compositions comprising the compounds. The compounds may, in particular, be useful in the treatment of leukaemia, lymphoma and/or solid tumours in *Homo sapiens*. The compounds are derivatives of cordycepin (3'-deoxyadenosine) having a 2' and/or 5'-amino-acid ester phosphoramidate moiety.

19 Claims, 5 Drawing Sheets

(56) References Cited

FOREIGN PATENT DOCUMENTS

| WO | WO-2016/181093 | A1 | 11/2016 |
|---|---|---|---|
| WO | WO-2017/109491 | A1 | 6/2017 |
| WO | WO-2017/207986 | A1 | 12/2017 |
| WO | WO-2017/207989 | A1 | 12/2017 |
| WO | WO-2017/207993 | A1 | 12/2017 |
| WO | WO 2018/229493 | A2 | 12/2018 |

OTHER PUBLICATIONS

Glazer et al., "Potentiation by 2'-deoxycoformycin of the inhibitory effect by 3'-deoxyadenosine (cordycepin) on nuclear RNA synthesis in L1210 cells in vitro," Cancer Res, 38(8): 2233-2238 (1978).
Grem et al., "5-Fluorouracil: forty-plus and still ticking. A review of its preclinical and clinical development," Invest New Drugs 18:299-313 (2000).
Griffith et al., "Enhanced Inhibition of the EDHF Phenomenon by a Phenyl Methoxyalaninyl Phosphoramidate Derivative of Dideoxyadenosine," Brit J Pharmacol, 142(1):27-30 (2004).
International Search Report and Written Opinion for International Application No. PCT/GB2015/053628 dated Apr. 1, 2016.
Jones et al., "Synthesis and anti-HIV activity of some novel phosphorodiamidate derivatives of 3'-azido-3'-deoxvthvmidine (AZT)," Antivir Chem Chemother 2(1):35-39 (1991).
Lee et al., "Selective Intracellular Activation of a Novel Prodrug of the Human Immunodeficiency Virus Reverse Transcriptase Inhibitor Tenofovir Leads to Preferential Distribution and Accumulation in Lymphatic Tissue," Antimicrob Agents Chemother. 49(5):1898-1906 (2005).
McGuigan et al, "Application of Phosphoramidate Pronucleotide Technology to Abacavir Leads to a Significant Enhancement of Antiviral Potency," J Med Chem 48:3504-3515 (2005).
McGuigan et al., "Anti-cancer ProTides: tuning the activity of BVDU phosphoramidates related to thymectacin," Bioorg Med Chem 13:3219-3227 (2005).
McGuigan et al., "Design, synthesis and evaluation of a novel double pro-drug: INX-08189. A new clinical candidate for hepatitis C virus," Bioorg Med Chem Lett 20:4850-4854 (2010).
McGuigan et al., "Phosphoramidate ProTides of the Anticancer Agent FUDR Successfully Deliver the Preformed Bioactive Monophosphate in Cells and Confer Advantage over the Parent Nucleoside," J Med Chem 54(20):7247-7258 (2011).
Mehellou et al., "Aryloxy phosphoramidate triesters: a technology for delivering mono-phosphorylated nucleosides and sugars into cells," Chem Med Chem 4(11):1779-1791 (2009).
Mehellou et al., "Phosphoramidates of 2'ß-d-arabinouridine (AraU) as phosphate prodrugs: design, synthesis, in vitro activity and metabolism," Bioorg Med Chem 18:2439-2446 (2010).
Robak, "New nucleoside analogs for patients with hematological malignancies," Expert Opinion Investig Drugs, 20(3):343-359 (2011).
Wagner et al., "Pronucleotides: Toward the In Vivo Delivery of Antiviral and Anticancer Nucleotides," Med Res Rev 20(6):417-451 (2000).
Chopra et al., "Plant tumour biocontrol agent employs a tRNA-dependent mechanism to inhibit leucyl-tRNA synthetase," Nature Communications, 4:1417 (2013).
Filippov et al., "Synthesis of the antibiotically active part of agrocin 84," Tetrahedron Letters, 39:4891-4894 (1998).
Van de Vijver et al., "Antibacterial 5'-O-(N-dipeptidyl)-sulfamoyladenosines," Bioorganic & Medicinal Chemistry, 17: 260-269 (2009).
Vemula et al., "Solubility Enhancement Techniques," International Journal of Pharmaceutical Sciences Review and Research, 5(1): 41-51 (2010).
Congiatu, Costantino; et al., "Design, Synthesis and Biological Evaluation of Some Novel Nucleotide Prodrugs as Potential Anticancer Agents," A Thesis submitted to the University of Wales for the Degree of Philosophiae Doctor, 2006; p. 1-290.
U.S. Publication No. 2020/0181190, A1, U.S. Appl. No. 16/623,272, Dammalapati, Issued Jun. 11, 2020
Aman et al., "From adenosine to 3'-deoxyadenosine: development and scale up," Org Proc Res Dev 4(6):601-605 (2000).
Bazin et al.; "A convenient preparation of 3'-deoxyadenosine (Cordycepin) and 9-[3'(R)-Deuterio-β-D-2'(R)-pentofuranosyl]-adenine," Synthesis 12:1108-1111 (1985).
Kim, Sung Eun; et al.; "Deoxyribosyl analogues of nethionyl and isoleucyl sulfamate adenylates as inhibitors of methionyl-tRNA and isoleucyl-tRNA synethtases," Elsevier; Bioorganic & Medicinal Chemistry Letters 15 (2005) 3388-3393.
Nyilas, A., et al.; "The Cordycepin Analogue of 2,5A and Its Threo Isomer. Chemical Synthesis, Conformation and Biological Activity," Department of Bioorganic Chemistry, UK, Acta Chemica Scandinavica B00 (1986); pp. 68-688.
Nyilas, A'gnes and Jyoti Chattopadhyaya; "A Convenient Preparation of 9-(3'-Deoxy-β-D-threo-pentofuranosyl)-adenine and 9-[3'Deoxy-3'-(S)-deuterio-βD-2'-(s)-pentofuranosyl]-adenine," Synthesis, Department of Bioorganic Chemistry, Biomedical Center, Box 581, Uppsala University, S-751 23 Uppsala, Sweden, 1986; pp. 196-198.
Ross et al., "Synthesis of Diastereomerically Pure Nucleotide Phosphoramidates," Journal of Organic Chemistry, 76:8311-8319 (2011).

\* cited by examiner

2' AND/OR 5' AMINO-ACID ESTER PHOSPHORAMIDATE 3'-DEOXY ADENOSINE DERIVATIVES AS ANTI-CANCER COMPOUNDS

RELATED APPLICATIONS

This application is a Continuation of application Ser. No. 15/518,527, filed on Apr. 12, 2017; which is a § 371 national stage application based on PCT/GB2015/053628, filed Nov. 27, 2015; which claims the benefit of priority to GB 1421211.2, filed Nov. 28, 2014; and GB 1519316.2, filed on Nov. 2, 2015.

The present invention relates to chemical compounds, the compounds for use in a method of treatment, particularly in a method of prophylaxis or treatment for cancer, a process for preparation of the compounds and pharmaceutical compositions comprising the compounds.

Particularly, although not exclusively, the present invention relates to chemical compounds for use in the treatment of leukaemia, lymphoma and/or solid tumours in *Homo sapiens*.

Cordycepin is 3'-deoxyadenosine (3'dA). It is a nucleoside analogue of adenosine that lacks the 3'-hydroxyl group on the ribose moiety.

Cordycepin is one of the major bioactive substances produced by *Cordyceps militaris*, a parasitic fungus used for traditional Chinese medicine because of its immune activator, anti-aging and anti-tumour effects. Reference is made to Tuli, H. S. et al 3 Biotech (2014) 4:1-12.

Cordycepin can be produced synthetically from adenosine. Reference for such synthetic procedures is made to Robins, J. R. et al J. Org. Chem. 1995, 60, 7902-7908 and Aman, S. et al Organic Process Research & Development 2000, 4, 601-605.

Cordycepin has been studied most extensively as an anti-cancer agent.

Because of its structure, 3'dA and its triphosphate form could potentially interfere with any process respectively requiring adenosine or adenosine triphosphate (ATP).

After administration, 3'dA is, however, quickly deaminated by adenosine deaminase (ADA), and rapidly metabolized to an inactive metabolite, 3'-deoxyinosine, in vivo. Reference is made to Tsai, Y-J et al J. Agri. Food Chem. 58 4638-43 (2010).

As described in Glazer, R. et al Cancer Research 38, 2233-2238 (1978), cordycepin has been shown to exhibit anti-cancer potency when used in combination with an inhibitor of adenosine deaminase, as pentostatine (2-deoxycoformicin, dCF). Other ADA inhibitors have also been proposed as alternative co-drugs to be administered with cordycepin, but it is the combination of 3'dA-dCF which has been employed in clinical trials. As acknowledged in Wehbe-Janek, H. et al Anticancer Research 27: 3143-3146 (2007), 2-deoxycoformicin is, however, known to be a relatively toxic drug.

2-Fluorocordycepin (3'deoxy-2-fluoroadenosine) is also known to be cytotoxic (see e.g. Montgomery et al., *J. Med. Chem.*, 1969, 12(3), 498-504 and Dickinson et al, J. Med. Chem., 1967, 10(6), 1165-1166).

2-Chlorocordycepin (3' deoxy-2-fluoroadenosine) has been assessed for it's antiviral activity (Rosowsky et al. *J. Med. Chem.*, 1989, 32, 1135-40).

The present invention has as its object a solution to the problem of enhancing the potency of a purine-based 3'-deoxynucleoside, as exemplified by cordycepin (3'-deoxyadenosine), in a method of prophylaxis or treatment, particularly, although not exclusively, in anti-cancer chemotherapy, including chemotherapy to treat leukaemia, lymphoma and/or solid tumours.

A further object of the present invention is to provide a solution to the problem of purine-based 3'-deoxynucleosides, as exemplified by cordycepin (3'-deoxyadenosine), on administration being deaminated by ADA and then rapidly metabolized to an inactive metabolite.

A further object of the present invention is to provide a solution to the problem of purine-based 3'-deoxynucleosides, as exemplified by cordycepin (3'-deoxyadenosine), on administration being deaminated by ADA and then rapidly metabolized to an inactive metabolite, so as to obviate entirely, or to reduce to at least some extent, the need to co-administer an ADA inhibitor when a purine-based 3'-deoxynucleoside is employed in a method of prophylaxis or treatment, particularly, although not exclusively, in anti-cancer chemotherapy, including chemotherapy to treat leukaemia, lymphoma and/or solid tumours.

According to a first aspect of the present invention there is provided a compound which is a compound of formula (Ia):

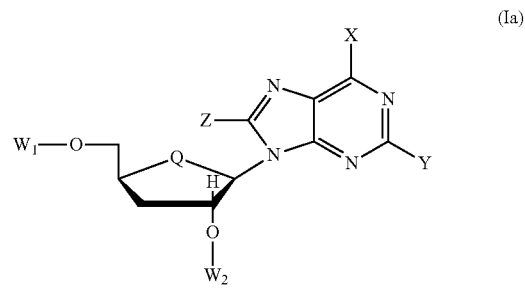

wherein:

$W_1$ and $W_2$ are each independently selected from the group consisting of —P(=O)(U)(V) and H, with the proviso that at least one of $W_1$ and $W_2$ is —P(=O)(U)(V), where U and V, independently for each of $W_1$ and $W_2$, are selected from the group consisting of:

(a) U is —OAr in combination with V is —NR$_4$—CR$_1$R$_2$—C(=O)OR$_3$, where Ar is selected from the group consisting of $C_{6-30}$aryl and $_{5-30}$heteroaryl, each of which is optionally substituted;

each of $R_1$ and $R_2$ is independently selected from H, and the group consisting of $C_{1-20}$alkyl, $C_{6-30}$aryl $C_{1-6}$alkyl, $C_{2-20}$alkenyl, $C_{1-20}$alkoxy, $C_{1-20}$alkoxy $C_{1-20}$alkyl, $C_{1-20}$alkoxy$C_{6-30}$alkyl, $C_{2-20}$alkynyl, $C_{3-20}$cycloalkyl$C_{6-30}$aryl, $C_{6-30}$aryloxy and $_{5-20}$heterocyclyl, any of which is optionally substituted;

$R_3$ is selected from H, and the group consisting of $C_{1-20}$alkyl, $C_{6-30}$aryl$C_{1-20}$alkyl, $C_{2-20}$alkenyl, $C_{1-20}$alkoxy$C_{1-20}$alkyl, $C_{1-20}$alkoxy$C_{6-30}$aryl, $C_{2-20}$alkynyl, $C_{3-20}$cycloalkyl$C_{6-30}$aryl, and $_{5-20}$heterocyclyl, any of which is optionally substituted;

$R_4$ is selected from H, and the group consisting of $C_{1-20}$alkyl, $C_{6-30}$aryl$C_{1-20}$alkyl, $C_{2-20}$alkenyl, $C_{1-20}$alkoxy, $C_{1-20}$alkoxy$C_{1-20}$alkyl, $C_{1-20}$alkoxy $C_{6-30}$alkyl, $C_{2-20}$alkynyl, $C_{3-20}$cycloalkyl$C_{6-30}$aryl, $C_{6-30}$aryloxy and $_{5-20}$heterocyclyl, any of which is optionally substituted;

and (b) each of U and V is selected independently from —$NR_5R_6$, where $R_5$ is selected from the group consisting of H and $C_{1-6}$alkyl and $R_6$ is —$CR_7R_8CO_2R_9$, where $R_7$ and $R_8$ are selected independently from the group consisting of the side chains, including H, of naturally occurring alpha amino acids and $R_9$ is selected from H, and the group consisting of $C_{1-20}$alkyl, $C_{6-30}$aryl$C_{1-20}$alkyl-, $C_{2-20}$alkenyl, $C_{1-20}$alkoxy $C_{1-20}$alkyl, $C_{1-20}$alkoxy$C_{6-30}$alkyl, $C_{2-20}$alkynyl, $C_{3-20}$cycloalkyl$C_{6-30}$ aryl, and $_{5-20}$heterocyclyl, any of which is optionally substituted; or $R_5$ and $R_6$ together with the N atom to which they are attached form a ring moiety comprising 5 to 8 ring atoms;

Q is selected from the group consisting of O, S and $CR_{10}R_{11}$, where $R_{10}$ and $R_{11}$ are independently selected from H, F and $C_{1-6}$alkyl;

each of X and Z is independently selected from the group consisting of H, OH, F, $C_1$, Br, I, $C_{1-6}$alkyl, —$NR_{12}R_{13}$ where each of $R_{12}$ and $R_{13}$ is independently selected from H and $C_{1-6}$alkyl, and —$SR_{14}$ where $R_{14}$ is selected from the group consisting of H and $C_{1-6}$alkyl; and Y is selected from the group consisting of H, OH, F, Cl, Br, I, —$OC_{1-6}$alkyl, $C_{1-6}$alkyl, $C_{2-8}$alkynyl, —$NR_{15}R_{16}$ where each of $R_{15}$ and $R_{16}$ is independently selected from H and $C_{1-6}$alkyl, and —$SR_{17}$ where $R_{17}$ is selected from the group consisting of H and $C_{1-6}$alkyl, or a pharmaceutically acceptable salt, ester, salt of an ester, solvate or prodrug of the compound of formula (Ia).

Compounds of the present invention are purine-based 3'-deoxynucleosides in which each of the 3' substituent positions on the sugar moiety of the nucleoside is occupied by H.

In a further embodiment, the compound of the invention may be a compound of formula (Ib):

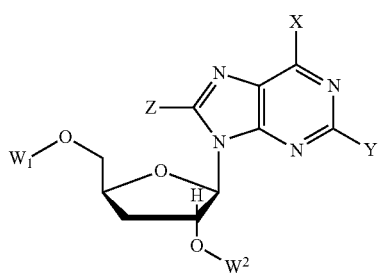

(Ib)

wherein:

$W_1$ and $W_2$ are each independently selected from the group consisting of —P(=O)(U)(V) and H, with the proviso that at least one of $W_1$ and $W_2$ is —P(=O)(U)(V), where U and V, independently for each of $W_1$ and $W_2$, are selected from the group consisting of:

(a) U is —OAr and V is —$NR_4$—$CR_1R_2$—C(=O) $OR_3$, where Ar is selected from the group consisting of $C_{6-30}$aryl and $_{5-30}$heteroaryl, each of which is optionally substituted;

each of $R_1$ and $R_2$ is independently selected from H, and the group consisting of $C_{1-20}$alkyl, $C_{6-30}$aryl $C_{1-6}$alkyl, $C_{2-20}$alkenyl, $C_{1-20}$alkoxy, $C_{1-20}$alkoxy $C_{1-20}$alkyl, $C_{1-20}$alkoxy$C_{6-30}$aryl, $C_{2-20}$alkynyl, $C_{3-20}$cycloalkyl, $C_{6-30}$aryl, $C_{6-30}$aryloxy and $_{5-20}$heterocyclyl, any of which is optionally substituted;

$R_3$ is selected from H, and the group consisting of $C_{1-20}$alkyl, $C_{6-30}$aryl$C_{1-20}$alkyl, $C_{2-20}$alkenyl, $C_{1-20}$alkoxy$C_{1-20}$alkyl, $C_{1-20}$alkoxy$C_{6-30}$aryl, $C_{2-20}$alkynyl, $C_{3-20}$cycloalkyl, $C_{6-30}$aryl, and $_{5-20}$heterocyclyl, any of which is optionally substituted;

$R_4$ is selected from H, and the group consisting of $C_{1-20}$alkyl, $C_{6-30}$aryl$C_{1-20}$alkyl, $C_{2-20}$alkenyl, $C_{1-20}$alkoxy, $C_{1-20}$alkoxy$C_{1-20}$alkyl, $C_{1-20}$alkoxy $C_{6-30}$aryl, $C_{2-20}$alkynyl, $C_{3-20}$cycloalkyl, $C_{6-30}$aryl, $C_{6-30}$aryloxy and $_{5-20}$heterocyclyl, any of which is optionally substituted;

and (b) each of U and V is selected independently from —$NR_5R_6$, where $R_5$ is selected from the group consisting of H and $C_{1-6}$alkyl and $R_6$ is —$CR_7R_8CO_2R_9$, where $R_7$ and $R_8$ are selected independently from the group consisting of the side chains, including H, of naturally occurring alpha amino acids and $R_9$ is selected from H, and the group consisting of $C_{1-20}$alkyl, $C_{6-30}$aryl$C_{1-20}$alkyl-, $C_{2-20}$alkenyl, $C_{1-20}$alkoxy $C_{1-20}$alkyl, $C_{1-20}$alkoxy$C_{6-30}$aryl, $C_{2-20}$alkynyl, $C_{3-20}$cycloalkyl, $C_{6-30}$aryl, and $_{5-20}$heterocyclyl, any of which is optionally substituted; or $R_5$ and $R_6$ together with the N atom to which they are attached form a ring moiety comprising 5 to 8 ring atoms;

X is selected from $NR^{12}R^{13}$ where each of $R_{12}$ and $R_{13}$ is independently selected from H and $C_{1-6}$alkyl; and —$SR_{14}$ where $R_{14}$ is selected from the group consisting of H and $C_{1-6}$alkyl;

Z is independently selected from the group consisting of H, OH, F, Cl, Br, I, $C_{1-6}$alkyl, —$NR_{12}R_{13}$, and —$SR_{14}$ where $R_{14}$ is selected from the group consisting of H and $C_{1-6}$alkyl; and Y is selected from the group consisting of H, OH, F, Cl, Br, I, —$OC_{1-6}$alkyl, $C_{1-6}$alkyl, $C_{2-8}$alkynyl, —$NR_{15}R_{16}$ where each of $R_{15}$ and $R_{16}$ is independently selected from H and $C_{1-6}$alkyl, and —$SR_{17}$ where $R_{17}$ is selected from the group consisting of H and $C_{1-6}$alkyl, or a pharmaceutically acceptable salt, ester, salt of an ester, solvate or prodrug of the compound of formula (Ib).

The compound of formula (Ib) may be a compound of formula (II):

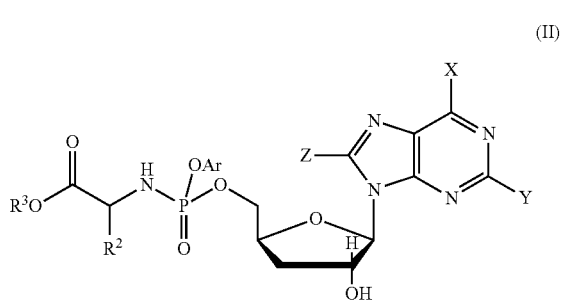

(II)

wherein Ar, Y, Z, $R^2$ and $R^3$ are as described above for formula (Ib) and wherein X is —$NR^{12}R^{13}$.

The compound of formula (Ib) may be a compound of formula (III):

(III)

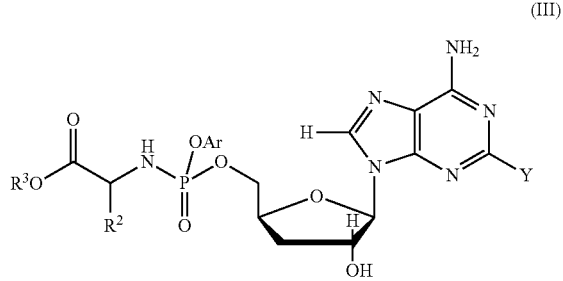

wherein Ar, $R^2$ and $R^3$ are as described above for formula (Ib) and wherein Y is selected from H, F, Cl and OMe.

The following statements apply to compounds of any of formulae (Ia), (Ib), (II) and (III). These statements are independent and interchangeable. In other words, any of the features described in any one of the following statements may (where chemically allowable) be combined with the features described in one or more other statements below. In particular, where a compound is exemplified or illustrated in this specification, any two or more of the statements below which describe a feature of that compound, expressed at any level of generality, may be combined so as to represent subject matter which is contemplated as forming part of the disclosure of this invention in this specification.

In the present specification, the term "naturally occurring alpha amino acid" means an amino acid, which can have L or D stereochemistry, selected from the group consisting of glycine, alanine, valine, leucine, isoleucine, phenylalanine, tyrosine, tryptophan, serine, threonine, lysine, arginine, histidine, aspartic acid, glutamic acid, asparagine, glutamine, cysteine and methionine.

In the present specification, a side chain of a naturally occurring alpha amino acids is thus a member selected from the group consisting of H, $CH_3$, —$CH(CH_3)_2$, —$CH_2CH(CH_3)_2$, —$CH(CH_3)(CH_2CH_3)$, —$CH_2Ph$, —$CH_2Ph$-OH, —$CH_2SH$, —$CH_2CH_2SCH_3$, —$CH_2OH$, —$(CH_3)(OH)$, —$CH_2CH_2CH_2CH_2NH_3^+$, —$CH_2CH_2CH_2NHC(=NH_2^+)NH_2$, —$CH_2C(O)O—$, —$CH_2CH_2C(O)O—$, —$CH_2C(O)NH_2$, —$CH_2CH_2C(O)NH_2$,

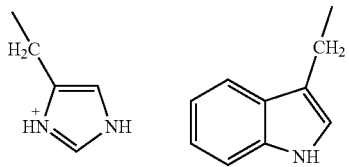

It may be that $W_1$ is —P(=O)(U)(V) and $W_2$ is H and the compound of the invention is a 5'-phosphoramidate of the parent 3'-deoxynucleoside. In certain preferred embodiments, $W_1$ is —P(=O)(U)(V), wherein U is —OAr and V is —$NR_4$—$CR_1R_2$—C(=O)$OR_3$, and $W_2$ is H.

It may be that $W_1$ is H and $W_2$ is —P(=O)(U)(V) and the compound of the invention is a 2'-phosphoramidate of the parent 3'-deoxynucleoside. In certain preferred embodiments, $W_1$ is H and $W_2$ is —P(=O)(U)(V), wherein U is —OAr and V is —$NR_4$—$CR_1R_2$—C(=O)$OR_3$.

It may be that each of $W_1$ and $W_2$ is —P(=O)(U)(V) and the compound of the invention is a 2',5'-phosphoramidate of the parent 3'-deoxynucleoside. In certain preferred embodiments, where each of $W_1$ and $W_2$ is —P(=O)(U)(V), U is —OAr and V is —$NR_4$—$CR_1R_2$—C(=O)$OR_3$. In certain preferred embodiments, $W_1$ is the same as $W_2$.

Ar may be unsubstituted. Ar may be substituted. Where Ar is substituted, it can be substituted with one, two, three, four or five substituents. The substitutents may be selected from: halo, $C_1$-$C_4$-alkyl, $C_1$-$C_4$-alkoxy, nitro and cyano.

Ar, whether substituted or unsubstituted, may be selected from the group consisting of phenyl, pyridyl, naphthyl and quinolyl. In certain preferred embodiments, Ar is selected from the group consisting of phenyl and naphthyl. In further preferred embodiments, where Ar is naphthyl, binding to —O—P is at the 1-position on naphthyl. In further preferred embodiments, Ar is unsubstituted phenyl or unsubstituted naphthyl, with binding to —O—P at the 1-position on naphthyl.

$R_1$ and $R_2$ may be selected such that the moiety —$CR_1R_2COO$— corresponds to the corresponding part of a naturally occurring alpha amino acid.

It may be that each of $R_1$ and $R_2$ are independently selected from Me and H. In certain preferred embodiments, one of $R_1$ and $R_2$ is Me and one of $R_1$ and $R_2$ is H such that the C atom bearing $R_1$ and $R_2$ has the same absolute configuration as L-alanine.

It may be that $R^1$ is H. It may be that $R^2$ is $C_1$-$C_4$ alkyl. It may be that $R^2$ is methyl. It may be that the C atom bearing $R_1$ and $R_2$ has the same absolute configuration as L-alanine.

It may be that each of $R_1$ and $R_2$ is Me. It may be that each of $R_1$ and $R_2$ is H.

It may be that have $R_3$ is selected from the group consisting of $C_{6-30}$aryl$C_{1-6}$alkyl and unsubstituted $C_{1-20}$alkyl. In certain preferred embodiments, $R_3$ is selected from the group consisting of benzyl (—$CH_2$-Ph), unsubstituted methyl (—$CH_3$) and unsubstituted n-pentyl (-n-$C_5H_{11}$). In further preferred embodiments, $R_3$ is benzyl.

$R_4$ may be H.

U and V may be selected independently from —$NR_5R_6$. Preferably, each of U and V is the same. In further preferred embodiments, $R_8$ is H and $R_7$ is selected from the group comprising H, methyl, i-propyl, —$CH_2Ph$, —$CH_2CH(CH_3)_2$ and —$CH(CH_3)(CH_2H_5)$. In further preferred embodiments, $R_7$ is methyl. In further preferred embodiments, the stereochemistry of the C atom bearing $R_7$ and $R_8$ has the same absolute configuration as L-alanine. Alternatively, the stereochemistry of the C atom bearing $R_7$ and $R_8$ can have the same absolute configuration as D-alanine. In certain preferred embodiments, $R_9$ is selected from the group consisting of branched and unbranched $C_1$-$C_{13}$ acyclic alkyl, $C_3$-$C_{18}$ cyclic alkyl and $C_{6-30}$aryl$C_{1-6}$alkyl, any of which is optionally substituted. In certain preferred embodiments, $R_9$ is benzyl.

In certain embodiments, a compound of the present invention comprises U and V, wherein each of U and V is selected, independently, from —$NR_5R_6$ wherein $R_5$ and $R_6$ together with the N atom to which they are attached form a ring moiety comprising 5 to 8 ring atoms. U and V may be the same.

Q may be O.

It may be that $W_1$ is —P(=O)(U)(V), where U is —O-1-naphthyl and V is —NH-(L)CH($CH_3$)—C(=O)—O—$CH_2$-Ph, $W_2$ is H and Q is O.

It may be that each of X and Z independently selected from the group consisting of H, OH, F, Cl, $NH_2$, SH and —$SC_{1-6}$alkyl and Y selected from the group consisting of H, OH, F, Cl, —$OC_{1-6}$alkyl, $NH_2$, $C_{2-8}$alkynyl, SH and —$SC_{1-6}$alkyl. It may be that X is $NR^{12}R^{13}$, e.g. $NH_2$. In certain preferred embodiments, Z is H. In further preferred embodiments, X is $NH_2$ and Z is H. In preferred embodiments, X is NH$_2$, Y is H and Z is H; X is NH$_2$, Y is F and Z is H; X is NH$_2$, Y as Cl and Z is H; or X is NH$_2$, Y is —OCH$_3$ and Z as H. In certain preferred embodiments, X is NH$_2$, Y is H and Z is H and so provide compounds of the invention which are derivatives of cordycepin (3'dA).

In certain particularly preferred embodiments, Ar is phenyl, R$^3$ is benzyl and R$^2$ is methyl.

Compounds of the present invention wherein, when P is asymmetric, the compound can consist of the diastereoisomer R$_p$, the diastereoisomer S$_p$ or a mixture of the diastereoisomers R$_p$ and S$_p$.

Preferred compounds of the invention include:
(2S)-Benzyl 2-(((((2S,4R,5R)-5-(6-amino-9H-purin-9-yl)-4-hydroxytetrahydrofuran-2-yl)methoxy)(naphthalen-1-yloxy)phosphoryl)amino)propanoate;
Benzyl 2-(((((2S,4R,5R)-5-(6-amino-9H-purin-9-yl)-4-hydroxytetrahydrofuran-2-yl)methoxy)(phenoxy)phosphoryl)amino)acetate;
(2S)-Pentyl 2-(((((2S,4R,5R)-5-(6-amino-9H-purin-9-yl)-4-hydroxytetrahydrofuran-2-yl)methoxy)(naphthalen-1-yloxy)phosphoryl)amino)-4-methylpentanoate;
Methyl 2-(((((2S,4R,5R)-5-(6-amino-9H-purin-9-yl)-4-hydroxytetrahydrofuran-2-yl)methoxy)(naphthalen-1-yloxy)phosphoryl)amino)-2-methylpropanoate;
(2S)-Benzyl 2-(((((2S,4R,5R)-5-(6-amino-9H-purin-9-yl)-4-hydroxytetrahydrofuran-2-yl)methoxy)(2-(3-ethoxy-3-oxopropyl)phenoxy)phosphoryl)amino)propanoate;
(2S)-Benzyl 2-(((((2R,3R,5S)-2-(6-amino-9H-purin-9-yl)-5-(hydroxymethyl)tetrahydrofuran-3-yl)oxy)(phenoxy) phosphoryl)amino)propanoate;
Benzyl 2-(((((2S,4R,5R)-5-(6-amino-9H-purin-9-yl)-4-(((((1-(benzyloxy)-1-oxopropan-2-yl)amino)(phenoxy) phosphoryl)oxy)tetrahydrofuran-2-yl)methoxy)(phenoxy)phosphoryl)amino)propanoate;
(2S)-Benzyl 2-(((((2R,3R,5S)-2-(6-amino-9H-purin-9-yl)-5-(hydroxymethyl)tetrahydrofuran-3-yl)oxy)(naphthalen-1-yloxy)phophoryl)amino)proponate;
Benzyl 2-[({[5-(6-amino-9H-purin-9-yl)-4-hydroxyoxolan-2-yl]methoxy}({[1-(benzyloxy)-1-oxopropan-2-yl]amino})phosphoryl)amino]propanoate;
(2S)-Benzyl 2-((((2S,4R,5R)-5-(6-amino-2-methoxy-9H-purin-9-yl)-4-hydroxytetrahydrofuran-2-yl)methoxy) (naphthalen-1-yloxy)phosphorylamino)propanoate;
(2S)-Benzyl 2-((((2S,4R,5R)-5-(6-amino-2-methoxy-9H-purin-9-yl)-4-hydroxytetrahydrofuran-2-yl)methoxy) (phenoxy)phosphorylamino)propanoate;
(2S)-Benzyl 2-(((((2S,4R,5R)-5-(6-amino-2-fluoro-9H-purin-9-yl)-4-hydroxytetrahydrofuran-2-yl)methoxy)(phenoxy)phosphoryl)amino)propanoate;
(2S)-Hexyl 2-(((((2S,4R,5R)-5-(6-amino-2-fluoro-9H-purin-9-yl)-4-hydroxytetrahydrofuran-2-yl)methoxy)(phenoxy)phosphoryl)amino)propanoate;
(2R)-Benzyl 2-((((2S,4R,5R)-5-(6-amino-2-chloro-9H-purin-9-yl)-4-hydroxytetrahydrofuran-2-yl)methoxy)(naphthalen-1-yloxy)phosphorylamino)propanoate;
3'-Deoxyadenosine-5'-O-[phenyl(benzyloxy-L-alaninyl)] phosphate;
2-O-Methyl-3'-deoxyadenosine-5'-O-[1-naphthyl(1-pentyloxy-L-leucinyl)] phosphate;
2-O-Methyl-3'-deoxyadenosine-5'-O-[phenyl(1-hexyloxy-L-alaninyl)] phosphate;
2-Fluoro-3'-deoxyadenosine-5'-O-[1-naphthyl(benzyloxy-L-alaninyl)] phosphate;
2-Fluoro-3'-deoxyadenosine-5'-O-[1-naphthyl(1-pentyloxy-L-leucinyl)] phosphate;
2-Chloro-3'deoxyadenosine 5'-O-[1-phenyl (2,2-dimethyl-propoxy-L-alanine)] phosphate;
2-Chloro-3'deoxyadenosine 5'-O-[1-naphtyl (2,2-dimethyl-propoxy-L-alanine)] phosphate;
2-Chloro-3'deoxyadenosine 5'-O-[1-phenyl (ethoxy-L-alanine)] phosphate; and
(2S)-isopropyl-2-(((((2S,4R,5R)-5-(6-amino-9H-purin-9-yl)-4-hydroxytetrahydrofuran-2-yl)methoxy)(phenoxy) phosphoryl)amino)propanoate and pharmaceutically acceptable salts, esters, salts of an ester, solvates or prodrugs thereof.

In certain embodiments, the compound of the invention is not:
(2S)-isopropyl-2-(((((2S,4R,5R)-5-(6-amino-9H-purin-9-yl)-4-hydroxytetrahydrofuran-2-yl)methoxy)(phenoxy) phosphoryl)amino)propanoate.

According to a second aspect of the present invention, there is provided a compound of the present invention for use in a method of treatment. The compound may be for use in the prophylaxis or treatment of cancer.

According to a third aspect of the present invention there is provided use of a compound of the present invention in the manufacture of a medicament for the prophylaxis or treatment of particularly, although not exclusively, of cancer.

According to a fourth aspect of the present invention, there is provided a method of prophylaxis or treatment of particularly, although not exclusively, of cancer comprising administration to a patient in need of such treatment an effective dose of a compound of the present invention.

With respect to each of the second, third and fourth aspects of the present invention, embodiments of the invention comprise a cancer selected from among haematological and solid tumours. In particular, the cancer can be selected from the group consisting of leukaemia, multiple myeloma, liver cancer, breast cancer, head and neck cancer, neuroblastoma, thyroid carcinoma, skin cancer (including melanoma), oral squamous cell carcinoma, urinary bladder cancer, Leydig cell tumour, colon cancer, colorectal cancer, lung cancer (non-small cell and small cell), biliary cancer, pancreatic cancer, sarcoma, prostate cancer, cancer of the central nervous system, Ewing's sarcoma, Cholangiocarcinoma and gynaecological cancers, including ovarian cancer, uterine cancer and cervical cancer, including epithelia cervix carcinoma. In preferred embodiments, the cancer is leukaemia or lymphoma, e.g. a cancer selected from the group consisting of acute lymphoblastic leukaemia, acute myelogenous leukaemia, acute promyelocytic leukaemia, acute lymphocytic leukaemia, chronic myelogenous leukaemia, chronic lymphocytic leukaemia, monoblastic leukaemia, hairy cell leukaemia, Hodgkin lymphoma and non-Hodgkin lymphoma. In further preferred embodiments, the cancer is acute lymphoblastic leukaemia.

Each of the second, third and fourth aspects of the invention can comprise embodiments for treating cancer employed in combination with other cancer therapy. Examples of other cancer therapy include radiotherapy and/or other chemotherapy. Without being bound by theory or mechanism, it has been reported (e.g. Robertson, J. B. et al Int. J. Radiat. Biol. Relat. Stud. Phys. Chem. Med. 1978 34(5): 417-29, Hiraoka, W. et al Radiat. Res. (1988) 114(2): 231-9 and Hiraoka, W. et al J. Radiat. Res. (Tokyo) (1990) 31(2): 156-61) that 3'-deoxyadenosine inhibits the repair of X-ray induced DNA damage. In certain preferred embodiments of each of the second, third and fourth aspects of the present invention the compounds of the invention are for use in, or are used in, a method of treatment of cancer comprising administration to a patient in need of such treatment a compound of the present invention in conjunction with radiotherapy.

With respect to each of the second, third and fourth aspects of the present invention, further embodiments of the invention comprise compounds of the invention for use in, or are used in, a method of prophylaxis or treatment of myelodysplastic syndrome.

Without being bound by theory or mechanism: Tuli et al (supra) reported that cordycepin, as well as having anti-tumour activity and apoptotic activity, also shows anti-oxidant, anti-inflammatory, anti-malarial, anti-fungal, immunomodulatory, anti-diabetic/hyopglycemic, steroidogenesis and anti-aging activities; Vodnala, S. K. et al J. Med. Chem. 2013, 56, 9861-9873 reported that each of cordycepin and 2-fluorocordycepin shows anti-parasitic activity; Ahn, Y. J. et al J. Agric. Food Chem. 2000 48 (7) 2744-8 reported that cordycepin shows anti-bacterial activity and de Julian-Ortiz J. V. et al J. Med. Chem. 1999 42 (17) 3308-14 reported that cordycepin shows anti-viral activity; Sugar et al, *Antimicrob. Agents. Chemother.* 1998 42 (6) 1424-7, showed that cordycepin has antifungal activity. With respect to each of the second, third and fourth aspects of the present invention, embodiments of the invention comprise compounds of the invention for use in, or are used in, a method of prophylaxis or treatment of a patient with a disease or condition in need of at least one treatment selected from the group consisting of anti-oxidant, anti-inflammatory, anti-malarial, anti-fungal, immunomodulatory, anti-diabetic/hypoglycemic, steroidogenesis, anti-aging, anti-parasitic, anti-bacterial and anti-viral activity.

With respect to each of the second, third and fourth aspects of the invention, embodiments of the invention comprise compounds of the present invention for use in, or are used in, a method of prophylaxis or treatment wherein the method does not employ the administration of a co-drug which is an inhibitor of adenosine deaminase. Unlike the parent compound cordycepin, which typically needs to be co-administered with an ADA inhibitor, to be effective it may be that the compounds of the invent do not require such co-administration.

An ADA inhibitor can, however, be employed as a co-drug, if desired, with respect to each of the second, third and fourth aspects of the invention. A suitable ADA inhibitor for co-administration with a compound embodying the present invention is hydroxyurea or pentastatin.

According to a further aspect of the present invention, there is provided a pharmaceutical composition comprising a compound of the present invention in combination with a pharmaceutically acceptable carrier, diluent or excipient.

According to a further aspect of the present invention, there is provided a method of preparing a pharmaceutical composition comprising the step of combining a compound of the present invention with a pharmaceutically acceptable carrier, diluent or excipient.

According to further aspect of the present invention, there is provided a method of preparing a compound of formula (Ia):

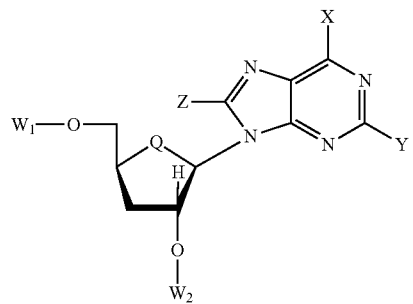

by reacting a compound of formula IV:

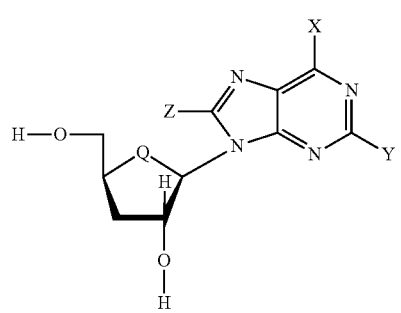

with:
(a) a compound of formula V:

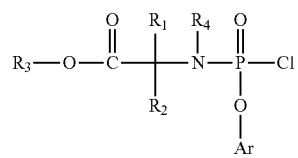

or
(b) POCl$_3$ followed by a salt of N$^+$R$_5$R$_6$H$_2$, where W$_1$, W$_2$, Q, X, Y, Z, Ar, R$_1$, R$_2$, R$_3$, R$_4$, R$_5$ and R$_6$ have the meanings set out herein with respect to formula (Ia).

Compounds embodying the present invention have surprisingly been found to have enhanced pharmaceutical activity, particularly enhanced anti-cancer activity, compared to their parent purine-based 3'-deoxynucleoside (i.e. wherein W$_1$ and W$_2$ are H), especially when employed in the treatment of leukaemia, lymphoma and/or solid tumours.

The enhancement in activity has been found in the absence of administration of a co-drug to inhibit adenosine deaminase, compared to the parent purine-based nucleoside administered in the absence of a co-drug to inhibit ADA.

The present invention thus unexpectedly provides a means to employ a derivative of 3'-deoxyadenosine, or a derivative of an analogue of 3'-deoxyadenosine, as a pharmaceutical agent, particularly as an anti-cancer agent, that mitigates the problem of deamination by adenosine deaminase, whilst avoiding completely, if desired, the use of a co-drug which is an inhibitor of adenosine deaminase, including the relatively toxic 2-deoxycoformycin.

Without being bound by any theory, the efficacy, particularly the anticancer efficacy, exhibited by compounds of the present invention demonstrates that the 3'-deoxynucleoside compounds of the present invention are phosphorylated intracellularly to 3'-deoxyadenosine triphosphate, or to the triphosphate of a 3'-deoxyadenosine analogue. Where the compounds of the present invention have $W_1$ as —P—(=O)(U)(V), it is believed that enzymic cleavage of U and V within the cell converts the compounds directly into 3'-deoxyadenosine monophosphate, or the monophosphate of the 3'-deoxyadenosine analogue, prior to phosphorylation to the triphosphate.

None of the above intracellular activity of compounds of the present invention could have been predicted beforehand.

The above benefits are in addition to enhanced cellular membrane permeability of the phosphoramidate nucleosides of the present invention, compared to the 3'-deoxyadenosine parent or the 3'-deoxyadenosine analogue parent, where enhanced cell membrane permeability is attributable to the phosphoramidate structure of the present compounds. The benefit of enhanced cellular membrane permeability cannot, moreover, be assumed to be present a priori for the phosphoramidate of any nucleoside. The compounds of the present invention are, it is believed, the first example of a phosphoramidate of a 3'-deoxynucleoside to show an enhanced anti-cancer potency, relative to their parent 3'-deoxynucleoside. The benefit of enhanced cellular membrane permeability by compounds of the present invention is thus surprising.

Preferred embodiments of the compounds of the present invention have, in combination, the features set out above with respect to embodiments of the compounds of the invention.

Each of Ar, $R_1$, $R_2$, $R_3$ and $R_4$ can be substituted with one, two, three, four or five substituents.

Substituents on Ar can be located ortho-, meta-, para- or otherwise on the aromatic groups. Substituents on Ar are independently selected from the group consisting of hydroxy, $C_{1-6}$acyl, $C_{1-6}$acyloxy, nitro, amino, carboxyl, $C_{2-6}$ester, $C_1$-6aldehyde, cyano, $C_{1-6}$alkylamino, di$C_{1-6}$alkylamino, thiol, chloro, bromo, fluoro, iodo, $C_{1-6}$alkyl, $C_{2-6}$alkenyl, $C_{1-6}$alkoxy$C_{1-6}$alkyl, $C_{1-6}$alkoxy$C_{6-10}$aryl, $C_{5-7}$cycloalkyl, $C_{5-11}$cycloalkyl$C_{1-6}$alkyl, $C_{5-7}$cycloalkenyl, $C_{8-12}$cycloalkynyl, $C_{6-11}$aryl$C_{1-6}$alkyl, $C_{1-6}$alkyl$C_{6-11}$aryl, $C_{6-11}$aryl, $C_{1-6}$fluoroalkyl, $C_{2-6}$fluoroalkenyl, $SO_3H$, SH and SR', wherein R' is independently selected from the same group set out above as $R_1$ with respect to formula Ia. Each substituent can be substituted by any other substituent.

Substituents on $R_1$, $R_2$, $R_3$ and $R_4$ are independently selected from the group consisting of hydroxy, $C_{1-6}$acyl, $C_{1-6}$acyloxy, nitro, amino, amido, carboxy, $C_{2-6}$ester, $C_{1-6}$aldehyde, cyano, $C_{1-6}$alkylamino, di$C_{1-6}$alkylamino, thiol, chloro, bromo, fluoro, iodo, $C_{5-7}$cycloalkyl, $C_{5-7}$ cycloalkenyl, $C_{8-12}$cycloalkynyl, $C_{6-11}$aryl, $C_{6-11}$aryl$C_{1-6}$alkyl, $_{5-20}$heterocyclyl, $SO_3H$, SH and SR', wherein R' independently selected from the same group set out above as $R_1$ with respect to formula Ib.

In certain preferred embodiments, $R_1$ and $R_2$ are independently selected from the group consisting of H, $C_{1-10}$alkyl, $C_{6-30}$aryl$C_{1-6}$alkyl, $C_{2-10}$alkenyl, $C_{2-10}$alkoxy$C_{1-10}$alkyl, $C_{1-10}$alkoxy$C_{6-10}$aryl, $C_{2-10}$alkynyl, $C_{3-20}$cycloalkyl, $C_{3-20}$cycloalkenyl, $C_{8-20}$cycloalkynyl, and $_{5-10}$heterocyclyl.

In certain embodiments, $R_1$ and/or $R_2$ correspond to a side chain, including H, of a naturally occurring alpha amino acid, which can have L or D stereochemistry. Thus, it may be that $R_1$ and/or $R_2$ (e.g. a single one or $R^1$ and $R^2$) are selected from the group consisting of H, $CH_3$, —$CH(CH_3)_2$, —$CH_2CH(CH_3)_2$, —$CH(CH_3)(CH_2CH_3)$, —$CH_2Ph$, —$CH_2Ph$-OH, —$CH_2SH$, —$CH_2CH_2SCH_3$, —$CH_2OH$, $CH(CH_3)(OH)$, —$CH_2CH_2CH_2CH_2NH_{3+}$, —$CH_2CH_2CH_2NHC(=NH_2^+)NH_2$, —$CH_2C(O)O$—, —$CH_2CH_2C(O)O$—, —$CH_2C(O)NH_2$, —$CH_2CH_2C(O)NH_2$,

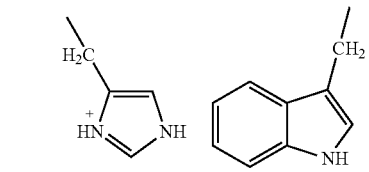

In certain preferred embodiments, $R_1$ and $R_2$ are independently selected from the group consisting of H, —$CH_3$ and —$CH_2CH(CH_3)_2$. In further preferred embodiments, $R_1$ and $R_2$ together correspond to the side chains of L alanine.

$R_3$ may be selected from the group consisting of H, $C_{1-20}$alkyl, $C_{6-30}$aryl$C_{1-6}$alkyl, $C_{2-10}$alkenyl, $C_{1-10}$alkoxy$C_{1-10}$alkyl, $C_{1-10}$alkoxy$C_{6-10}$aryl, $C_{2-10}$alkynyl, $C_{3-20}$cycloalkyl, $C_{3-20}$cycloalkenyl, $C_{3-20}$cycloalkynyl, and $_{5-20}$heterocyclyl.

$R_3$ may be selected from the group consisting of H, $C_{1-20}$alkyl, $C_{6-30}$aryl$C_{1-6}$alkyl and $C_{3-20}$cycloalkyl. $R_3$ may be selected from the group consisting of $C_{6-30}$aryl$C_{1-6}$alkyl and unsubstituted $C_{1-20}$alkyl. In certain preferred embodiments, $R_3$ is selected from the group consisting of benzyl (—$CH_2Ph$), unsubstituted methyl (—$CH_3$) and unsubstituted n-pentyl (-n-$C_5H_{11}$). $R_3$ may be benzyl.

$R_4$ may be selected from the group consisting of H, $C_{1-20}$alkyl, $C_{6-30}$aryl$C_{1-6}$alkyl, $C_{2-10}$alkenyl, $C_{1-10}$alkoxy, $C_{1-10}$alkoxy$C_{1-10}$alkyl, $C_{1-10}$alkoxy$C_{6-10}$aryl, $C_{2-10}$alkynyl, $C_{3-20}$cycloalkyl, $C_{3-20}$cycloalkenyl, $C_{8-20}$cycloalkynyl, and $_{5-20}$heterocyclyl.

$R_4$ may be selected from the group consisting of H, $C_{1-18}$alkyl, $C_{6-30}$aryl$C_{1-6}$alkyl, $C_{3-20}$cycloalkyl and $_{5-20}$heterocyclyl. $R_4$ may be selected from the group consisting of H, methyl, ethyl, propyl, butyl, pentyl, hexyl and cyclohexyl. $R_4$ may be H.

The invention provides a compound of the invention for use in targeting cancer stem cells.

The invention provides the use of a compound of the invention in the manufacture of a medicament for targeting cancer stem cells.

The invention provides a method of targeting cancer stem cells, the method comprising providing a population of cancer stem cells with an amount of a compound of the invention sufficient to target such cancer stem cells.

The targeting of cancer stem cells referred to in the present invention may be employed in the prevention or treatment of cancer. In such embodiments the population of cancer stem cells may be in a cancer or pre-cancerous condition in a patient in need of such targeting, and the method may comprise administering a therapeutically effective amount of a compound of the invention to the patient.

The invention provides a compound of the invention for use as an anti-cancer stem cell medicament. This use of a compound of the invention may also be employed in the prevention or treatment of cancer.

The invention provides a method of determining whether a patient with cancer or a pre-cancerous condition will benefit from prevention or treatment of cancer with a compound of the invention, the method comprising:

assaying a biological sample representative of cancer or a pre-cancerous condition in the patient for the presence of cancer stem cells; wherein the presence of cancer stem cells in the biological sample indicates that the patient will benefit from treatment with a compound of the invention.

The invention provides a method of determining a suitable treatment regimen for a patient with cancer or a pre-cancerous condition, the method comprising:

assaying a biological sample representative of cancer or a pre-cancerous condition in the patient for the presence of cancer stem cells; wherein the presence of cancer stem cells in the biological sample indicates that a suitable treatment regimen will comprise treatment of the patient with a compound of the invention.

The invention provides a compound of the invention for use in the prevention or treatment of cancer in a patient selected for such treatment by a method comprising:

assaying a biological sample representative of cancer or a pre-cancerous condition in the patient for the presence of cancer stem cells; wherein the presence of cancer stem cells in the biological sample indicates that the patient is suitable for treatment with a compound of the invention.

The methods set out above may further comprise a step of preventing or treating the cancer or pre-cancerous condition using a compound of the invention.

In suitable embodiments of the methods of the invention the cancer is relapsed or refractory cancer. A compound of the invention may be used for the treatment of such relapsed or refractory cancer.

The invention provides a compound of the invention for use in treatment of refractory cancer in a subject. The subject may be a human patient. The subject may be a domestic animal, e.g. mammal.

The invention provides the use of a compound of the invention in the manufacture of a medicament for the treatment of relapsed or refractory cancer in a subject. The subject may be a domestic animal, e.g. mammal.

The invention provides a method of treating relapsed or refractory cancer in a subject, the method comprising providing a therapeutically effective amount of a compound of the invention to a subject in need of such treatment. The subject may be a domestic animal, e.g. mammal.

The invention provides a compound of the invention for use in the treatment of cancer, wherein a compound of the invention is for use at dose of between approximately 25 mg/m$^2$ and 4000 mg/m$^2$ per week in at least one initial cycle of treatment, and then for use at a lower weekly dose in at least one further cycle of treatment. The cancer may be a relapsed or refractory cancer.

Various aspects of the invention are based upon the finding that a compound of the invention is able to reduce cancer stem cell numbers, and may reduce these preferentially as compared to other cell types. This finding is surprising in that cancer stem cells are known to be resistant to many chemotherapeutic agents, and there has previously been no suggestion that either a compound of the invention or cordycepin or 2-fluorocordycepin, the parent prodrug compound from which a compound of the invention is derived, were able to target cancer stem cells. Thus the finding that a compound of the invention is able to target cancer stem cells and thus reduce their numbers, a finding which the inventors have confirmed is applicable across a broad range of cancers, represents a surprising breakthrough that enables a range of new therapeutic applications of a compound of the invention.

The biological activities exerted by the compounds of the invention, which have not previously been reported, indicate that these compounds are able to provide treatment that is likely to be effective in patients with relapsed or refractory cancers. Treatment of this sort, using the compounds of the invention, may bring about a reduction in tumour size and/or a reduction in clinically relevant biomarkers, either of which may be associated with more favourable prognosis. Furthermore, treatment with a compound of the invention may help to maintain a reduction in the size of tumours in patients with relapsed or refractory cancer. Accordingly, treatment using a compound of the invention may achieve a high, durable Disease Control Rate (DCR) in patients with relapsed or refractory cancers.

Without wishing to be bound by any hypothesis, the inventors believe that the ability of the compounds of the invention to target cancer stem cells contributes to the therapeutic utility of these compounds in the treatment of relapsed or refractory cancer.

Except for where the context requires otherwise, references within this disclosure to a "use" of a compound of the invention in accordance with the invention may be taken as applying to any of the medical uses of compounds of the invention described herein. Similarly, references to "methods" of the invention using a compound of the invention should be taken as applying to any of the methods of the invention herein described.

The ability of a compound of the invention to target cancer stem cells provides new therapies directed against those cancer cells that are considered most difficult to treat, and that are considered to play a major role in the resistance that limits effectiveness of many existing cancer therapies. This ability also provides a way of targeting cells that are believed to be associated with the development, progression, recurrence, and propagation of cancers. Accordingly, it will be recognised that this anti-cancer stem cell activity of a compound of the invention yields benefits in contexts in which new and effective therapies have long been sought.

BRIEF DESCRIPTION OF THE FIGURES

Embodiments of the invention are further described hereinafter with reference to the accompanying drawings, in which.

DETAILED DESCRIPTION

Figure 1:
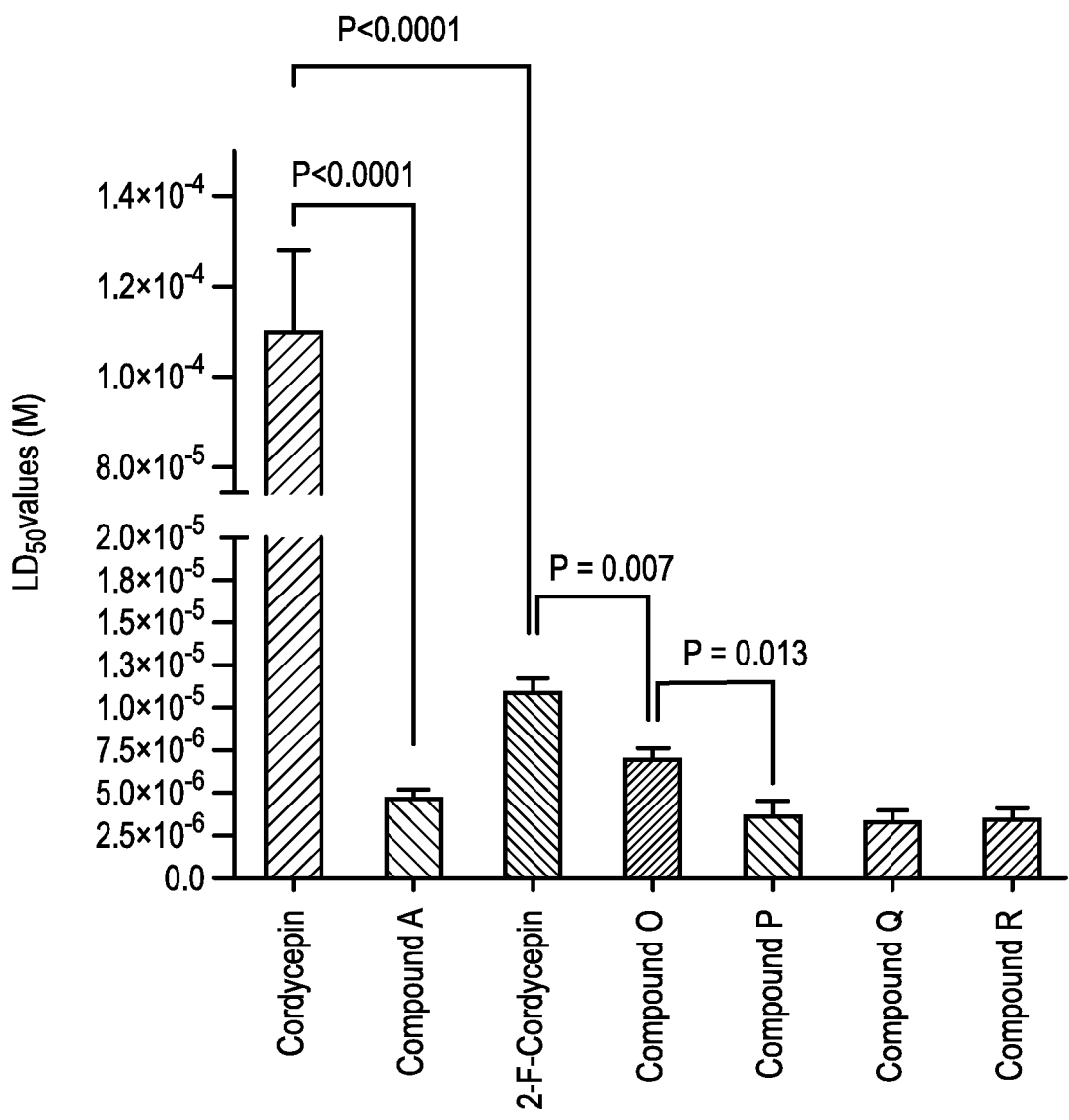
FIG. 1. Comparison of the LD$_{50}$ values for Cordycepin, Compounds A, 2-F-Cordycepin, Compounds O, P, Q and R. All assays were carried out using KG1a cells and data are presented as mean (±SD) of five independent experiments.

As used herein, the term "alkyl" refers to a straight or branched saturated monovalent (except where the context requires otherwise) cyclic or acyclic hydrocarbon radical, having the number of carbon atoms as indicated (or where not indicated, an acyclic alkyl group can have 1-20, 1-18, 1-10, 1-6 or 1-4 carbon atoms and a cyclic alkyl group can have 3-20, 3-10 or 3-7 carbon atoms), optionally substituted with one, two or three substituents independently selected from the group set out above with respect to substituents that may be present on $R_1$, $R_2$, $R_3$ and $R_4$. By way of non-limiting examples, alkyl groups can include methyl, ethyl, propyl, butyl, pentyl, hexyl, octyl, nonyl and dodecyl.

As used herein, the term "alkenyl" refers to a straight or branched unsaturated monovalent (except where the context requires otherwise) acyclic or cyclic hydrocarbon radical having one or more C=C double bonds and having the number of carbon atoms as indicated (or where not indicated, an acyclic alkenyl group can have 2-20, 2-10, 2-6 or 2-4 carbon atoms and a cyclic alkenyl group can have 3-20 or 5-7 carbon atoms), optionally substituted with one, two or three substituents independently selected from the group set out above with respect to substituents that may be present on $R_1$, $R_2$, $R_3$ and $R_4$. By way of non-limiting examples, alkenyl groups can include vinyl, propenyl, butenyl, pentenyl and hexenyl.

As used herein, the term "alkynyl" refers to a straight or branched unsaturated monovalent (except where the context requires otherwise) acyclic or cyclic hydrocarbon radical having one or more C≡C triple bonds and having the number of carbon atoms as indicated (or where not indicated, an acyclic alkynyl group can have 2-20, 2-10, 2-6 or 2-4 carbon atoms and a cyclic alkynyl group can have 8-20 carbon atoms), optionally substituted with one, two or three substituents independently selected from the group set out above with respect to substituents that may be present on $R_1$, $R_2$, $R_3$ and $R_4$.

As used herein, the term "alkoxy" refers to the group alkyl-O—, where alkyl is as defined above and where the alkyl moiety may optionally be substituted by one, two or three substituents as set out above for alkyl. Binding is through —O—. By way of non-limiting examples, alkoxy groups can include methoxy, ethoxy, n-propoxy, iso-propoxy, n-butoxy, tert-butoxy, sec-butoxy, n-pentoxy, n-hexoxy and 1,2-dimethylbutoxy.

As used herein, the term "aryloxy" refers to the group aryl-O—, where aryl is as defined below and where the aryl moiety may optionally be substituted by one, two or three substituents as set out above with respect to the group Ar. Binding is through —O—.

As used herein, the term "alkoxyalkyl" refers to an alkyl group having an alkoxy substituent. Binding is through the alkyl group. The alkyl moiety and the alkoxy moiety are as defined herein with respect to the definitions of alkyl and alkoxy, respectively. The alkoxy and alkyl moieties may each be substituted by one, two or three substituents as set out above with regard to the definition of alkyl.

As used herein, the term "arylalkyl" refers to an alkyl group having an aryl substituent. Binding is through the alkyl group. The aryl moiety and the alkyl group are as defined herein with respect to the definitions of aryl and alkyl, respectively. The aryl and alkyl moieties may each be substituted by one, two or three substituents, the substituents being as defined herein with respect to the definitions of those substituents that may be present with respect to aryl and alkyl, respectively. In a preferred embodiment, arylalkyl is benzyl, which is Ph-CH$_2$—.

As used herein, the term "alkoxyaryl" refers to an aryl group having an alkoxy substituent. Binding is through the aryl group. The alkoxy moiety and the aryl moiety are as defined herein with respect to the definitions of alkoxy and aryl, respectively. The alkoxy and aryl moieties may each be substituted by one, two or three substituents, the substituents being as defined herein with respect to the definitions of those substituents that may be present with respect to alkoxy and aryl, respectively.

As used herein, the term "cycloalkylaryl" refers to an aryl group having a cyclic alkyl substituent. Binding is through the aryl group. The cycloalkyl moiety and the aryl moiety are as defined herein with respect to the definitions of cycloalkyl and aryl, respectively. The cycloalkyl moiety and the aryl moiety may each be optionally substituted by one, two or three substituents as set out herein with regard to the definitions of alkyl and aryl, respectively.

As used herein, the term "aryl" refers to a monovalent (except where the context requires otherwise) aromatic carbocyclic radical having one, two, three, four, five or six rings and having the number of carbon atoms indicated (or where not indicated 6 to 30, 6 to 12 or 6 to 11 carbon atoms). A preferred embodiment has one, two or three rings. An aryl group may optionally be substituted by one, two, three, four or five substituents, as set out above with respect to optional substituents that may be present on the group Ar. In preferred embodiments, an aryl group comprises: an aromatic monocyclic ring containing 6 carbon atoms; an aromatic fused bicyclic ring system containing 7, 8, 9 or 10 carbon atoms; or an aromatic fused tricyclic ring system containing 10, 11, 12, 13 or 14 carbon atoms. Non-limiting examples of aryl include phenyl and naphthyl. In a preferred embodiment, optional substituent groups on an aryl group can be independently selected from hydroxy, $C_{1-6}$acyl, $C_{1-6}$acyloxy, nitro, amino, carboxyl, cyano, $C_{1-6}$alkylamino, di$C_{1-6}$alkylamino, thiol, chloro, bromo, fluoro, iodo, SO$_3$H, SH and SR', wherein R' is independently selected from the same groups as $R_1$ with respect to formula Ia.

As used herein, the term "$_{5-30}$heteroaryl" refers to a monovalent (except where the context requires otherwise) unsaturated aromatic heterocyclic radical having 5 to 30 ring members in the form of one, two, three, four, five or six fused rings and contained within at least one ring at least one heteroatom selected from the group consisting of N, O and S. A preferred embodiment has one, two or three fused rings. Available carbon atoms and/or heteroatoms in the ring system may be substituted on the ring with one, two, three, four or five substituents, as set out above with respect to the substituents that may be present on the group Ar. Heteroaryl groups can include an aromatic monocyclic ring system containing six ring members of which at least one ring member is a N, O or S atom and which optionally contains one, two or three additional ring N atoms; an aromatic monocyclic ring having six members of which one, two or three ring members are a N atom; an aromatic bicyclic fused ring system having nine members of which at least one ring member is a N, O or S atom and which optionally contains one, two or three additional ring N atoms; or an aromatic bicyclic fused ring system having ten ring members of which one, two or three ring members are a N atom. Examples include, and are not limited to, pyridyl and quinolyl.

As used herein, the term "$_{5-20}$heterocyclyl" refers to a monovalent (except where the context requires otherwise) saturated or partially unsaturated heterocyclic radical having 5 to 20 ring members, with at least one ring member selected from the group consisting of N, O and S, and being in the form of one, two, three, four, five or six fused rings. In a preferred embodiment, the radical has one, two or three rings. In a preferred embodiment, the radical has 5 to 10 ring members. Heterocyclyl radicals can include: a monocyclic ring system having five ring members of which at least one ring member is a N, O or S atom and which optionally contains one additional ring O atom or one, two or three additional ring N atoms; a monocyclic ring system having six ring members of which one, two or three ring members are a N atom and which optionally includes an O atom; a bicyclic fused ring system having nine ring members of which at least one ring member is a N, O or S atom and which optionally contains one, two or three additional ring N atoms; or a bicyclic fused ring system having ten ring members of which one, two or three ring members are a N atom. Examples include, and are not limited to, pyrrolinyl, pyrrolidinyl, 1,3-dioxolanyl, imidazolinyl, imidazolidinyl, pyrazolinyl, pyrazolidinyl, piperidinyl, morpholinyl or piperazinyl.

Available ring carbon atoms and/or ring heteroatoms of the "heterocyclyl" ring systems described above may be substituted with one, two, three, four or five substituents. Where the ring(s) is substituted with one or more heteroatoms, the heteroatom substituents are selected from halogen (F, Cl, Br and I) and from oxygen, nitrogen and sulphur, where the oxygen, nitrogen or sulphur form part of a substituent moiety. Where the ring(s) is substituted with one or more heteroatoms, preferably there are 1, 2, 3 or 4 heteroatom substituents selected from the group consisting of oxygen, nitrogen, sulphur and halogen. Examples of substituent groups that can be present on the heterocyclic ring system can be independently selected from hydroxy, $C_{1-6}$acyl, $C_{1-6}$acyloxy, nitro, amino, carboxyl, cyano, $C_{1-6}$alkylamino, di$C_{1-6}$alkylamino, thiol, chloro, bromo, fluoro, iodo, $SO_3H$, SH and SR', wherein R' is independently selected from the same groups as $R_1$ with respect to formula Ia.

As used herein, the term "acyl" refers to a straight or branched, saturated or unsaturated, substituted or unsubstituted, monovalent (except where the context requires otherwise) radical that includes the moiety —C(═O)—, where binding is through the —C— atom of —C(═O)— moiety, and has the number of carbon atoms indicated (or where not indicated, an acyl group has 1-6, or 1-4 or 1-2 carbon atoms, including the C atom of the —C(═O)— moiety), optionally substituted with one, two or three substituents independently selected from the group set out above with respect to the substituents that may be present on $R_1$, $R_2$, $R_3$ and $R_4$. By way of non-limiting examples, acyl groups include HC(═O)—, $CH_3$C(═O)—, $C_2H_5$C(═O)—, $C_3H_7$C(═O)—, $C_4H_9$C(═O)— and $C_5H_{11}$C(═O)—.

As used herein, the term "acyloxy" refers to a straight or branched, saturated or unsaturated, substituted or unsubstituted monovalent (except where the context requires otherwise) radical that includes the moiety —C(═O)—O—, where binding is through the —O— atom, and has the number of carbon atoms indicated, including the C atom of the —C(═O)—O— moiety (or where not indicated, an acyloxy group has 1-6, 1-4 or 1-2 carbon atoms, including the carbon atom of the —C(═O)—O— moiety), optionally substituted with one, two or three of the substituents that may be present on $R_1$, $R_2$, $R_3$ and $R_4$. By way of non-limiting examples, acyloxy groups include HC(═O)—O—, $CH_3$C(═O)—O—, $C_2H_5$C(═O)—O—, $C_3H_7$C(═O)—O—, $C_4H_9$C(═O)—O— and $C_5H_{11}$C(═O)═O—.

As used herein, the term "$C_{2-6}$ester" refers to a substituted or unsubstituted monovalent (except where the context requires otherwise) radical that comprises $R_{18}$C(═O)—O—$R_{19}$, where $R_{18}$ is selected from the group consisting H and $C_{1-4}$alkyl and $R_{19}$ is selected from the group consisting of $C_{1-5}$alkyl, subject to the maximum total number of C atoms, including the C atom of the —C(═O)—O— moiety, of $R_{18}$C(═O)—O—$R_{19}$ being six. Binding is through $R_{18}$ or $R_{19}$, with an H of the respective group absent such that the alkyl group through which binding occurs is divalent, or, when $R_{18}$ is H, through the C of the —C(═O)—O— moiety.

In a preferred embodiment, the $C_{2-6}$ester, including the C atom of the —C(═O)—O moiety, has 2-5 carbon atoms. The $C_{2-6}$ester can optionally be substituted with one, two or three substituents independently selected from the group set out above with respect to the substituents that may be present on $R_1$, $R_2$, $R_3$ and $R_4$. By way of a non-limiting example, $C_{2-6}$ester can be —$C_2H_4$—C(═O)—O—$C_2H_5$, where the —$C_2H_4$— moiety is —$CH_2$—$CH_2$— and binding is through the —$C_2H_4$— moiety.

As used herein, the term "aldehyde" refers to a straight or branched, saturated or unsaturated, substituted or unsubstituted monovalent (except where the context requires otherwise) radical that comprises HC(═O)—$R_{20}$—, where binding is through —$R_{20}$—, has the number of carbon atoms indicated, including the C atom of the —C(═O)— moiety (or where not indicated, an aldehyde group has 1-6, 1-4 or 1-2 carbon atoms, including the C atom of the —C(═O)— moiety), optionally substituted with one, two or three of the substituents that may present on $R_1$, $R_2$, $R_3$ or $R_4$. By way of non-limiting examples, aldehyde groups include HC(═O)—$CH_2$—, HC(═O)—$C_2H_4$—, HC(═O)—$C_3H_6$—, HC(═O)—$C_4H_8$— and HC(═O)—$C_5H_{10}$—.

As used herein, the term "fluoroalkyl" refers to an alkyl group, where the alkyl group is a straight or branched saturated monovalent (except where the context requires otherwise) cyclic or acyclic hydrocarbon radical, having the number of carbon atoms as indicated (or where not indicated, an acyclic alkyl group has 1-6 or 1-4 carbon atoms and a cyclic alkyl group has 3-6 carbon atoms) substituted with 1 to 6 F atoms.

As used herein, the term "fluoroalkenyl" refers to an alkenyl group, where the alkenyl group is a straight or branched unsaturated monovalent (except where the context requires otherwise) acyclic or cyclic hydrocarbon radical having one or more C═C double bonds and having the number of carbon atoms as indicated (or where not indicated, an acyclic alkenyl group has 2-6 or 2-4 carbon atoms and a cyclic alkenyl group has 4-6 carbon atoms) substituted with 1 to 6 F atoms.

The process for preparing a compound of formula Ia or Ib is preferably carried out in the presence of a suitable solvent.

Suitable solvents include hydrocarbon solvents such as benzene and toluene; ether type solvents such as diethyl ether, tetrahydrofuran, diphenyl ether, anisole and dimethoxybenzene; halogenated hydrocarbon solvents such as methylene chloride, chloroform and chlorobenzene; ketone type solvents such as acetone, methyl ethyl ketone and methyl isobutyl ketone; alcohol type solvents such as methanol, ethanol, propanol, isopropanol, n-butyl alcohol and tert-butyl alcohol; nitrile type solvents such as acetonitrile, propionitrile and benzonitrile; ester type solvents such as ethyl acetate and butyl acetate; carbonate type solvents such as ethylene carbonate and propylene carbonate; and the like. These may be used singly or two or more of them may be used in admixture.

Preferably an inert solvent is used in the process of the present invention. The term "inert solvent" means a solvent inert under the conditions of the reaction being described in conjunction therewith including, for example, benzene, toluene, acetonitrile, tetrahydrofuran, dimethylformamide, chloroform, methylene chloride (or dichloromethane), diethyl ether, ethyl acetate, acetone, methylethyl ketone, methanol, ethanol, propanol, isopropanol, tert-butanol, dioxane, pyridine, and the like. Tetrahydrofuran is particularly preferred.

Preferably the process of the present invention is carried out under substantially dry conditions.

The phosphorochloridate may be prepared from an aryloxy phosphorodichloridate and a suitably protected amino acid derivative. Alternatively, phosphate chemistry may be used with suitable condensing agents.

Preferably the process for preparing the compound of formula Ib can include the step of protecting free OH groups, on the nucleoside other than that to which the phosphoramidate is to be attached. For example, carrying out the reaction of the 3'-deoxynucleoside with the desired phosphorochloridate in the presence of $_t$-BuMgCl allows the 2'-phosphoramidate to be prepared.

Reacting the 3'-deoxynucleoside with $POCl_3$ followed by a salt of $N^+R_5R_6H_2$ allows compounds to be prepared where each of U and V is —$NR_5R_6$. Suitable salts include chloride, tosylate, sulphonate and ester salts such as 4-methylbenzene sulphonate. Subsequent addition of a base such as diisopropylethyl amine can aid the process.

As used herein, the term "stereoisomer" defines all possible compounds made up of the same atoms bonded by the same sequence of bonds but having different three-dimensional structures which the compounds of the present invention may possess.

Where the compounds according to this invention have at least one chiral centre, they may accordingly exist as enantiomers. Where the compounds possess two or more chiral centres, they may additionally exist as diastereoisomers. Where the processes for the preparation of the compounds according to the invention give rise to mixture of stereoisomers, these isomers may be separated by conventional techniques such as preparative chromatography. The compounds may be prepared in stereochemically mixed form or individual enantiomers may be prepared by standard techniques known to those skilled in the art, for example, by enantiospecific synthesis or resolution, formation of diastereoisomeric pairs by salt formation with an optically active acid, followed by fractional crystallization and regeneration of the free base. The compounds may also be resolved by formation of diastereoisomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

Furthermore, it should be appreciated that the phosphate centre is chiral in the compounds of the present invention and the compounds may exist as $R_P$ and $S_P$ diastereoisomers. The composition of the compound may be mixed $R_P$ and $S_P$ or one pure diastereoisomer. In a preferred embodiment, the compound is a substantially pure single diastereoisomer of either $R_P$ or $S_P$. By "substantially pure single diastereoisomer" is meant that the compound consists of 98% or more of either the $R_P$ or the $S_P$ diastereoisomer. In another embodiment, there may be a mixture of 1:1 $R_P$ to $S_P$ diastereoisomers. Alternatively, the compound may comprise a mixture of $R_P$ and $S_P$ diastereoisomers in a ratio of $R_P$ to $S_P$ diastereoisomers of 1:90 to 90:1, 1:50 to 50:1, 1:20 to 20:1, 1:15 to 15:1, 1:10 to 10:1, 1:9 to 9:1, 1:8 to 8:1, 1:7 to 7:1, 1:6 to 6:1, 1:5 to 5:1, 1:4 to 4:1, 1:3 to 3:1 or 1:2 to 2:1. In preferred embodiments, the compound of the invention may comprise a ratio of $R_P$ to $S_P$ diastereoisomers of greater than 1:2, 1:3, 1:4, 1:5, 1:6, 1:7, 1:8, 1:9, 1:10, 1:15, 1:20, 1:50, 1:90, 1:95 or 1:99 or vice versa.

The term "solvate" means a compound of formula Ia or formula Ib as defined herein, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a hydrate.

The compounds of the present invention may also be present in the form of pharmaceutical acceptable salts. For use in medicine, the salts of the compounds of this invention refer to "pharmaceutically acceptable salts." FDA approved pharmaceutical acceptable salt forms (Ref. International J. Pharm. 1986, 33, 201-217; J. Pharm. Sci., 1977, January, 66 (1)) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, maleate, mandelate, mesylate, methylbromide, methylnitrate, methylsulfate, mucate, napsylate, nitrate, pamoate, pantothenate, phosphate, diphosphate, polygalacturonate, salicylate, stearate, subacetate, succinate, sulfate, tannate, tartrate, teoclate, tosylate and triethiodide.

Pharmaceutically acceptable basic/cationic salts include, and are not limited to aluminum, benzathine, calcium, chloroprocaine, choline, diethanolamine, ethylenediamine, lithium, magnesium, potassium, procaine, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Pharmaceutically acceptable ester derivatives in which one or more free hydroxy groups are esterified in the form of a pharmaceutically acceptable ester are particular examples of prodrug esters that may be convertible by solvolysis under physiological conditions to the compounds of the present invention having free hydroxy groups.

Pharmaceutical compositions for use in accordance with the present invention may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen.

The compound or pharmaceutical composition according to the present invention can be administered to a patient, which may be *Homo sapiens* or animal, by any suitable means.

The medicaments employed in the present invention can be administered by oral or parenteral routes, including intravenous, intramuscular, intraperitoneal, subcutaneous, transdermal, airway (aerosol), rectal, vaginal and topical (including buccal and sublingual) administration.

For oral administration, the compounds of the invention will generally be provided in the form of tablets or capsules, as a powder or granules, or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while cornstarch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

In general a suitable dose will be in the range of 0.1 to 300 mg per kilogram body weight of recipient per day. A more suitable dose may be in the range of 0.5 mg to 150 mg per kilogram body weight of recipient per day, in the range of 0.5 to 100 mg per kilogram body weight of recipient per day, in the range of 1 to 50 mg per kilogram body weight of recipient per day, or in the range of 1 to 10 mg per kilogram body weight of recipient per day. A suitable a lower dose may be 0.5 mg per kilogram body weight of recipient per day or 1 mg per kilogram body weight of recipient per day. Alternatively, a suitable dose may be in the range of 1 to 100 mg per $m^2$ of body surface area of recipient per day or 5 to 50 mg per $m^2$ of body surface area of recipient per day. Suitable doses may be 6, 12, 24 or 48 mg per $m^2$ of body surface area of recipient per day. The desired dose may be presented and administered as a single daily dose or as two, three, four, five or six or more sub-doses administered at appropriate intervals throughout the day. Doses may be administered in unit dosage forms, for example, containing 10 to 1500 mg, preferably 20 to 1000 mg, and most preferably 50 to 700 mg of active ingredient per unit dosage form. The total daily dose is suitably 1000 to 3000 mg, whether taken as a single dose or as sub-doses at intervals throughout the day.

"Cancer Stem Cells"

Cancer stem cells, which are sometimes otherwise referred to as "tumour initiating cells", are well known to those skilled in the art. As used herein, the term "cancer stem cell" is to be interpreted in accordance with its widely accepted meaning, which is a cell that possesses the capacity to self-renew through asymmetric division, to initiate tumour formation, and to give rise to more mature non-stem cell cancer progeny by differentiation.

Cancer stem cells play a major role in the development, progression, recurrence and propagation of cancers. Accordingly, the finding that compounds of the invention are able to target cancer stem cells, and thereby reduce their numbers, offers therapeutic possibilities in preventing or treating these activities.

As discussed in more detail elsewhere in the specification, cancer stem cells are found in pre-cancerous conditions, where their presence is believed to contribute to the development of such conditions into cancers. Accordingly the methods of treatment and medical uses of the invention, in which a compound of the invention is used to target cancer stem cells, may be used to reduce cancer stem cell numbers in pre-cancerous conditions (such as myelodyplastic syndrome, or other conditions considered elsewhere in the specification), and thus to prevent progression of such pre-cancerous conditions into cancer.

As referred to above, asymmetric cell division of cancer stem cells gives rise to differentiated non-stem cancer cells. Thus cancer stem cells are responsible for the formation and maintenance of the bulk of the tumour.

The accumulation of such non-stem cancer cells plays a major role in the progression of cancers. Targeting of cancer stem cells by a compound of the invention is able to reduce cancer stem cell numbers, which in turn reduces the number of non-stem cancer cell progeny. Thus methods of treatment and medical uses of a compound of the invention in accordance with the present invention are of benefit in treating cancer by preventing cancer progression. Such embodiments are described in more details elsewhere in the present specification.

Cancer stem cells are also able to act as a reservoir of cancer cells that they may cause the recurrence of cancer after remission. Even in the event that the majority of a patient's cancer cells have been removed (for example by surgery, radiotherapy, or chemotherapy, either alone or in combination), so that no observable signs of a cancer remain, the continued presence of cancer stem cells may nucleate the recurrence of the cancer over time. Targeting of cancer stem cells by a compound of the invention provides a new mode by which cancer stem cell numbers may be reduced and cancer stem cells killed. Accordingly, and as discussed in more detail elsewhere in the specification, in suitable embodiments the present invention provides methods and medical uses in which a compound of the invention prevents or delays recurrence of cancer.

Furthermore, movement of cancer stem cells from the site of a cancer to another location within the body can contribute to propagation of cancer, for example by giving rise to metastases. Consequently, the ability of a compound of the invention to target cancer stem cells therefore provides new methods of treatment and medical uses in preventing or treating cancer propagation.

In addition to their biological activities, cancer stem cells may be identified by their expression of certain characteristic cell surface markers. Cancer stem cells identified in haematological malignancies are typically $CD34^+$, while in solid tumours, $CD44^+$, $CD133^+$ and $CD90^+$ have been identified as cancer stem cell markers. The following table summarises examples of known cancer stem cell surface phenotypes. It is expected that each of these forms of cancer stem cell can be targeted using a compound of the invention in accordance with the invention, and so methods or uses employing a compound of the invention may be used in the prevention or treatment of cancers associated with cancer stem cells expressing any of these sets of markers.

| Tumour type | Reported cell surface markers for cancer stem cells |
| --- | --- |
| Solid Tumours | |
| Breast | $CD44^+/CD24^{-/low}$/Lineage$^-$/ESA$^+$ |
| CNS | $CD133^+$ |
| Colon | $CD133^+$ |
| Colon | $ESA^{high}/CD44^+$/Lineage$^-$/($CD166^+$) |
| Ewing's | $CD133^+$ |
| Head and Neck | $CD44^+$/Lineage$^-$ |
| Melanoma | $ABCB5^+$ |
| Liver | $CD90^+/CD45^-/(CD44^+)$ |
| Cholangiocarinoma | $CD44^+/GLI1^+$ (Glioma-associated oncogene homolog-1) |
| Ovarian | $CD44^+/CD117^+$ |
| Pancreas | $CD44^+/CD24^+/ESA^+$ |
| Pancreas | $CD133^+$ |
| Non-small-cell lung cancer | $CD44^+/Ber-EP4^+$ |
| Bladder cancer | $CD44^+/ALDH1A1^+$ |
| Haematological tumours | |
| Acute myeloid leukaemia | $Lin^-/CD34^+/CD38^-/CD123^+$ |
| B-Acute lymphoblastic leukaemia | $CD34^+/CD10^-$ or $CD34^+/CD19^-$ |
| B-Acute lymphoblastic leukaemia | $CD34^+/CD38^-/CD19^+$ |
| Multiple myeloma | $CD34^-/CD138^-$ |
| T-Acute lymphoblastic leukaemia | $CD34^+/CD4^-$ or $CD34^+/CD7^-$ |

The data presented in the Examples demonstrate that a compound of the invention is able to target cancer stem cells of leukaemic stem cell lines, specifically cancer stem cells present in the acute myeloid leukaemia cell line KG1a. This cell line manifests a minor stem cell-like compartment with a distinct immunophenotype ($Lin^-/CD34^+/CD38^-/CD123^+$) which is targeted by a compound of the invention. Accordingly, methods of treatment or medical uses of a compound of the invention in accordance with the present invention may be used to prevent or treat leukaemia or other cancers associated with cancer stem cells expressing these characteristic markers.

The present invention also provides methods and medical uses in which patients are selected for prevention or treatment of cancer, utilising a compound of the invention, on the basis of the identification of the presence of cancer stem cells in a biological sample representative of the patient's cancer or pre-cancerous condition. The markers set out above provide suitable examples that can be used to identify the presence of cancer stem cells in accordance with such embodiments of the invention. Suitable techniques by which expression of these markers may be investigated in a biological sample are considered further elsewhere in this specification.

"Targeting of Cancer Stem Cells"

The present invention provides the first indication that compounds of the invention can be used for targeting cancer stem cells. The ability of compounds of the invention to target cancer stem cells is illustrated in the Examples disclosed in this specification.

It can be seen that when a compound of the invention is provided to populations of cancer cells containing cancer stem cells it targets the cancer stem cells present, leading to a reduction in the total number of cancer cells. As discussed elsewhere in the present specification, certain compounds of the invention preferentially target cancer stem cells as opposed to bulk tumour cells, and the activity of such compounds is able not only to reduce the total number of cancer cells present, but also to reduce the proportion of total cancer cells that exhibit phenotypic markers of cancer stem cells.

It is believed that the compounds of the present invention enter into cancer cells and are incorporated into nucleic acids (RNA and/or DNA) with the cells. Without being bound by any theory, it is believed that the efficacy, particularly the anti-cancer efficacy, exhibited by compounds of the present invention demonstrates that compounds of the present invention are phosphorylated to the triphosphate of cordycepin or a cordycepin derivate (e.g. 2-fluorocordycepin or 2-Cl-cordycepin) and it is believed that enzymatic cleavage within the cell converts a compound of the invention directly into 8-chloroadenosine monophosphate prior to phosphorylation to the triphosphate.

It is also believed that the compounds of the invention possess enhanced cellular membrane permeability (as compared to cordycepin), and that this contributes to the enhanced anti-cancer potency of the compounds of the invention compared to the parent from which they are derived.

Without wishing to be bound by any hypothesis, the inventors believe that the reduction in cancer stem cell numbers arises as a result of targeted killing of the cancer stem cells among the cancer cell population. Thus compounds of the invention are able to cause the death of cancer stem cells. Furthermore, the results set out elsewhere in this specification illustrate that certain compounds of the invention appear to kill cancer stem cells preferentially as compared to killing of non-stem cancer cells, thereby causing not only the death of cancer stem cells, but also a reduction of the proportion of cancer stem cells among the total cancer cell population.

While the inventors believe that compounds of the invention that preferentially target cancer stem cells preferentially kill cancer stem cells as compared to non-stem cancer cells, other mechanisms may also contributed to the reduction in the proportion of cancer stem cells caused by a compound of the invention's targeting of these cells.

Merely by way of example, treatment with a compound of the invention may cause an increase in cancer stem cell differentiation, thereby reducing cancer stem cell numbers and also the proportion of total cancer cells represented by cancer stem cells. Alternatively, a compound of the invention may cause cancer stem cells to lose their stem cell phenotype, for example losing their ability to self-renew, thereby reducing cancer stem cell numbers.

References to targeting of cancer stem cells in the present disclosure should be interpreted accordingly. For the purposes of the present disclosure, "targeting" of cancer stem cells may be taken as encompassing any mechanism by which a compound of the invention reduces the number of cancer stem cells present in a population of cells, whether in vitro or in vivo. In particular targeting of cancer stem cells may be taken as encompassing preferential reduction of cancer stem cell numbers as compared to other cell types, particularly as compared to non-stem cancer cells. References to targeting in this specification may be taken as including the killing, and optionally preferential killing, of cancer stem cells as compared to non-stem cancer cells.

"Prevention or Treatment of Cancer"

The invention provides medical uses and methods of treatment in which a compound of the invention is used for the prevention or treatment of cancer. In the context of the present invention, "prevention" of cancer is to be considered as relating to prophylactic applications of a compound of the invention used before the development of cancer, and with an aim of stopping cancer from developing. On the other hand "treatment" of cancer is taken as concerning the use of a compound of the invention after cancer has occurred, with a view to ameliorating cancer by slowing or stopping cancer cell proliferation and tumour growth. Advantageously treatment of cancer may cause partial or total reduction in cancer cell numbers and tumour size. Effective treatment of cancer may bring about disease that either "stabilizes" or "responds" in accordance with the RECIST (Response Evaluation Criteria In Solid Tumours) guidelines.

As described in more detail below, prevention of cancer in accordance with the present invention may be of particular benefit in patients who have a pre-cancerous condition that increases their likelihood of developing cancer.

"Prevention of Cancer"

Prevention of cancer in accordance with the present invention may be effected by treatment of a pre-cancerous condition using a compound of the invention in accordance with the various aspects or embodiments of the invention described herein.

In particular, prevention of cancer, in the context of the present invention, may be achieved by the methods or medical uses of the invention in which a compound of the invention is provided to a patient with a pre-cancerous condition. Methods of treatment or medical uses in accordance with this embodiment may prevent development of the treated pre-cancerous condition into cancer, thereby providing effective prevention of cancer.

References to prevention of cancer in the context of the present invention may also encompass other prophylactic applications of a compound of the invention. For example, the ability of a compound of the invention to target cancer stem cells and thereby prevent the development of cancer, and/or prevent the progression of cancer, and/or prevent the recurrence of cancer, and/or prevent the propagation of cancer.

"Pre-Cancerous Conditions"

Cancer is frequently preceded by the development of a pre-cancerous condition, which is not itself cancerous, but is associated with an increased risk of cancer. Accumulation of genetic or epigenetic changes may cause previously normal cells to develop a cancer stem cell phenotype. Accordingly, cancer stem cells may also be present in such pre-cancerous conditions, as well as in cancerous conditions.

It is believed that the presence of cancer stem cells in pre-cancerous conditions contributes to the development of these conditions into cancer. The methods and medical uses of the invention may be employed to target cancer stem cells present in pre-cancerous conditions, and thereby treat such conditions. It will be appreciated that the new and unexpected finding that compounds of the invention target cancer stem cells means that treatment of pre-cancerous conditions with such compounds may be used to prevent the treated conditions developing into cancer. This represents a way in which a compound of the invention can be used medically in the prevention of cancer, as considered elsewhere in this specification.

Examples of pre-cancerous conditions that may be treated in accordance with the present invention include, but are not limited to, those selected from the group consisting of: actinic keratosis, Barrett's oesophagus, atrophic gastritis, dyskeratosis congenital, Sideropenic dysphagia, Lichen planus, oral submucous fibrosis, solar elastosis, cervical dysplasia, leukoplakia, erythroplakia, monoclonal gammopathy of unknown significance (MGUS), monoclonal B-cell lymphocytosis (MBL), myelodysplastic syndromes, as well as pre-cancerous conditions of the stomach such as atrophic gastritis, gastric ulcer, pernicious anaemia, gastric stumps, gastric polyps, and Ménétrier's disease. Among the listed pre-cancerous conditions of the stomach, atrophic gastritis, pernicious anaemia, gastric stumps, and certain types of gastric polyp may have particularly heightened risk of developing into cancers.

Pre-cancerous conditions often take the form of lesions comprising dysplastic or hyperplastic cells. Accordingly, the presence of dysplasia or hyperplasia, as an alternative or addition to the presence of cells with expressed markers or phenotypes characteristic of cancer stem cells, may be used in the identification of pre-cancerous conditions.

The severity of dysplasia can vary between different pre-cancerous conditions, or with the development of a single pre-cancerous condition over time. Generally, the more advanced dysplasia associated with a pre-cancerous condition is, the more likely it is that the pre-cancerous condition will to develop into cancer. Dysplasia is typically classified as mild, moderate or severe. Severe dysplasia usually develops into cancer if left untreated. Suitably, methods of treatment or medical uses employing a compound of the invention may therefore be used to treat a patient with a pre-cancerous condition associated with severe dysplasia.

In a suitable embodiment of the invention a compound of the invention is used to treat a patient with severe cervical dysplasia. Severe cervical dysplasia may be diagnosed by means of a smear test. In another embodiment of the invention a compound of the invention is used to treat severe oesophageal dysplasia ("Barrett's oesophagus"). Severe oesophageal dysplasia may be diagnosed following a tissue biopsy.

It has recently been reported that pre-malignancies can also be identified by detecting somatic mutations in cells in individuals not known to have cancer. In particular, it has been reported that age-related clonal haematopoiesis is a common pre-malignant condition that is associated with increased overall mortality and increased risk of cardiometabolic disease. The majority of mutations detected in blood cells occurred in three genes: DNMT3A, TET2, and ASXL1. Accordingly, patients that will benefit from the use of a compound of the invention to target cancer stem cells, and thereby treat a pre-cancerous condition, may be identified by assaying a sample comprising blood cells for the presence of genetic mutations indicative of a pre-cancerous condition in at least one of: DNMT3A and/or TET2 and/or ASXL1.

Pre-cancerous conditions that may benefit from treatment with a compound of the invention in accordance with the invention to target cancer stem cells may also be identified by determination of the presence of cancer stem cells with reference to any of the techniques based upon expression of markers characteristic of cancer stem cells, or cancer stem cell phenotypes, discussed elsewhere in the specification.

"Treatment of Cancer"

The skilled person will appreciate that there are many measurements by which "treatment" of cancer may be assessed. Merely by way of example, any reduction or prevention of cancer development, cancer progression, cancer recurrence, or cancer propagation may be considered to indicate effective treatment of cancer.

In certain embodiments, a compound of the invention may be used: to reduce the proportion of cancer stem cells in a population of cancer cells; and/or to inhibit tumour growth; and/or to reduce tumourigenicity; and/or to prevent or treat a primary cancer; and/or to prevent or treat a relapsed cancer; and/or to prevent or treat a metastatic or secondary cancer; and/or to treat, prevent or inhibit metastasis or recurrence; and/or to treat or prevent refractory cancer.

The ability of cancer treatment using a compound of the invention to bring about a reduction in tumour size, and also to maintain the reduction in tumour size during/after the period in which the treatment is administered represents a particularly relevant indication of effective cancer treatment. As set out in the Examples, the treatments or medical uses of the invention have proven surprisingly effective in this respect, even in models using cells representative of relapsed or refractory cancers that have previously been resistant to treatment with other therapies.

The data presented in the Examples illustrate that treatment with a compound of the invention reduces the proportion of cancer stem cells in a population of cancer cells. Characteristic biological activities or cell surface markers by which cancer stem cells may be identified are described elsewhere in the specification. In a suitable embodiment, treatment of cancer in accordance with the present invention may give rise to a reduction in the proportion of cancer stem cells present in a patient's cancer of at least 10%, at least 20%, at least 30%, or at least 40%. In suitable embodiments treatment of cancer in accordance with the invention may give rise to a reduction in the proportion of cancer stem cells present in a patient's cancer of at least 50%, at least 60%, at least 70%, or at least 80%. Treatment of cancer in accordance with the invention may give rise to a reduction in the proportion of cancer stem cells present in a patient's cancer of at least 85%, at least 90%, or at least 95%. Indeed, treatment of cancer in accordance with the invention may give rise to a reduction in the proportion of cancer stem cells present in a patient's cancer of at least 96%, at least 97%, at least 98%, at least 99%, or even 100% (such that substantially no cancer stem cells remain).

Asymmetric division of cancer stem cells contributes to the growth of tumours. Treatment of cancer with a compound of the invention in accordance with the present invention may bring about an inhibition of tumour growth of at least 10%, at least 20%, at least 30%, or at least 40%. Suitably treatment of cancer in accordance with the invention may give rise to an inhibition of tumour growth of at least 50%, at least 60%, at least 70%, or at least 80%. Treatment of cancer in accordance with the invention may give rise to an inhibition of tumour growth of at least 85%, at least 90%, or at least 95% in a patient so treated. Indeed, treatment of cancer in accordance with the invention may give rise to an inhibition of tumour growth of at least 96%, at least 97%, at least 98%, at least 99%, or even 100% in a treated cancer.

Tumour growth may be assessed by any suitable method in which the change in size of a tumour is assessed over time. Suitably the size of a tumour prior to cancer treatment may be compared with the size of the same tumour during or after cancer treatment. A number of ways in which the size of a tumour may be assessed are known. For example, the size of a tumour may be assessed by imaging of the tumour in situ within a patient. Suitable techniques, such as imaging techniques, may allow the volume of a tumour to be determined, and changes in tumour volume to be assessed.

As shown in the results set out in the Examples of this specification, the methods of treatment and medical uses of a compound of the invention of the invention are able not only to arrest tumour growth, but are actually able to bring about a reduction in tumour volume in patients with cancers, including patients with relapsed or refractory cancers. Suitably treatment of cancer in accordance with the present invention may give rise to a reduction in tumour volume of at least 10%, at least 20%, at least 30%, or at least 40%. In suitable embodiments, treatment of cancer in accordance with the invention may give rise to a reduction in tumour volume of at least 50%, at least 60%, at least 70%, or at least 80%. Treatment of cancer in accordance with the invention may give rise to a reduction in tumour volume of at least 85%, at least 90%, or at least 95%. Indeed, treatment of cancer in accordance with the invention may give rise to a reduction in tumour volume of at least 96%, at least 97%, at least 98%, at least 99%, or even 100%.

A reduction in tumour volume of the sort described above can be calculated with reference to a suitable control. For example in studies carried out in vitro, or in vivo in suitable animal models, the reduction in tumour volume may be determined by direct comparison between the volume of a tumour treated with a compound of the invention and the volume of a control tumour (which may be untreated, or may have received treatment other than with a compound of the invention). It will be appreciated that such models requiring lack of treatment of a tumour may not be ethically acceptable in the context of clinical trials or therapeutic management of patients, and in this case a reduction in tumour volume may be assessed by comparing the volume of a treated tumour with the volume of the same tumour prior to treatment, or with a predicted volume that would have been attained by the tumour had no treatment been administered.

The methods of treatment and medical uses of a compound of the invention may bring about a reduction in biomarkers indicative of cancer. The reduction of such biomarkers provides a further assessment by which effective treatment of cancer may be demonstrated. Suitable examples of such biomarkers may be selected on the basis of the type of cancer to be treated: in the case of gynaecological cancers CA125 represents a suitable example of a biomarker, while in the case of pancreatic or biliary cancers CA19.9 represents a suitable example of a biomarker, and in the case of colorectal cancers CEA may be a suitable biomarker.

Suitably treatment of cancer in accordance with the present invention may give rise to a reduction in cancer biomarkers of at least 10%, at least 20%, at least 30%, or at least 40%. In suitable embodiments, treatment of cancer in accordance with the invention may give rise to a reduction in cancer biomarkers of at least 50%, at least 60%, at least 70%, or at least 80%. Treatment of cancer in accordance with the invention may give rise to a reduction in cancer biomarkers of at least 85%, at least 90%, or at least 95%. Indeed, treatment of cancer in accordance with the invention may give rise to a reduction in cancer biomarkers of at least 96%, at least 97%, at least 98%, at least 99%, or even 100%.

Beneficial effects, such as a reduction in the proportion of cancer stem cells present, reduction in tumour growth, or reduction in tumour volume or cancer biomarkers, observed on treatment of cancer in accordance with the present invention may be maintained for at least one month. Suitably such beneficial effects may be maintained for at least two months, at least three months, at least four months, at least five months, or at least six months. Indeed, such beneficial effects may be maintained for at least 12 months, at least 18 months, or at least 24 months. Suitably the beneficial effects may be maintained for at least three years, at least four years, at least five years, at least six years, at least seven years, at least eight years, at least nine years, or for ten years or more.

In a suitable embodiment of the invention a compound of the invention is used in a method of preventing or treating cancer or a pre-malignant condition, by targeting cancer stem cells. In a suitable embodiment the invention provides the use of a compound of the invention in a method of preventing or treating cancer or a pre-malignant condition, wherein the method reduces the tumourigenicity of one or more cancer stem cells. Suitably such methods may prevent the progression of cancer, or inhibit tumour growth.

When a compound of the invention is used in methods or medical uses of the present invention to prevent or treat the progression of a cancer, such prevention or treatment may cause the cancer progression to be slowed, delayed or stopped entirely.

The progress of a cancer is typically determined by assigning a stage to the cancer. Staging is usually carried out by assigning a number from I to IV to the cancer, with I being an isolated cancer and IV being a cancer that has spread to the limit of what the assessment measures. Specifics of staging vary between cancers, but the stage generally takes into account the size of a tumour, whether it has invaded adjacent organs, how many regional (nearby) lymph nodes it has spread to (if any), and whether it has appeared in more distant locations (metastasised).

Generally, Stage I is localised to one part of the body and may be treated by surgical resection (for solid tumours that are small enough). Stage II is locally advanced, and is treatable by chemotherapy, radiation therapy, surgery, or a combination thereof. Stage III is also locally advanced and the designation of Stage II or Stage III depends on the specific type of cancer, although Stage III is generally accepted to be "late" locally advanced. Stage IV cancers have often metastasised to a second organ. Treatment of cancer using a compound of the invention in the methods or medical uses of the present invention may be used to treat a stage I, II, III or IV cancer by targeting cancer stem cells. Treatment with a compound of the invention may be used to prevent the progression of a cancer from one stage to the next. In one embodiment, treatment with a compound of the invention is used to prevent progression from Stage I to Stage II. In another embodiment, treatment with a compound of the invention is used to prevent progression from Stage II to Stage III. In still another embodiment, treatment with a compound of the invention is used to prevent progression from Stage III to Stage IV.

Preventing or inhibiting progression of the cancer is particularly important for preventing the spread of the cancer, for example the progression from Stage I to Stage II where the cancer spreads locally, or the progression from Stage III to Stage IV where the cancer metastasises to other organs. Cancer stem cells are tumourigenic and so are believed to play a critical role in the spread of cancer, both locally and metastatically. Methods of treatment or medical uses of the invention employing a compound of the invention can therefore be used to prevent the spread of cancer, by targeting tumourigenic cancer stem cells and thus reducing their numbers.

"Cancers"

Compounds of the invention demonstrate increased anti-cancer activity as compared to parent nucleosides from which they are derived. This increase anti-cancer activity appears to be provided as a result of increased activity against both cancer stem cells and non-stem cancer cells.

Cancer stem cells play a role in the biological activity of a wide range of cancers. Accordingly, there are a wide range of cancers that may be prevented or treated in accordance with the present invention.

As discussed elsewhere herein, cancer stem cells are known to be present in many tumour types including liquid tumours (including haematological tumours such as leukaemias and lymphomas) and solid tumours (such as breast, lung, colon, prostate, ovarian, skin, bladder, biliary and pancreas tumours). Methods of treatment and medical uses of a compound of the invention to target cancer stem cells are therefore expected to be useful in the prevention or treatment of such cancers.

Suitably a compound of the invention may be used in the prevention or treatment of a cancer selected from the group consisting of: leukaemia, lymphoma, multiple myeloma, lung cancer, liver cancer, breast cancer, head and neck cancer, neuroblastoma, thyroid carcinoma, skin cancer (including melanoma), oral squamous cell carcinoma, urinary bladder cancer, Leydig cell tumour, biliary cancer, such as cholangiocarcinoma or bile duct cancer, pancreatic cancer, colon cancer, colorectal cancer and gynaecological cancers, including ovarian cancer, endometrial cancer, fallopian tube cancer, uterine cancer and cervical cancer, including epithelia cervix carcinoma. In suitable embodiments, the cancer is leukaemia and can be selected from the group consisting of acute lymphoblastic leukaemia, acute myelogenous leukaemia (also known as acute myeloid leukaemia or acute non-lymphocytic leukaemia), acute promyelocytic leukaemia, acute lymphocytic leukaemia, chronic myelogenous leukaemia (also known as chronic myeloid leukaemia, chronic myelocytic leukaemia or chronic granulocytic leukaemia), chronic lymphocytic leukaemia, monoblastic leukaemia and hairy cell leukaemia. In further preferred embodiments, the cancer is acute lymphoblastic leukaemia. In a particular embodiment, the leukaemia is refractory TdT-Positive Leukemia In a suitable embodiment the cancer is lymphoma, which may be selected from the group consisting of: Hodgkin's lymphoma; non-Hodgkin lymphoma; Burkitt's lymphoma; and small lymphocytic lymphoma.

Suitably targeting cancer stem cells in such cancers may achieve effective treatment of the cancer by preventing or treating the development of the cancer, by preventing or treating the progression of the cancer, by preventing or treating the recurrence of the cancer, or by preventing or treating the propagation of the cancer.

In a suitable embodiment the present invention provides a compound of the invention for use in targeting cancer stem cells in the prevention or treatment of metastatic cancer.

In a suitable embodiment the present invention provides a compound of the invention for use in targeting cancer stem cells in the treatment of relapsed or refractory cancer.

In a suitable embodiment the present invention provides a compound of the invention for use in targeting cancer stem cells in the treatment of a primary cancer. Suitably the primary cancer treated may be a second primary cancer.

The invention provides a compound of the invention for use in targeting cancer stem cells in the treatment of secondary cancer. In a suitable embodiment the secondary cancer is a metastatic cancer.

In a suitable embodiment the present invention provides a compound of the invention for use in targeting cancer stem cells, wherein the targeting of cancer stem cells prevents or inhibits: (i) recurrence of a cancer; (ii) occurrence of second primary cancer; or (iii) metastasis of a cancer.

Methods of treatment or medical uses in which a compound of the invention is employed on the basis of its ability to target cancer stem cells may be used in the treatment of relapsed or refractory cancer. The considerations regarding relapsed or refractory cancer in such embodiments are, except for where the context requires otherwise, the same as for the treatment of relapsed or refractory cancer in connection with the aspects of the invention.

"Relapsed or Refractory Cancer"

As noted above, certain aspects and embodiments of the invention particularly relate to the use of a compound of the invention in the treatment of relapsed or refractory cancers.

For the purposes of the present invention, refractory cancers may be taken as cancers that demonstrate resistance to treatment by anti-cancer therapies other than those utilising a compound of the invention. For example, a compound of the invention may be used in the treatment of refractory cancers that are resistant to treatment with radiotherapy. Alternatively, or additionally, a compound of the invention may be used in the treatment of refractory cancers that are resistant to biological agents used in the treatment of cancer. In a suitable embodiment a compound of the invention may be used in the treatment of refractory cancers that are resistant to treatment with chemotherapeutic agents other than a compound of the invention.

In particular, refractory cancers that may benefit from the methods of treatment of medical uses of the invention employing a compound of the invention include those cancers that are resistant to cordycepin or 2-fluorocordycepin.

Relapsed cancers (or recurrent cancers) are those that return after a period of remission during which the cancer cannot be detected. Cancer recurrence may occur at the site of the original cancer (local cancer recurrence), at a site close to that of the original cancer (regional cancer recurrence), or at a site distant from that of the original cancer (distal cancer recurrence). Cancer stem cells are believed to play a role in the recurrence of cancer, providing a source from which cells of the relapsed cancer are generated. Accordingly, the methods of treatment and medical uses of a compound of the invention in accordance with the invention, which enable targeting of cancer stem cells, may be of great benefit in the context of relapsed cancers. The ability of a compound of the invention to target cancer stem cells may be used to remove the populations of such cells that are able to give rise to recurrence, thus preventing incidences of relapsed cancer. The anti-cancer stem cell activity of a compound of the invention may also be used to target cancer stem cells in cancers that have recurred, as well as potentially exerting cytotoxic effects on non-stem cancer cells, thereby providing treatment of relapsed cancers.

In view of the above, it will be appreciated that a compound of the invention may be used in the methods or uses of the invention for the prevention or treatment of a relapsed cancer. A compound of the invention may be used in the methods or uses of the invention for the prevention or treatment of a local, regional or distant relapsed cancer.

A compound of the invention may be used in the methods or uses of the invention to prevent the recurrence of cancer by providing at least 2 months, at least 6 months, at least 12 months, at least 18 months, at least 24 months, or at least 30 months of remission. Indeed, a compound of the invention may be used to prevent recurrence of cancer by providing at least 4 years, at least 5 years, at least 6 years, at least 7 years, at least 8 years, at least 9 years, or at least 10 years of remission.

A compound of the invention may be used in the methods or uses of the invention to treat a relapsed cancer which has recurred after at least 2 months, at least 6 months, at least 12 months, at least 18 months, at least 24 months, or at least 30 months of remission. Indeed, a compound of the invention may be used to treat a relapsed cancer which has recurred after at least 4 years, at least 5 years, at least 6 years, at least 7 years, at least 8 years, at least 9 years, or at least 10 years of remission.

The ability of the compounds of the invention to target cancer stem cells gives rise to the ability of these compounds to prevent or treat cancers in accordance with the medical uses or methods of treatment of the invention. However, it should be noted that compounds of the invention also exert a direct cytotoxic effect upon non-stem cancer cells that make up the bulk of tumours. While activity of cancer stem cells may underlie much of the resistance that makes relapsed or refractory cancers so difficult to treat, non-stem cancer cells are also a major constituent of such relapsed or refractory cancers.

Compounds of the invention exert greater cytotoxic effects on non-stem cancer cells than does cordycepin or 2-fluorocordycepin, the chemotherapeutic molecule from which the compounds of the invention are derived. Accordingly, the mechanism by which a compound of the invention acts in the treatment of relapsed or refractory cancer may not be limited solely to the anti-cancer stem cell activity of this compound, but may also make use of the action of a compound of the invention on non-stem cancer cells. In such uses treatment with a compound of the invention will reduce the total number of both cancer stem cells and non-stem cancer cells. When certain compounds of the invention are utilised such treatments will preferentially reduce the proportion of cancer stem cells that remain after treatment.

Therapeutically Effective Doses of a Compound of the Invention

A therapeutically effective amount of a compound of the invention may be an amount sufficient to induce death of cancer cells. A therapeutically effective amount of a compound of the invention may be an amount sufficient to induce death of cancer stem cells. In some embodiments, particularly those relating to the treatment of relapsed or refractory cancer, a therapeutically effective amount of a compound of the invention may be an amount sufficient to induce death of cancer stem cells and also to induce death of non-stem cancer cells.

There are various different ways in which the amount of a therapeutically effective compound, such as a compound of the invention, to be administered to a patient may be calculated and expressed. One such way which is considered particularly relevant in doses of agents for the prevention or treatment of cancer, is in the amount of the agent to be administered per unit of body surface area of the patient. Such doses are typically expressed in terms of the amount of the agent (which may be determined by mass) per square meter ($m^2$) of surface area.

Uses of a compound of the invention for the prevention or treatment of cancer may utilise a weekly dose of between 10 mg/m$^2$ and 1000 mg/m$^2$. Such treatments may, for example utilise a weekly dose of between 375 mg/m$^2$ and 900 mg/m$^2$. For example, effective treatment of relapsed or refractory cancers may be provided when patients are provided with weekly doses of a compound of the invention that range between approximately 500 mg/m$^2$ and 825 mg/m$^2$.

Without wishing to be bound by any hypothesis, the inventors believe that the ability of a compound of the invention to target cancer stem cells allows therapeutic effectiveness to be achieve using lower doses of this compound than would otherwise be expected. Merely by way of example, weekly doses of a compound of the invention that are as low as 825 mg/m$^2$, 750 mg/m$^2$, 600 mg/m$^2$, or 500 mg/m$^2$ may prove therapeutically effective in the uses and methods of the invention.

A chosen weekly dose of a compound of the invention may be provided in a single incidence of administration, or in multiple incidences of administration during a week. For example, a weekly dose of a compound of the invention may be provided in two incidences of administration, in three incidences of administration, or more. Thus, in the case of a weekly dose of 750 mg/m$^2$, this may be achieved by three administrations of 250 mg/m$^2$ over the course of a week, or two administrations of 375 mg/m$^2$ during a week Similarly, in the case of a weekly dose of 600 mg/m$^2$, this may be achieved by three administrations of 200 mg/m$^2$ over the course of a week, or two administrations of 300 mg/m$^2$ during a week.

A suitable amount of a compound of the invention to be administered in a single incidence of treatment in order to provide a required dose of this compound over the course of week may be between approximately 100 mg/m$^2$ and 300 mg/m$^2$.

The weekly dose of a compound of the invention provided may decrease over the course of treatment. For example, treatment may be started at a weekly dose of around 1000 mg/m$^2$, 900 mg/m$^2$, 825 mg/m$^2$, 750 mg/m$^2$, or 725 mg/m$^2$, and over the course of treatment the dose needed may decrease to around 750 mg/m$^2$ (in cases where the initial dose is above this amount), around 650 mg/m$^2$, around 625 mg/m$^2$, or even around 500 mg/m$^2$ or around 375 mg/m$^2$.

Doses of a compound of the invention can, of course, be presented in other manners. The most common of these is the amount of the active agent to be provided per unit body mass. It has been calculated that for an average human patient a dose of 1 mg/m$^2$ is equivalent to approximately 0.025 mg/kg body mass. Accordingly, the data indicate that a compound of the invention is effective for the treatment of relapsed or refractory cancer at doses ranging from approximately 6.25 mg/kg to approximately 25 mg/kg. A suitable dose may, for example, be of between about 9.5 mg/kg and 22.5 mg/kg. In a suitable embodiment a compound of the invention achieves effective treatment of relapsed or refractory cancers when patients are provided with weekly doses ranging between approximately 12.5 mg/kg and 20.5 mg/kg.

Considerations regarding formulations of a compound of the invention suitable for use in the methods of prevention or treatment and medical uses of the present invention are described elsewhere in this disclosure. In the case of injectable formulations of a compound of the invention, these may be administered intravenously. Intravenous administration may be achieved over any suitable time frame, for example in a ten minute injection, or the like.

Types of Treatment

In a suitable embodiment a compound of the invention may be used for targeting cancer stem cells as a first line treatment of cancer.

However, the finding that compounds of the invention are able to target cancer stem cells and thereby treat relapsed or refractory cancer illustrates that a compound of the invention is able to provide effective treatment of cancer in contexts in which other treatments have proved ineffective. Accordingly, in a suitable embodiment the present invention provides a compound of the invention for targeting cancer stem cells as a second line treatment of cancer. Indeed, in a suitable embodiment the present invention provides a compound of the invention for targeting cancer stem cells as a third, or further, line treatment of cancer.

In a suitable embodiment there is provided a compound of the invention for use as a neooadjuvant in the treatment of cancer. A neoadjuvant is an agent provided to a patient in order to reduce the size of a tumour prior to a "main" anti-cancer therapy, such as surgical removal of cancer. A compound of the invention may be used as a neoadjuvant therapy for a patient who will subsequently undergo surgical treatment of cancer and/or radiotherapy for cancer.

Alternatively, or additionally, the invention provides a compound of the invention for use as an adjuvant in the treatment of cancer. An adjuvant is an agent provided to a patient after a "main" anti-cancer therapy, such as surgical removal of cancer, in order to prevent the return of cancer after the main therapy. A compound of the invention may be used as an adjuvant for a patient who has undergone surgical treatment of cancer and/or radiotherapy for cancer.

A compound of the invention may be employed in the methods or uses of the invention in a monotherapy, which is to say in preventions or treatments in which a compound of the invention provides substantially all of the therapeutic activity that is made use of in the prevention or treatment.

Alternatively, the methods or uses of the invention may employ a compound of the invention in a combination therapy. In such embodiments a compound of the invention is used in conjunction with at least one further cancer therapy. The further cancer therapy may comprise surgery and/or radiotherapy. Additionally, or alternatively, the further cancer therapy may comprise use of at least one further therapeutic agent that contributes to the prevention or treatment of cancer to be achieved. Suitably such an agent may be a chemotherapeutic agent or a biological agent used in the prevention or treatment of cancer.

In a suitable embodiment of a combination therapy a compound of the invention and a further therapeutic agent may be provided to a patient at the same time. In a suitable example, the compound of the invention and a further therapeutic agent may be formulated as part of the same pharmaceutical composition. Alternatively the compound of the invention and a further therapeutic agent may be formulated separately for provision to the patient at substantially the same time.

In another suitable embodiment of a combination therapy, a compound of the invention and a further therapeutic agent may be provided to a patient at different times. The compound of the invention and a further therapeutic agent may be provided to a patient sequentially. For example, the compound of the invention may be provided to the patient prior to provision of the further therapeutic agent. Alternatively a compound of the invention may be provided to the patient after provision of the further therapeutic agent.

"Further Therapeutic Agents"

A compound of the invention may be used in combination with a wide range of further therapeutic agents for the prevention or treatment of cancer. These include biological agents, immunotherapeutic agents, and chemotherapeutic agents that may be used for the prevention or treatment of cancer.

While specific examples of suitable further agents are considered in the following paragraphs, these should not be taken as limiting the range of further therapeutic agents suitable for use with a compound of the invention. Indeed, the ability of a compound of the invention to target cancer stem cells indicates that it may be beneficially used in combination with any further therapeutic agent used in the prevention or treatment of cancer, whether such further agent targets cancer stem cells, non-stem cancer cells, or other cells or constituents involved in the development, maintenance, recurrence, propagation or of cancer.

Examples of further therapeutic agents that may be used in combination with a compound of the invention include:

(a) an anti-angiogenic agent, optionally wherein the anti-angiogenic agent is: (i) an inhibitor of the VEGF pathway, optionally bevacizumab; (ii) a tyrosine kinase inhibitor, optionally sorafenib, sunitinib or pazopanib; or (iii) an mTOR inhibitor, optionally everolimus;
(b) an alkylating agent;
(c) an anti-metabolite;
(d) an anti-tumour antibiotic;
(e) a topoisomerase;
(f) a mitotic inhibitor;
(g) a monoclonal antibody;
(h) a metallic agent; or
(i) an active or passive immunotherapy.

Except for where the context requires otherwise, the further therapeutic agents set out in the preceding list should all be considered suitable for use in any of the embodiments of combination therapies with a compound of the invention considered above.

Selection of Patients

The inventors' finding that a compound of the invention is able to target cancer stem cells makes possible a number of methods by which it is possible to determine whether a particular patient is likely to benefit from receiving a compound of the invention in the prevention or treatment of cancer, such as relapsed or refractory cancer.

Accordingly, the invention provides a method of determining whether a patient with cancer or a pre-cancerous condition will benefit from prevention or treatment of cancer with a compound of the invention, the method comprising: assaying a biological sample representative of cancer or a pre-cancerous condition in the patient for the presence of cancer stem cells; wherein the presence of cancer stem cells in the biological sample indicates that the patient will benefit from treatment with a compound of the invention.

The invention further provides a method of determining a suitable treatment regimen for a patient with cancer or a pre-cancerous condition, the method comprising: assaying a biological sample representative of cancer or a pre-cancerous condition in the patient for the presence of cancer stem cells; wherein the presence of cancer stem cells in the biological sample indicates that a suitable treatment regimen will comprise treatment of the patient with a compound of the invention.

The invention also provides a compound of the invention for use in the prevention or treatment of cancer in a patient selected for such treatment by a method comprising: assaying a biological sample representative of cancer or a pre-cancerous condition in the patient for the presence of cancer stem cells; wherein the presence of cancer stem cells in the biological sample indicates that the patient is suitable for treatment with a compound of the invention.

In suitable embodiments cancer stem cells in a biological sample may be identified by their expression of characteristic patterns of markers discussed previously in the application.

The skilled person will appreciate that there are many suitable examples of biological samples that may be used in embodiments of the invention such as those set out above. Suitably such a sample may include cells from the cancer or pre-cancerous condition. A suitable biological sample may be a tissue sample, such as a sample for use in histology. Cells in such samples may be directly assessed for their expression of cancer stem cell markers, such as those set out above.

Alternatively or additionally, a suitable biological sample may comprise target molecules representative of gene expression by cells of the cancer or pre-cancerous condition. Examples of such target molecules include proteins encoded by the genes expressed, or nucleic acids, such as mRNA, representative of gene expression.

Suitable examples of techniques by which expression of cancer stem cell markers may be assessed may be selected with reference to the sample type. Techniques for the investigation of expressed markers are frequently used in the context of clinical assessments (such as for diagnostic or prognostic purposes) and their use will be familiar to those required to practice them in the context of the present invention. Merely by way of example, in samples containing proteins the presence of cancer stem cell markers may be assessed by suitable techniques using antibodies that react with the cancer stem cell markers in question. Examples of such samples containing protein cancer stem cell markers include histology samples (where the presence of the markers may be visualised by suitable immunocytochemistry techniques), or samples derived from the circulation. Here the presence of circulating cancer stem cells (which are believed to contribute to the propagation of cancer through metastasis) may be assessed using techniques such as flow cytometry.

In samples containing nucleic acids representative of expression of cancer stem cell markers, such expression may be assessed by suitable molecule biology techniques, such as by polymerase chain reaction (PCR) amplification using suitable primers.

Example 1—Synthetic Procedures

Compounds of the invention can be made according to or analogously to the following General Procedures and Exemplary Synthetic Procedures.

General Procedure 1 (for Compounds A-F and L-U)

N-methylimidazole (1.0 mmol) and a solution of the appropriate phosphorochloridate (0.6 mmol) in anhydrous THF (2 mL) were added dropwise to a suspension of 3'-deoxyadenosine (0.20 mmol), or of the substituted 3'-deoxyadenosine, in anhydrous THF (10 mL) and the reaction mixture was stirred at room temperature during a period of 16 hours. Purification by column chromatography and preparative TLC afforded the desired compound as a white solid. Amounts of components employed may vary and actual amounts are given in the examples below.

General Procedure 2 (for Compound J)

3'-Deoxyadenosine (0.80 mmol) was suspended in $(CH_3O)_3PO$ (5 mL), and $POCl_3$ (0.80 mmol) was added dropwise at −5° C. The reaction mixture was allowed to reach room temperature and left stirring for 4 hours. A solution of the appropriate amino acid ester salt (4.0 mmol) dissolved in anhydrous $CH_2Cl_2$ (5 mL) was added followed by diisopropyl ethyl amine (8.0 mmol) at −78° C. After stirring at room temperature for 20 hours, water was added and the layers were separated. The aqueous phase was extracted with dichloromethane and the organic phase washed with brine. The combined organic layers were dried over $Na_2SO_4$ and concentrated. The residue was purified by column chromatography (gradient elution of $CH_2Cl_2$/MeOH=100/0 to 93/7) to give the desired product as a white foam. Amounts of components employed may vary and actual amounts are given in the examples below.

General Procedure 3 (for Compounds G-I)

3'-Deoxyadenosine (0.20 mmol) was suspended in anhydrous THF (5 mL) and $^tBuMgCl$ (1.0 M solution in THF, 0.22 mmol) was added dropwisely at room temperature. A solution of the appropriate phosphorochloridate (0.6 mmol) in anhydrous THF (2 mL) was added dropwisely and the reaction mixture was stirred at room temperature during a period of 16 hours. Purification by column chromatography and preparative TLC afforded the desired compound as a white solid. The amounts of the components employed may vary and actual amounts are given in the examples below.

General Procedure 4 (for Compound V)

TertButyldimethylsilyl chloride (3.3 mol/eq.) and imidazole 6.6 (mol/eq) were added tp a solution of the appropriate 3'-deoxyadenosine derivate (1 mol/eq) in anhydrous DMF and the reaction mixture was stirred at room temperature overnight (16-20 h). Then $NH_4Cl$ was added to the mixture and washed twice with ethylacetate. Organic layers were combined, dried on $Na_2SO_4$ and solvent was removed under vacuum. Purification of the mixture by column chromatography afforded intermediate C1. Intermediate C1 was then dissolved at in an aqueous solution $THF/H_2O/TFA$ 4/1/1 (6 ml/eq) and was stirring at 0° C. for 4 h. The solution was then carefully neutralized with an aqueous saturated solution of $NaHCO_3$ and the mixture was washed twice with ethylacetate. Organic layers were combined, dried on $Na_2SO_4$ and solvent was removed under vacuo. Purification of mixture by column chromatography afforded intermediate C2. Then general procedure B was applied, and intermediate C3 was afforded. Intermediate C3 was dissolved in an aqueous solution of $THF/H_2O/TFA$ 1/1/1 (6 ml/eq) at 0° C. and was stirred at RT for 24 h. Purification by chromatography afforded the desired compounds as white solids.

General Procedure 5 (for Preparing 3'-deoxyadenosine and 3'-deoxy-2-chloroadenosine Employed in the Examples):

A solution of $H_2O/CH_3CN$ 1:9 and then α-AIBBr (4.0 mol/eq) were added sequentially to a suspension of dried adenosine or 2-chloroadenosine in anhydrous $CH_3CN$ and stirring was continued at room temperature (20° C.). After 1 h, a saturated solution of $NaHCO_3$ was added cautiously and the solution was extracted with EtOAc. The combined organic phase was washed with brine. The aqueous phase was extracted with EtOAc and the combined organic phase was dried over $Na_2SO_4$, filtered and evaporated to give a white gum. The crude mixture was dissolved in anhydrous MeOH and stirred for 1 h with Amberlite (2×OH$^-$) resin previously washed well with anhydrous MeOH. The solution was then filtered and the resin carefully washed with anhydrous methanol. Evaporation of the combined filtrate afforded 2',3'-dehydroadenosine or 2',3'-dehydro-2-chloroadenosine as a white solid.

A solution of $LiEt_3BH$ (1M solution in THF 4-4.3 mol/eq) was added dropwise to a cold (4° C.) solution of 2',3'-dehydroadenosine or 2',3'-dehydro-2-chloroadenosine (1 mol/eq) in anhydrous DMSO/THF (1/10) under an argon atmosphere. Stirring was continued at 4° C. for 1 h and at room temperature overnight (16 h). The reaction mixture was carefully acidified (5% $AcOH/H_2O$), purged with $N_2$ for 1 h (under the fume hood) to remove pyrophoric triethylborane, and evaporated. The residue was chromatographed to give 3'-deoxyadenosine or 3'-deoxy-2-chloroadenosine as a white powder.

Using General Procedure 5: 2',3'-dehydroadenosine was prepared from 10.0 g (37.4 mmol) of adenosine, 7.5 mL of $H_2O/CH_3CN$ (1/9), 22 mL (149.7 mmol) of α-AIBBr in 500 mL of anhydrous $CH_3CN$, and 300 mL of Amberlite (2×OH$^-$) resin in 400 mL of dry methanol. 2',3'-dehydroadenosine was obtained as a white solid (9.12 g, 98%). 3'-Deoxyadenosine was prepared from the 9.12 g (36.6 mmol) of 2',3'-dehydroadenosine and 159 mL (159 mmol) of $LiEt_3BH/THF$ 1M, in anhydrous DMSO/THF (1/10, 50 mL). Purification by column chromatography on silica gel (eluent system 3-18% MeOH in DCM) gave 3'-deoxyadenosine as a white powder (7.12 g, 77%).

$^1H$ NMR (500 MHz, DMSO-d6) δ 8.37 (s, 1H, H8), 8.17 (s, 1H, H2), 7.29 (br s, 2H, $NH_2$), 5.89 (d, J=2.5 Hz, 1H, H1'), 5.68 (d, J=4.5 Hz, 1H, OH-2'), 5.19 (t, J=6.0 Hz, 1H, OH-5'), 4.63-4.58 (m, 1H, H2'), 4.40-4.34 (m, 1H, H4'), 3.71 (ddd, J=12.0, 6.0, 3.0 Hz, 1H, H5'), 3.53-3.49 (ddd, J=12.0, 6.0, 4.0 Hz, 1H, H5'), 2.30-2.23 (m, 1H, H3'), 1.98-1.90 (m, 1H, H3'). $^{13}C$ NMR (125 MHz, DMSO-d6) δ 156.00 (C6), 152.41 (C2), 148.82 (C4), 139.09 (C8), 119.06 (C5), 90.79 (C1'), 80.66 (C4'), 74.56 (C2'), 62.61 (C5'), 34.02 (C3').

Using General Procedure 5: 2',3'-dehydro-2-chloroadenosine was prepared from 5.0 g (16.6 mmol) of 2-chloroadenosine, 3.0 mL of $H_2O/CH_3CN$ (1/9), 9.7 mL (66.2 mmol) of α-AIBBr in 38 mL of anhydrous $CH_3CN$, and 150 mL of Amberlite (2×OH$^-$) resin in 200 mL of anhydrous methanol. 2',3'-dehydro-2-chloroadenosine was obtained as a white solid (3.03 g, 60%). 3'-deoxy-2-chloroadenosine was prepared from 2.18 g (7.68 mmol) of 2',3'-dehydro-2-chloroadenosine and 30.7 mL (30.7 mmol) of $LiEt_3BH/THF$ 1M in anhydrous DMSO/THF (1/10 mL, 30 mL). Purification by column chromatography on silica gel (eluent system 2-20% MeOH in DCM) gave 3'-deoxy-2-chloroadenosine as a white powder (1.20 g, 55%).

$^1H$ NMR (500 MHz, $CD_3OD$): δH 8.41 (s, 1H, H8), 5.93 (d, J=2.5 Hz, 1H, H1'), 4.68-4.66 (m, 1H, H2'), 4.56-4.52 (m, 1H, H4'), 3.95 (dd, J=3, 12.5 Hz, 1H, H5'), 3.70 (dd, J=3, 12.5 Hz, 1H, H5'), 2.39-2.33 (m, 1H, H3'), 2.08-2.03 (m, 1H, H3') $^{13}C$ NMR (125 MHz, $CD_3OD$): δC 158.14 (C6), 155.19 (C2), 151.15 (C4), 141.30 (C8), 119.56 (C5), 93.58 (C1'), 82.80 (C4'), 76.81 (C2'), 64.01 (C5'), 34.33 (C3').

Preparation of 3'-deoxy-2-fluoroadenosine

A solution of $H_2O/CH_3CN$ (1:9; 1.4 mL) and then α-AIBBr (4.10 mL, 28.05 mmol) were added sequentially to a suspension of dried 2-fluoroadenosine (2.0 g, 7.01 mmol) in anhydrous $CH_3CN$ (50 mL) and stirring was continued at room temperature (20° C.). After 1 h, saturated solution of $NaHCO_3$ was added cautiously and the solution was extracted with EtOAc (2×100 mL). The combined organic phase was washed with brine (1×50 mL). The aqueous phase was extracted with EtOAc (2×50 mL) and the combined organic phase was dried over $Na_2SO_4$, filtered and evaporated to give a white gum. The crude mixture was dissolved in a mixture of $THF/H_2O$ (4/1, 50 mL) and stirred for 1 h with 60 mL of Amberlite (2×OH$^-$) resin (previously washed well with THF). The solution was then filtered and the resin carefully washed with THF. Evaporation of the combined filtrate and crystallisation of the residue from EtOH gave 2',3'-dehydro-2-fluoroadenosine as a white solid (1.13 g, 60%).

A solution of $LiEt_3BH/THF$ (1M; 18.01 mL, 18.01 mmol) was added dropwise to a cold (4° C., ice bath) solution of 2',3'-dehydro-2-fluoroadenosine (1.13 g, 4.18 mmol) in anhydrous DMSO/THF (1/10, 15 mL) under an argon atmosphere. Stirring was continued at 4° C. for 1 h and at room temperature overnight (16 h). The reaction mixture was carefully acidified (5% AcOH/H$_2$O), purged with N$_2$ for 1 h (under the fume hood) to remove pyrophoric triethylborane, and evaporated. The residue was chromatographed on silica gel (3-18% MeOH in DCM) to give 3'-deoxy-2-fluoroadenosine as a white powder (7.12 g, 77%).

$^{19}$F NMR (470 MHz, DMSO-d6): δF −52.19. $^1$H NMR (500 MHz, DMSO-d6) δH 8.34 (s, 1H, H8), 7.80 (br s, 2H, NH$_2$), 5.78 (d, J=2.25 Hz, 1H, H1'), 5.68 (br s, 1H, OH-2'), 5.01 (br s, 1H, OH-5'), 4.55-4.51 (m, 1H, H2'), 4.39-4.32 (m, 1H, H4'), 3.73-3.76 (m, 1H, H5'), 3.56-3.50 (m, 1H, H5'), 2.26-2.18 (m, 1H, H3'), 1.94-1.85 (m, 1H, H3'). $^{13}$C NMR (125 MHz, DMSO-d6) δC 158.51 (d, $^1J_{C-F}$=202.7 Hz, C2), 157.55 (d, $^3J_{C-F}$=21.2 Hz, C6), 150.11 (d, $^3J_{C-F}$=20.3 Hz, C4), 139.22 (d, $^6J_{C-F}$=2.2 Hz, C8), 117.37 (d, $^4J_{C-F}$=4.1 Hz, C5), 90.67 (C1'), 80.90 (C4'), 74.73 (C2'), 62.35 (C5'), 33.89 (C3').

Preparation of 3'-deoxy-2-methoxyadenosine

A solution of H$_2$O/CH$_3$CN (1:9; 1.4 mL) and then α-AIBBr (4.10 mL, 28.05 mmol) were added sequentially to a suspension of dried 2-fluoroadenosine (2.0 g, 7.01 mmol) in anhydrous CH$_3$CN (50 mL) and stirring was continued at room temperature (20° C.). After 1 h, saturated solution of NaHCO$_3$ was added cautiously and the solution was extracted with EtOAc (2×100 mL). The combined organic phase was washed with brine (1×50 mL). The aqueous phase was extracted with EtOAc (2×50 mL) and the combined organic phase was dried over Na$_2$SO$_4$, filtered and evaporated to give a white gum. The crude mixture was dissolved with anhydrous MeOH (50 mL) and stirred for 1 h with 60 mL of Amberlite (2×OH$^−$) resin (previously washed well with anhydrous MeOH). The solution was then filtered and the resin carefully washed with THF. Evaporation of the combined filtrate and crystallisation of the residue from EtOH gave 2',3'-dehydro-2-methoxyadenosine as a white solid (1.57 g, 84%).

A solution of LiEt$_3$BH (1M solution in THF; 8.53 mL, 8.53 mmol) was added dropwise to a cold (4° C.) solution of 2',3'-dehydro-2-methoxyadenosine (762 mg, 2.84 mmol) in anhydrous DMSO/THF (1/10, 15 mL) under an argon atmosphere. Stirring was continued at 4° C. for 1 h and at room temperature overnight (16 h). The reaction mixture was carefully acidified (5% AcOH/H$_2$O), purged with N$_2$ for 1 h (under the fume hood) to remove pyrophoric triethylborane, and evaporated. The residue was chromatographed on silica gel (3-17% MeOH in DCM) to give 3'-deoxy-2-methoxyadenosine as a white powder (650 mg, 81%).

$^1$H NMR (500 MHz, CD$_3$OD) δH 8.20 (s, 1H, H8), 5.90 (d, J=2.4 Hz, 1H, H1'), 4.75-4.71 (m, 1H, H2'), 4.54-4.48 (m, 1H, H4'), 3.91 (dd, J=12.3, 2.5 Hz, 1H, H5'), 3.69 (dd, J=12.30, 4.0 Hz, 1H, H5'), 3.37 (s, 3H, OCH$_3$), 2.43-2.35 (m, 1H, H3'), 2.08-2.02 (m, 1H, H3'). $^{13}$C NMR (125 MHz, CD$_3$OD) δC 163.68 (C2), 158.12 (C6), 151.94 (C4), 139.71 (C8), 116.64 (C5), 93.36 (C1'), 82.53 (C4'), 76.59 (C2'), 64.24 (C5'), 55.29 (OCH$_3$), 34.81 (C3').

Phosphorochloridates were prepared by published methods from aryl phosphorodichloridates and amino acid ester hydrochlorides.

3'-deoxyadenosine-5'-O-[phenyl(benzyloxy-L-alaninyl)] phosphate A

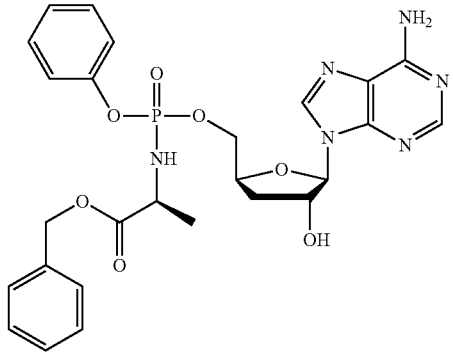 [SMILES: C[C@H](NP(=O)(OC[C@@H]1C[C@H](O)[C@H](n2cnc3c(N)ncnc32)O1)Oc1ccccc1)C(=O)OCc1ccccc1]

Compound A was prepared according to the General Procedure 1 using 3'-deoxyadenosine (50 mg, 0.20 mmol), N-methylimidazole (80 μL, 1.0 mmol) and phenyl(benzyloxy-L-alaninyl) phosphorochloridate (212 mg, 0.6 mmol). Purification by column chromatography (eluent system CH$_3$OH/CH$_2$Cl$_2$ 0/100 to 7/93) with gradient of CH$_2$Cl$_2$/MeOH (100% to 95:5%) and preparative TLC (1000 μm, eluent system CH$_3$OH/CH$_2$Cl$_2$ 5/95) afforded the title compound as a white solid (31 mg, 28%).

$^1$H NMR (500 MHz, CD$_3$OD): δH 8.26 (s, 0.5H, H8), 8.24 (s, 0.5H, H8), 8.22 (s, 0.5H, H2), 8.21 (s, 0.5H, H2), 7.34-7.25 (m, 7H, Ar), 7.21-7.13 (m, 3H, Ar), 6.01 (d, J=2.9 Hz, 1H, H1'), 6.00 (d, J=2.9 Hz, 1H, H1'), 5.15-5.04 (m, 2H, OCH$_2$Ph), 4.73-4.63 (m, 2H, H2', H4'), 4.43-4.35 (m, 1H, H5'), 4.27-4.20 (m, 1H, H5'), 4.03-3.91 (m, 1H, CHCH$_3$), 2.35-2.28 (m, 1H, H3'), 2.09-2.02 (m, 1H, H3'), 1.32 (d, J=7.4 Hz, 1.5H, CHCH$_3$), 1.28 (d, J=7.4 Hz, 1.5H, CHCH$_3$).

$^{13}$C NMR (125 MHz, CD$_3$OD): δC 174.84 (d, $^3J_{C-P}$=4.5 Hz, C=O), 174.63 (d, $^3J_{C-P}$=4.5 Hz, C=O), 157.32 (C6), 157.31 (C6), 153.86 (C2), 153.84 (C2), 152.13 (C4), 152.07 (C4), 150.20 (C—Ar), 150.18 (C—Ar), 140.47 (C8), 137.26 (C—Ar), 137.19 (C—Ar), 130.76 (CH—Ar), 130.74 (CH—Ar), 129.57 (CH—Ar), 129.32 (CH—Ar), 129.31 (CH—Ar), 129.29 (CH—Ar), 129.26 (CH—Ar), 126.16 (CH—Ar), 126.14 (CH—Ar), 121.46 (d, $^3J_{C-P}$=4.7 Hz, CH—Ar), 121.38 (d, $^3J_{C-P}$=4.7 Hz, CH—Ar) 120.54 (C5), 120.53 (C5), 93.24 (C1'), 93.18 (C1'), 80.43 (d, $^3J_{C-P}$=3.6 Hz, C4'), 80.36 (d, $^3J_{C-P}$=3.6 Hz, C4'), 76.62 (C2'), 68.62 (d, $^2J_{C-P}$=5.3 Hz, C5'), 68.30 (d, $^2J_{C-P}$=5.3 Hz, C5'), 67.95 (OCH$_2$Ph), 67.92 (OCH$_2$Ph), 51.74 (CHCH$_3$), 51.60 (CHCH$_3$), 34.91 (C3'), 34.70 (C3'), 20.45 (d, $^3J_{C-P}$=7.0 Hz, CHCH$_3$), 20.28 (d, $^3J_{C-P}$=7.0 Hz, CHCH$_3$).

$^{31}$P NMR (202 MHz, CD$_3$OD): δP 3.9, 3.7.

MS (ES+) m/z: Found: 569.2 (M+H$^+$), 591.2 (M+Na$^+$), 1159.4 (2M+Na$^+$) C$_{26}$H$_{29}$N$_6$O$_7$P required: (M) 568.2.

HPLC Reverse-phase HPLC eluting with H$_2$O/CH$_3$CN from 100/10 to 0/100 in 30 minutes, 1 ml/min, l=254 nm, showed two peaks of the diastereoisomers with tR 14.02 min. and tR 14.26 min.

(2S)-benzyl 2-(((((2S,4R,5R)-5-(6-amino-9H-purin-9-yl)-4-hydroxytetrahydrofuran-2-yl)methoxy)(naphthalen-1-yloxy)phosphoryl)amino)propanoate B

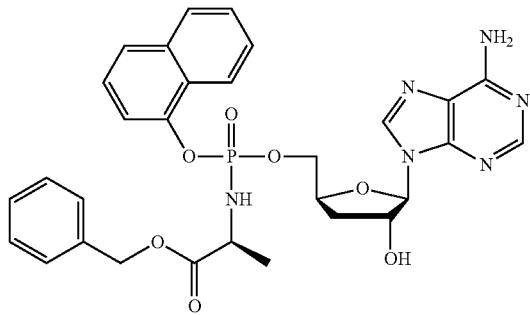 [SMILES: C[C@H](NP(=O)(OC[C@@H]1C[C@H](O)[C@H](n2cnc3c(N)ncnc32)O1)Oc1cccc2ccccc12)C(=O)OCc1ccccc1]

Using General Procedure 1 above, N-methylimidazole (240 µL, 3.0 mmol) and a solution of (2S)-benzyl 2-((chloro(naphthalen-1-yloxy)phosphoryl)amino)propanoate (727 mg, 1.8 mmol) in anhydrous THF (10 mL) were added dropwisely to a suspension of 3'-deoxyadenosine (150 mg, 0.6 mmol) in anhydrous THF and the reaction mixture was stirred at room temperature during a period of 16 hours. Purification by column chromatography (eluent system $CH_3OH/CH_2Cl_2$ 0/100 to 6/94) and preparative TLC (2000 µM, eluent system $CH_3OH/CH_2Cl_2$ 5/95) afforded the desired compound as white solid (45 mg, 12%).

MS (ES+) m/z: Found: 619.2 (M+H$^+$), 641.2 (M+Na$^+$), 1259.4 (2M+Na$^+$) $C_{30}H_{31}N_6O_7P$ required: (M) 618.58.

$^{31}$P NMR (202 MHz, $CH_3OD$): δP 4.3 (s), 4.1 (s).

$^1$H NMR (500 MHz, $CH_3OD$): δH 8.24 (s, 0.5H, H8), 8.22 (s, 0.5H, H8), 8.20 (s, 0.5H, H2), 8.19 (s, 0.5H, H2), 8.14-8.09 (m, 1H, Ar), 7.89-7.85 (m, 1H, Ar), 7.70-7.67 (m, 1H, Ar), 7.53-7.42 (m, 3H, Ar), 7.39-7.34 (m, 1H, Ar), 7.31-7.25 (m, 5H, Ar), 5.99 (d, J=2.0 Hz, 0.5H, H1'), 5.98 (d, J=2.0 Hz, 0.5H, H1'), 5.10-5.01 (m, 2H, $CH_2Ph$), 4.72-4.61 (m, 2H, H2', H4'), 4.47-4.40 (m, 1H, H5'), 4.33-4.24 (m, 1H, H5'), 4.09-3.98 (m, 1H, CH ala) 2.35-2.26 (m, 1H, H3'), 2.07-1.98 (m, 1H, H3'), 1.30-1.24 (m, 3H, $CH_3$).

$^{13}$C NMR (125 MHz, $CH_3OD$): δC 174.85 (d, $^3J_{C-P}$=3.7 Hz, C=O), 174.56 (d, $^3J_{C-P}$=3.7 Hz, C=O), 157.33 (C6), 157.31 (C6), 153.87 (C2), 153.85 (C2), 150.24 (C4), 150.23 (C4), 147.91 (d, $^3J_{C-P}$=7.5 Hz, 'ipso' Nap), 147.95, (d, $^3J_{C-P}$=7.5 Hz, 'ipso' Nap), 140.56 (C8), 140.50 (C8), 137.22 (C—Ar), 137.17 (C—Ar), 136.28 (C—Ar), 129.55 (CH—Ar), 129.53 (CH—Ar), 129.30 (CH—Ar), 129.25 (CH—Ar), 128.88 (CH—Ar), 128.82 (CH—Ar), 127.91 (d, $^2J_{C-P}$=6.25 Hz, C—Ar), 127.83 (d, $^2J_{C-P}$=6.25 Hz, C—Ar), 127.77 (CH—Ar), 127.75 (CH—Ar), 127.49 (CH—Ar), 127.45 (CH—Ar), 126.48 (CH—Ar), 126.47 (CH—Ar), 126.02 (CH—Ar), 125.97 (CH—Ar), 122.77 (CH—Ar), 122.63 (CH—Ar), 120.58 (C5), 120.53 (C5), 116.35 (d, $^3J_{C-P}$=3.75 Hz, CH—Ar), 116.15 (d, $^3J_{C-P}$=3.75 Hz, CH—Ar), 93.22 (C1'), 93.20 (C1'), 80.30 (d, $^3J_{C-P}$=2.75 Hz, C4'), 80.24 (d, $^3J_{C-P}$=2.75 Hz, C4'), 76.51 (C2'), 76.44 (C2'), 68.87 (d, $^2J_{C-P}$=5.2 Hz, C5'), 68.64 (d, $^2J_{C-P}$=5.2 Hz, C5'), 67.93 ($OCH_2Ph$), 51.82 (CH ala), 51.73 (CH ala), 35.01 (C-3'), 34.76 (C3'), 20.41 (d, $^3J_{C-P}$=6.7 Hz, $CH_3$ ala), 20.22 (d, $^3J_{C-P}$=6.7, $CH_3$ ala).

HPLC Reverse-phase HPLC eluting with $H_2O/CH_3CN$ from 100/10 to 0/100 in 30 minutes, 1 ml/min, 1=200 nm, showed two peaks of the diastereoisomers with tR 16.36 min. and tR 16.60 min.

Benzyl 2-(((((2S,4R,5R)-5-(6-amino-9H-purin-9-yl)-4-hydroxytetrahydrofuran-2-yl)methoxy)(phenoxy)phosphoryl)amino)acetate C

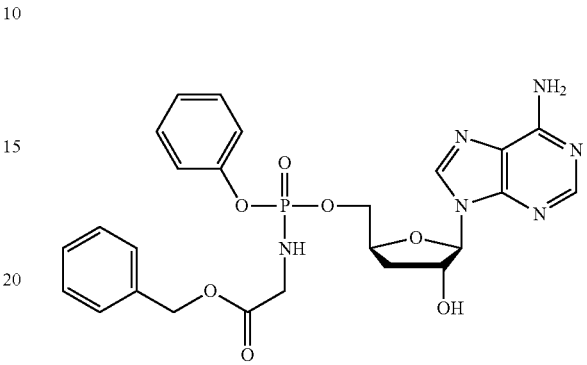

Using General Procedure 1 above, N-methylimidazole (80 µL, 1.0 mmol) and a solution of benzyl 2-((chloro(phenoxy)phosphoryl)amino)acetate (204 mg, 0.6 mmol) in anhydrous THF (2 mL) were added dropwisely to a suspension of 3'-deoxyadenosine (50 mg, 0.20 mmol) in anhydrous THF and the reaction mixture was stirred at room temperature for 16 hours. Purification by column chromatography (eluent system $CH_3OH/CH_2Cl_2$ 0/100 to 6/94) and preparative TLC (500 µM, eluent system $CH_3OH/CH_2Cl_2$ 5/95) afforded the desired compound as a white solid (21 mg, 19%).

(ES+) m/z, found: 555.2 (M+H$^+$), 577.2 (M+Na$^+$), 1131.4 (2M+Na$^+$). $C_{25}H_{27}N_6O_7P$ required: (M) 554.2.

$^{31}$P NMR (202 MHz, $CH_3OD$) δ 5.1, 4.9.

$^1$H NMR (500 MHz, $CH_3OD$) δ 8.27 (s, 0.5H, H8), 8.24 (s, 0.5H, H8), 8.22 (s, 0.5H, H2), 8.21 (s, 0.5H, H2), 7.37-7.26 (m, 7H, Ph), 7.22-7.13 (m, 3H, Ph), 6.02 (d, J=1.8 Hz, 0.5H, H1'), 6.00 (d, J=1.8 Hz, 0.5H, H1'), 5.14-5.11 (m, 2H, $OCH_2Ph$), 4.73-4.64 (m, 2H, H2', H4'), 4.50-4.39 (m, 1H, H5'), 4.36-4.24 (m, 1H, H5'), 3.53-3.71 (m, 2H, $CH_2$ gly), 2.39-2.25 (m, 1H, H3'), 2.13- 2.02 (m, 1H, H3').

$^{13}$C NMR (125 MHz, $CH_3OD$) δ 172.30 (d, $^3J_{C-P}$=5.0 Hz, C=O), 172.27 (d, $^3J_{C-P}$=5.0 Hz, C=O), 157.34 (C6), 157.32 (C6), 153.88 (C2), 153.87 (C2), 152.08 (d, $^3J_{C-P}$=7.5 Hz, C—Ar), 152.05 (d, $^3J_{C-P}$=7.5 Hz, C—Ar), 150.20 (C4), 150.19 (C4), 140.52 (C8), 140.42 (C8), 137.15 (C—Ar), 130.79 (CH—Ar), 129.57 (CH—Ar), 129.55 (CH—Ar), 129.35 (CH—Ar), 129.34 (CH—Ar), 129.33 (CH—Ar), 126.22 (CH—Ar), 121.44 (d, $J_{C-P}$=3.7 Hz, CH—Ar), 121.40 (d, $J_{C-P}$=3.7 Hz, CH—Ar), 120.51 (C5), 120.49 (C5), 93.19, 93.14 (C1'), 80.46 (d, $^3J_{C-P}$=4.60 Hz, C4'), 80.39 (d, $^3J_{C-P}$=4.60, C4'), 76.66 (C2'), 68.68 (d, $^2J_{C-P}$=5.42 Hz, C5'), 68.24 (d, $^2J_{C-P}$=5.42 Hz, C5'), 67.95 ($OCH_2Ph$), 67.93 ($OCH_2Ph$), 43.90 ($CH_2$ gly), 43.83 ($CH_2$ gly), 34.83 (C3'), 34.54 (C3').

HPLC Reverse-phase HPLC eluting with $H_2O/CH_3CN$ from 100/10 to 0/100 in 30 minutes, 1 ml/min, 1=200 nm, showed two peaks of the diastereoisomers with tR 13.63 min. and tR 13.41 min.

(2S)-pentyl 2-(((((2S,4R,5R)-5-(6-amino-9H-purin-9-yl)-4-hydroxytetrahydrofuran-2-yl)methoxy)(naphthalen-1-yloxy)phosphoryl)amino)-4-methyl-pentanoate D

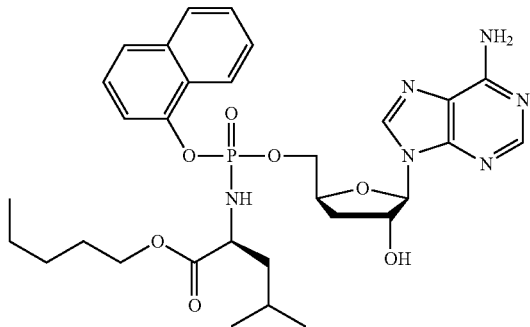 [SMILES: CCCCCOC(=O)[C@H](CC(C)C)NP(=O)(OC[C@@H]1C[C@H](O)[C@H](n2cnc3c(N)ncnc32)O1)Oc1cccc2ccccc12]

Using General Procedure 1 above, N-methylimidazole (76 μL, 0.95 mmol) and a solution of (2S)-pentyl 2-((chloro(naphthalen-1-yloxy)phosphoryl)amino)-4-methylpentanoate (250 mg, 0.6 mmol) in anhydrous THF (1 mL) were added dropwisely to a suspension of 3'-deoxyadenosine (48 mg, 19 mmol) in anhydrous THF (5 mL) and the reaction mixture was stirred at room temperature during a period of 16 hours. Purification by column chromatography (eluent system $CH_3OH/CH_2Cl_2$ 0/100 to 5/95) and preparative TLC (1000 μM, eluent system $CH_3OH/CH_2Cl_2$ 4/96) afforded the desired compound as a white solid (27 mg, 22%).

MS (ES+) m/z: Found: 641.3 (M+H$^+$), 663.3 (M+Na$^+$), 1303.6 (2M+Na$^+$) $C_{31}H_{41}N_6O_7P$ required: (M) 640.3.

$^{31}$P NMR (202 MHz, $CH_3OD$) δ 4.64, 4.37.

$^1$H NMR (500 MHz, $CH_3OD$) δ 8.28 (s, 0.5H, H-8), 8.25 (s, 0.5H, H-8), 8.21 (s, 0.5H, H-2), 8.20 (s, 0.5H, H-2), 8.17-8.12 (m, 1H, Nap), 7.88-7.83 (m, 1H, Nap), 7.69-7.66 (m, 1H, Nap), 7.54-7.42 (m, 3H, Nap), 7.40-7.35 (m, 1H, Nap), 7.31-7.26 (m, 5H, Ar), 6.01 (d, J=2.1 Hz, 0.5H, H1'), 6.00 (d, J=2.1 Hz, 0.5H, H1'), 4.47-4.67 (m, 2H, H2', H4'), 4.55-4.44 (m, 1H, H5'), 4.43-4.31 (m, 1H, H5'), 4.00-3.87 (m, 3H, CH leu, $CH_2$ Pen), 2.44-2.30 (m, 1H, H3'), 2.14-2.04 (m, 1H, H3'), 1.66-1.39 (m, 5H, $CH_2$CH leu, $CH_2$ Pen), 1.1.28-1.21 (m, 4H, $CH_2CH_2$ Pen), 0.86-0.81 (m, 3H, $CH_3$ Pen), 0.81-0.68 (m, δH, $(CH_3)_2$ leu).

$^{13}$C NMR (125 MHz, $CH_3OD$) δ 175.42 (d, $^3J_{C-P}$=2.5 Hz, C=O), 175.04 (d, $^3J_{C-P}$=2.5 Hz, C=O), 157.32 (C6), 153.87 (C2), 153.86 (C2), 150.23 (C4), 147.97 (d, $^3J_{C-P}$=6.2 Hz, 'ipso' Nap), 140.55 (C8), 136.30 (C—Ar), 136.29 (C—Ar), 128.89 (CH—Ar), 128.84 (CH—Ar), 127.95 (C—Ar), 127.91 (C—Ar), 127.84 (C—Ar), 127.78 (CH—Ar), 127.76 (CH—Ar), 127.46 (CH—Ar), 126.50 (C—Ar), 126.48 (C—Ar), 126.46 (C—Ar), 126.01 (CH—Ar), 125.91 (CH—Ar), 122.80 (CH—Ar), 122.70 (CH—Ar), 120.58 (C5), 120.56 (C5), 116.40 (d, $^3J_{C-P}$=3.7 Hz, CH—Ar), 116.01 (d, $^3J_{C-P}$=3.7 Hz, CH—Ar), 93.31 (C1'), 93.27 (C1'), 80.35 (d, $^3J_{C-P}$=3.5 Hz, C4'), 80.29 (d, $^3J_{C-P}$=3.5 Hz, C4'), 76.54 (C2'), 76.50 (C2'), 69.07 (d, $^2J_{C-P}$=5.5 Hz, C5'), 68.85 (d, $^2J_{C-P}$=5.5 Hz, C5'), 66.33 ($CH_2$ Pent), 66.32 ($CH_2$ Pent), 54.81 (CH leu), 54.71 (CH leu), 44.22 (d, $^3J_{C-P}$=7.6 Hz, $CH_2$ leu), 43.93 (d, $^3J_{C-P}$=7.6 Hz, $CH_2$ leu), 35.15 (C3'), 34.86 (C3'), 29.32 ($CH_2$ pent), 29.30 ($CH_2$ Pent), 29.11 ($CH_2$ pent), 25.67 (CH leu), 25.45 (CH leu), 23.30 ($CH_2$ pent), 23.12 ($CH_3$ leu), 23.02 ($CH_3$ leu), 22.04 ($CH_3$ leu), 21.78 ($CH_3$ leu), 14.28 ($CH_3$ pent).

HPLC Reverse-phase HPLC eluting with $H_2O/CH_3CN$ from 100/10 to 0/100 in 30 minutes, 1 ml/min, 1=200 nm, showed one peak of the two overlapping diastereoisomers with tR 20.84 min.

Methyl 2-(((((2S,4R,5R)-5-(6-amino-9H-purin-9-yl)-4-hydroxytetrahydrofuran-2-yl)-methoxy)(naphthalen-1-yloxy)phosphoryl)amino)-2-methylpropanoate E

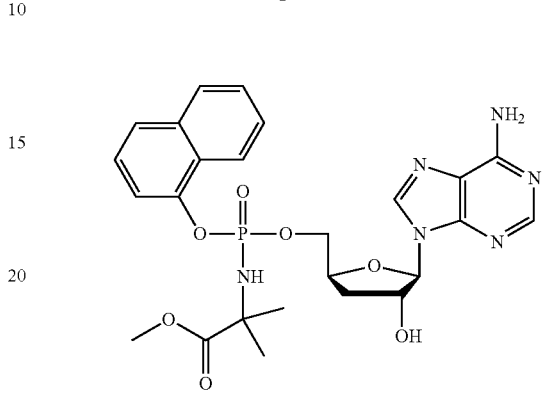

Using General Procedure 1 above, N-methylimidazole (24 μL, 3.0 mmol) and a solution of methyl 2-((chloro(naphthalen-1-yloxy)phosphoryl)amino)-2-methylpropanoate (612 mg, 1.8 mmol) in anhydrous THF (1 mL) were added dropwisely to a suspension of 3'-deoxyadenosine (150 mg, 0.6 mmol) in anhydrous THF (15 mL) and the reaction mixture was stirred at room temperature during a period of 16 hours. Purification by column chromatography (eluent system $CH_3OH/CH_2Cl_2$ 0/100 to 7/93) and preparative TLC (1000 μM, eluent system $CH_3OH/CH_2Cl_2$ 4/96) afforded the desired compound as a white solid (20 mg, 6%).

MS (ES+) m/z: Found: 557.2 (M+H$^+$), 579.2 (M+Na$^+$), 1135.4 (2M+Na$^+$) $C_{25}H_{29}N_6O_7P$ required: (M) 556.51.

$^{31}$P NMR (202 MHz, $CH_3OD$) δ 2.73.

$^1$H NMR (500 MHz, $CH_3OD$) δ 8.28 (s, 0.5H, H8), 8.25 (s, 0.5H, H8), 8.21 (s, 0.5H, H2), 8.19 (s, 0.5H, H2), 8.18-8.14 (m, 1H, Nap), 7.90-7.84 (m, 1H, Nap), 7.71-7.66 (m, 1H, Nap), 7.53-7.47 (m, 3H, Nap), 7.41-7.35 (m, 1H, Nap), 6.03 (d, J=2.1 Hz, 0.5H, H1'), 5.99 (d, J=2.1 Hz, 0.5H, H1'), 4.76-4.67 (m, 2H, H2', H4'), 4.52-4.44 (m, 1H, H5'), 4.42-4.33 (m, 1H, H5'), 3.65 (s, 1.5H, $OCH_3$), 3.64 (s, 1.5H, $OCH_3$), 2.48-2.41 (m, 0.5H, H3'), 2.37-2.30 (m, 0.5H, H3'), 2.15-2.09 (m, 0.5H, H3'), 2.08-2.02 (m, 0.5H, H3'), 1.47-1.44 (m, 6H, $CH_3$).

$^{13}$C NMR (125 MHz, $CH_3OD$) δ 177.25 (d, $^3J_{C-P}$=3.7 Hz, C=O), 157.53 (C6), 157.51 (C6), 153.86 (C2), 150.28 (C4), 150.25 (C4), 148.06 (d, $^3J_{C-P}$=7.5 Hz, 'ipso' Nap), 148.04 (d, $^3J_{C-P}$=7.5 Hz, 'ipso' Nap), 140.67 (C8), 140.60 (C8), 136.28 (C—Ar), 136.27 (C—Ar), 128.82 (CH—Ar), 128.80 (CH—Ar), 127.93 (d, $^2J_{C-P}$=6.25 Hz, C—Ar), 127.92 (d, $^2J_{C-P}$=6.25 Hz, C—Ar), 127.71 (CH—Ar), 127.69 (CH—Ar), 127.32 (CH—Ar), 126.44 (CH—Ar), 125.84 (CH—Ar), 122.93 (CH—Ar), 120.56 (C5), 120.50 (C5), 116.38 (d, $^3J_{C-P}$=3.75 Hz, CH—Ar), 116.36 (d, $^3J_{C-P}$=3.75 Hz, CH—Ar), 93.25 (C1'), 80.40 (d, $^3J_{C-P}$=8.0 Hz, C4'), 80.33 (d, $^3J_{C-P}$=8.0 Hz, C4'), 76.57 (C2'), 76.43 (C2'), 68.99 (d, $^2J_{C-P}$=5.5 Hz, C5'), 68.84 (d, $^2J_{C-P}$=5.5 Hz, C5'), 53.01 ($OCH_3$), 35.22 (C-3'), 34.90 (C3'), 27.85 (d, $^3J_{C-P}$=6.0 Hz, $CH_3$), 27.80 (d, $^3J_{C-P}$=6.0, $CH_3$), 27.60 (d, $^3J_{C-P}$=6.0, $CH_3$), 27.56 (d, $^3J_{C-P}$=6.0, $CH_3$).

HPLC Reverse-phase HPLC eluting with H$_2$O/CH$_3$CN from 100/10 to 0/100 in 30 minutes, 1 ml/min, 1=254 nm, showed two peaks with tR 16.51 min, tR 16.75 min.

(2S)-benzyl 2-(((((2S,4R,5R)-5-(6-amino-9H-purin-9-yl)-4-hydroxytetrahydrofuran-2-yl)methoxy)(2-(3-ethoxy-3-oxopropyl)phenoxy)phosphoryl)amino)propanoate F

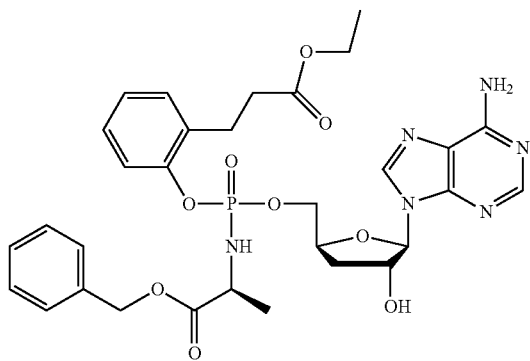 [SMILES: CCOC(=O)CCc1ccccc1OP(=O)(N[C@@H](C)C(=O)OCc1ccccc1)OC[C@@H]1C[C@H](O)[C@H](n2cnc3c(N)ncnc32)O1]

Using General Procedure 1 above, N-methylimidazole (32 µL, 4.2 mmol) and a solution of (2S)-benzyl 2-((chloro(2-(3-ethoxy-3-oxopropyl)phenoxy)phosphoryl)amino)propanoate (1.14 g, 2.5 mmol) in anhydrous THF (2 mL) were added dropwisely to a suspension of 3'-deoxyadenosine (210 mg, 0.84 mmol) in anhydrous THF (10 mL) and the reaction mixture was stirred at room temperature during a period of 16 hours. Purification by column chromatography (eluent system CH$_3$OH/CHCl$_3$ 0/100 to 8/92) and preparative TLC (1000 µM, eluent system CH$_3$OH/CH$_2$Cl$_2$ 5/95) afforded the desired compound as a white solid (123 mg, yield=22%).

MS (ES+) m/z: Found: 669.3 (M+H$^+$), 691.3 (M+Na$^+$), C$_{31}$H$_{37}$N$_6$O$_9$P required: (M) 668.63.

$^{31}$P NMR (202 MHz, CH$_3$OD): δP 3.95, 3.65.

$^1$H NMR (500 MHz, CH$_3$OD): δH 8.25 (s, 0.5H, H8), 8.21 (s, 1H, H8, H2), 8.20 (s, 0.5H, H2), 7.35-7.29 (m, 6H, Ph), 7.25-7.21 (m, 1H, Ph), 7.16-7.07 (m, 2H, Ar), 6.00 (d, J=1.9 Hz, 0.5H, H1'), 5.98 (d, J=1.9 Hz, 0.5H, H1'), 5.17-5.05 (m, 2H, OCH$_2$Ph), 4.76-4.73 (m, 0.5H, H2'), 4.70-4.59 (m, 1.5H, H2', H4'), 4.45-4.34 (m, 1H, H5'), 4.30-4.22 (m, 1H, H5'), 4.08-3.96 (m, 3H, CH$_2$CH$_3$, CH ala), 2.98-2.92 (m, 2H, CH$_2$CH$_2$), 2.62-2.56 (m, 2H, CH$_2$CH$_2$), 2.40-2.29 (m, 1H, H3'), 2.11-2.03 (m, 1H, H3'), 1.36 (d, J=6.9 Hz, 1.5H, CH$_3$ ala), 1.33 (d, J=6.9 Hz, 1.5H, CH$_3$ ala), 1.17 (t, J=7.0 Hz, 1.5H, CH$_2$CH$_3$), 1.16 (t, J=7.0 Hz, 1.5H, CH$_2$CH$_3$).

$^{13}$C NMR (125 MHz, CH$_3$OD): δC 174.82 (d, $^3$J$_{C-P}$=3.7 Hz, C=O), 174.62 (C=O), 174.58 (C=O), 174.55 (d, $^3$J$_{C-P}$=3.7 Hz, C=O), 157.34 (C6), 157.32 (C6), 153.86 (C2), 153.84 (C2), 150.48 (d, J$_{C-P}$=2.5 Hz, C—Ar), 150.44 (C4), 150.22 (d, J$_{C-P}$=2.5 Hz, C—Ar), 140.49 (C8), 137.29 (C—Ar), 137.21 (C—Ar), 133.09 (d, J=7.5 Hz, C—Ar), 132.94 (d, J=7.5 Hz, C—Ar), 131.62 (CH—Ar), 131.59 (CH—Ar), 129.58 (CH—Ar), 129.34 (CH—Ar), 129.31 (CH—Ar), 129.28 (CH—Ar), 128.70 (d, J=5.0 Hz, CH—Ar), 128.69 (d, J=5.0 Hz, CH—Ar), 126.18 (CH—Ar), 121.02 (d, J=2.5 Hz, CH—Ar), 120.49 (d, J=2.5 Hz, CH—Ar), 120.58 (C5), 93.28 (C1'), 93.24 (C1'), 80.32 (d, $^3$J$_{C-P}$=8.7 Hz, C4'), 76.57 (C2'), 68.86 (d, $^2$J$_{C-P}$=5.0 Hz, C5'), 68.53 (d, $^2$J$_{C-P}$=5.0 Hz, C5'), 67.98 (OCH$_2$Ph), 67.95 (OCH$_2$Ph), 61.57 (CH$_2$CH$_3$), 51.76 (CH ala), 51.65 (CH ala), 35.37 (CH$_2$CH$_2$), 35.30 (CH$_2$CH$_2$), 35.08 (C3'), 34.85 (C3'), 26.77 (CH$_2$CH$_2$), 26.72 (CH$_2$CH$_2$), 20.55 (d, $^3$J$_{C-P}$=6.2 Hz, CH$_3$ ala), 20.33 (d, $^3$J$_{C-P}$=6.2 Hz, CH$_3$ ala), 14.53 (CH$_2$CH$_3$).

HPLC Reverse-phase HPLC eluting with H$_2$O/CH$_3$CN from 100/10 to 0/100 in 30 minutes, 1 ml/min, 1=245 nm, showed one peak with tR 15.99 min.

(2S)-benzyl 2-(((((2R,3R,5S)-2-(6-amino-9H-purin-9-yl)-5-(hydroxymethyl)tetrahydrofuran-3-yl)oxy)(phenoxy)phosphoryl)amino)propanoate G

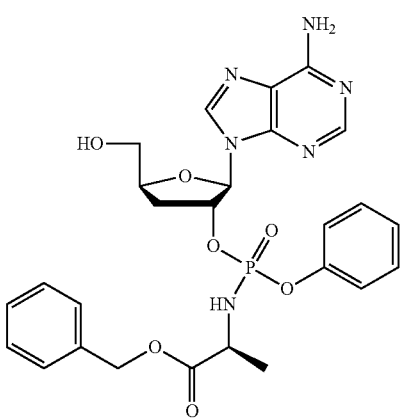 [SMILES: C[C@H](NP(=O)(Oc1ccccc1)O[C@H]1C[C@@H](CO)O[C@H]1n1cnc2c(N)ncnc21)C(=O)OCc1ccccc1]

Using General Procedure 3 above, 3'-deoxyadenosine (50 mg, 0.20 mmol) was suspended in anhydrous THF (5 mL) and $^t$BuMgCl (1.0 M solution in THF, 0.22 mL, 0.22 mmol) was added dropwisely at room temperature. A solution of (2S)-benzyl 2-((chloro(phenoxy)phosphoryl)amino)propanoate (212 mg, 0.6 mmol) in anhydrous THF (2 mL) was added dropwisely and the reaction mixture was stirred at room temperature during a period of 16 hours. Purification by column chromatography (eluent system CH$_3$OH/CH$_2$C$_2$ 0/100 to 8/92) and preparative TLC (500 µM, eluent system CH$_3$OH/CH$_2$C$_2$=5/95) afforded the desired compound as a white solid (6 mg, 5%).

MS (ES+) m/z: Found: 569.2 (M+H$^+$), 591.2 (M+Na$^+$), 1159.4 (2M+Na$^+$) C$_{26}$H$_{29}$N$_6$O$_7$P required: (M) 568.2.

$^{31}$P NMR (202 MHz, CH$_3$OD): δP 2.44 (s), 2.92 (s).

$^1$H NMR (500 MHz, CH$_3$OD): δH 8.41 (s, 0.5H, H8), 8.28 (s, 0.5H, H8), 8.19 (s, 0.5H, H2), 8.18 (s, 0.5H, H2), 7.39-7.30 (m, 4H, Ar), 7.28-7.18 (m, 4H, Ar), 7.17-7.11 (m, 1H, Ar), 7.08-7.03 (m, 1H, Ar), 6.23 (d, J=2.0 Hz, 0.5H, H1'), 6.08 (d, J=3.4 Hz, 0.5H, H1'), 5.52-5.43 (m, 1H, C2'), 5.19-5.12 (m, 1H, CH$_2$Ph), 5.07-4.95 (m, 1H, CH$_2$Ph), 4.48-4.42 (m, 1H, H4'), 4.05-3.97 (m, 1H, CH ala), 3.95-3.87 (m, 1H, H5'), 3.69-3.61 (m, 1H, H5'), 2.59-2.45 (m, 1H, H3'), 2.31-2.23 (m, 1H, H3'), 1.36-1.27 (m, 3H, CH$_3$ ala).

$^{13}$C NMR (125 MHz, CH$_3$OH): δC 174.76 (d, $^3$J$_{C-P}$=5.0 Hz, C=O), 174.52 (d, $^3$J$_{C-P}$=5.0 Hz, C=O), 157.44 (C6), 153.76 (C2), 151.93 (C4), 150.06 (C—Ar), 149.93 (C—Ar), 141.38 (C8), 141.18 (C8), 137.33 (C—Ar), 137.10 (C—Ar), 130.69 (CH—Ar), 130.79 (CH—Ar), 129.61 (CH—Ar), 129.51 (CH—Ar), 129.40 (CH—Ar), 129.30 (CH—Ar), 129.23 (CH—Ar), 126.33 (CH—Ar), 126.16 (CH—Ar), 121.53 (d, $^3$J$_{C-P}$=4.5 Hz, CH—Ar), 121.20 (d, $^3$J$_{C-P}$=4.5H, CH—Ar), 120.76 (C5), 91.56 (d, $^3$J$_{C-P}$=7.7 Hz, C1'), 91.45 (d, $^3$J$_{C-P}$=7.7 Hz, C1'), 82.78 (C4'), 82.28 (C4'), 81.83 (d, $^2$J$_{C-P}$=4.7 Hz, C2'), 80.96 (2×d, $^2$J$_{C-P}$=4.7 Hz, C2'), 67.95 (OCH$_2$Ph), 67.92 (OCH$_2$Ph), 64.13 (C5'), 63.59 (C5'), 51.88

(CH ala), 51.75 (CH ala), 33.75 (d, $^3J_{C\text{-}P}$=3.0 Hz, C3'), 33.59 (d, $^3J_{C\text{-}P}$=3.0 Hz, C3'), 20.33 (d, $^3J_{C\text{-}P}$=7.1 CH₃ ala), 20.18 (d, $^3J_{C\text{-}P}$=7.1 CH₃ ala).

HPLC Reverse-phase HPLC eluting with H₂O/CH₃OH from 90/10 to 0/100 in 30 minutes, 1 ml/min, 1=254 nm, showed two peaks of the diastereoisomers with tR 22.16 min. and tR 22.43 min.

Benzyl 2-(((((2S,4R,5R)-5-(6-amino-9H-purin-9-yl)-4-((((1-(benzyloxy)-1-oxopropan-2-yl)amino)(phenoxy)phosphoryl)oxy)tetrahydrofuran-2-yl)methoxy)(phenoxy)phosphoryl)-amino)propanoate H

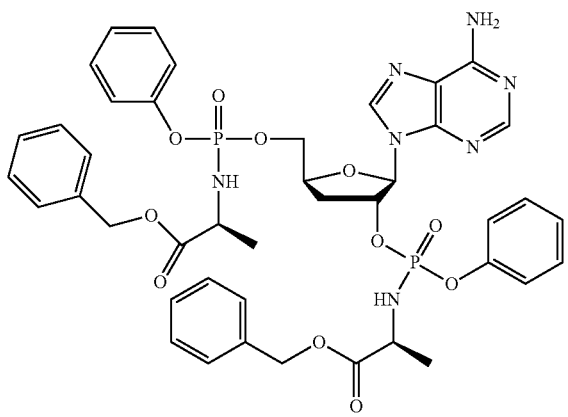 [SMILES: C[C@H](NP(=O)(OC[C@@H]1C[C@H](OP(=O)(N[C@@H](C)C(=O)OCc2ccccc2)Oc2ccccc2)[C@H](n2cnc3c(N)ncnc32)O1)Oc1ccccc1)C(=O)OCc1ccccc1]

Using General Procedure 3 above, 3'-deoxyadenosine (50 mg, 0.20 mmol) was suspended in anhydrous THF (5 mL) and $^t$BuMgCl (1.0 M solution in THF, 0.22 mL, 0.22 mmol) was added dropwisely at room temperature. A solution of (2S)-benzyl 2-((chloro(phenoxy)phosphoryl)amino)propanoate (212 mg, 0.6 mmol) in anhydrous THF (2 mL) was added dropwisely and the reaction mixture was stirred at room temperature during a period of 16 hours. Purification by column chromatography (eluent system CH₃OH/CH₂Cl₂ 0/100 to 8/92) and preparative TLC (500 μM, eluent system CH₃OH/CH₂Cl₂ 5/95) afforded the desired compound as a white solid (19 mg, yield=11%).

MS (ES+) m/z, found: 886.3 (M+H⁺), 1771.6 (2M+H⁺), 751.2 (molecule without nucleobase M). C₄₂H₄₅N₇O₁₁P₂ required: (M+) 885.3.

$^{31}$P NMR (202 MHz, CH₃OD): δP 3.98, 3.88, 3.59, 3.12, 3.05, 2.45, 2.32.

$^1$H NMR (500 MHz, CH₃OD): δH 8.24-8.13 (m, 2H, H8, H2), 7.39-7.08 (m, 20H, Ph), 6.27-6.23 (m, 0.5H, H1'), 6.16-6.13 (m, 0.5H, H1'), 5.61-5.48 (m, 1H, H2'), 5.17-4.91 (m, 4H, CH₂Ph), 4.57-4.49 (m, 1H, H4'), 4.41-4.29 (m, 1H, H5'), 4.25-4.15 (m, 1H, H5'), 4.10-4.01 (m, 1H, CH ala), 3.99-3.89 (m, 1H, CH ala), 2.57-2.41 (m, 1H, H3'), 2.28-2.17 (m, 1H, H3'), 1.38-1.23 (m, 6H, CH₃ ala).

$^{13}$C NMR (125 MHz, CH₃OD): δC 174.88 (C=O), 174.83 (C=O), 174.79 (C=O), 174.73 (C=O), 174.61 (C=O), 174.57 (C=O), 174.53 (C=O), 157.36 (C6), 157.34 (C6), 157.32 (C6), 157.29 (C6), 154.04 (C2), 154.01 (C2), 153.97 (C2), 153.94 (C2), 152.09 (C4), 152.04 (C4), 152.02 (C4), 151.97 (C4), 150.31 (C—Ar), 150.29 (C—Ar), 150.16 (C—Ar), 140.98 (C8), 140.91 (C8), 140.81 (C8), 137.31 (C—Ar), 137.28 (C—Ar), 137.22 (C—Ar), 137.09 (C—Ar), 130.86 (CH—Ar), 130.78 (CH—Ar), 130.77 (CH—Ar), 129.65 (CH—Ar), 129.61 (CH—Ar), 129.58 (CH—Ar), 129.55 (CH—Ar), 129.44 (CH—Ar), 129.42 (CH—Ar), 129.38 (CH—Ar), 129.34 (CH—Ar), 129.32 (CH—Ar), 129.30 (CH—Ar), 129.28 (CH—Ar), 129.23 (CH—Ar), 129.21 (CH—Ar), 12.42 (CH—Ar), 126.23 (CH—Ar), 126.20 (CH—Ar), 126.17 (CH—Ar), 121.65 (CH—Ar), 121.63 (CH—Ar), 121.61 (CH—Ar), 121.59 (CH—Ar), 121.52 (CH—Ar), 121.51 (CH—Ar), 121.50 (CH—Ar), 121.47 (CH—Ar), 121.46 (CH—Ar), 121.40 (CH—Ar), 121.39 (CH—Ar), 121.36 (CH—Ar), 121.35 (CH—Ar), 121.30 (CH—Ar), 121.28 (CH—Ar), 121.26 (CH—Ar), 121.24 (CH—Ar), 120.61 (C5), 120.57 (C5), 120.56 (C5), 120.54 (C5), 91.56 (C1'), 91.51 (C1'), 91.45 (C1'), 91.25 (C1'), 91.20 (C1'), 81.84 (C2'), 81.82 (C2'), 81.79 (C2'), 81.27 (C2'), 81.22 (C2'), 81.18 (C2'), 80.49 (C4'), 80.43 (C4'), 80.06 (C4'), 79.99 (C4'), 68.29 (C5', OCH₂Ph), 68.25 (C5', OCH₂Ph), 68.00 (C5', OCH₂Ph), 67.96 (C5', OCH₂Ph), 67.94 (C5', OCH₂Ph), 67.90 (C5', OCH₂Ph), 67.71 (C5', OCH₂Ph), 67.67 (C5', OCH₂Ph), 51.91 (CH ala), 51.74 (CH ala), 51.70 (CH ala), 51.59 (CH ala), 34.22 (C3'), 34.20 (C3'), 34.16 (C3'), 33.97 (C3'), 33.94 (C3'), 33.91 (C3'), 20.44 (CH₃ ala), 20.43 (CH₃ ala), 20.39 (CH₃ ala), 20.29 (CH₃ ala), 20.27 (CH₃ ala), 20.24 (CH₃ ala), 20.21 (CH₃ ala), 20.19 (CH₃ ala).

HPLC Reverse-phase HPLC eluting with H₂O/CH₃CN from 100/10 to 0/100 in 30 minutes, 1 ml/min, 1=254 nm, showed one broad peak with tR 15.97 min.

(2S)-benzyl 2-(((((2R,3R,5S)-2-(6-amino-9H-purin-9-yl)-5-(hydroxymethyl)tetrahydrofuran-3-yl)oxy)(naphthalen-1-yloxy)phosphoryl)amino)propanoate I

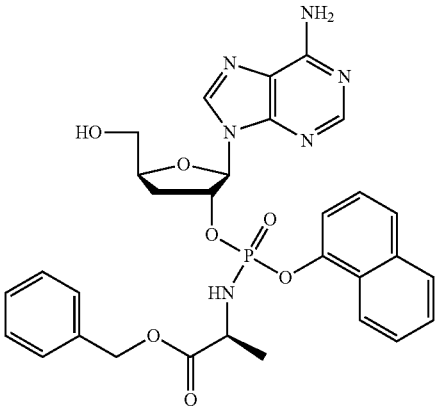 [SMILES: C[C@H](NP(=O)(Oc1cccc2ccccc12)O[C@H]1C[C@@H](CO)O[C@H]1n1cnc2c(N)ncnc21)C(=O)OCc1ccccc1]

Using General Procedure 3 above, 3'-Deoxyadenosine (50 mg, 0.20 mmol) was suspended in anhydrous THF (5 mL) and $^t$BuMgCl (1.0 M solution in THF, 0.3 mL, 0.3 mmol) was added dropwisely at room temperature. A solution of (2S)-benzyl 2-((chloro(naphthalen-1-yloxy)phosphoryl)amino)propanoate (323 mg, 0.8 mmol) in anhydrous THF (2 mL) was added dropwisely and the reaction mixture was stirred at room temperature during a period of 16 hours. Purification by column chromatography (eluent system CH₃OH/CH₂Cl₂ 0/100 to 6/94) and preparative TLC (500 μM, eluent system CH₃OH/CH₂Cl₂ 5/95) afforded the desired compound as a white solid (14 mg, 11%).

(ES+) m/z, found: 619.2 (M+H⁺), 641.2 (M+Na⁺), 1259.4 (2M+Na⁺). C₃₀H₃₁N₆O₇P required: (M) 618.20.

$^{31}$P NMR (202 MHz, CH₃OD): δP 3.27 (s), 2.75 (s).

$^1$H NMR (500 MHz, CH₃OD): δH 8.37 (s, 1H, H8), 8.18 (s, 1H, H8), 8.14 (s, 1H, H2), 8.13-8.11 (m, 0.5H, Nap) 8.11 (s, 1H, H2), 7.94-7.90 (m, 0.5H, Ar), 7.90-7.87 (m, 0.5H,

Ar), 7.86-7.82 (m, 0.5H, Ar), 7.74-7.70 (m, 0.5H, Ar), 7.66-7.61 (m, 0.5H, Ar), 7.57-7.47 (m, 1.5H, Ar), 7.46-7.37 (m, 2.5H, Ar), 7.34-7.27 (m, 4H, Ar), 7.25-7.17 (m, 1H, Ar), 6.19 (d, J=2.4 Hz, 0.5H, H1'), 6.04 (d, J=2.4 Hz, 0.5H, H1'), 5.60-5.54 (m, 0.5H, H2'), 5.50-5.42 (m, 0.5H, H2'), 5.16-4.99 (m, 2H, OCH$_2$Ph), 4.46-4.40 (m, 0.5H, H4'), 4.36-4.30 (m, 0.5H, H4'), 4.13-4.04 (m, 1H, CH ala), 3.90-3.83 (m, 1H, H5'), 3.64-3.56 (m, 1H, H5'), 2.61-2.54 (m, 0.5H, H3'), 2.49-2.41 (m, 0.5H, H3'), 2.35-2.27 (m, 0.5H, H3'), 2.22-2.16 (m, 0.5H, H3'), 1.35-1.24 (m, 3H, CH$_3$ ala).

$^{13}$C NMR (125 MHz, CH$_3$OH): δC 174.52 (C=O), 174.49 (C=O), 157.27 (C6), 153.58 (C2), 149.97 (C4), 149.93 (C-4), 147.70 (d, $^3J_{C-P}$=7.5, 'ipso' Nap), 147.48 (d, $^3J_{C-P}$=7.5, 'ipso' Nap), 141.36 (C8), 141.19 (C8), 137.25 (C—Ar), 137.05 (C—Ar), 136.31 (C—Ar), 136.20 (C—Ar), 129.58 (CH—Ar), 129.48 (CH—Ar), 129.37 (CH—Ar), 129.26 (CH—Ar), 129.22 (CH—Ar), 128.88 (CH—Ar), 127.84 (CH—Ar), 127.75 (CH—Ar), 127.49 (CH—Ar), 127.44 (CH—Ar), 126.48 (CH—Ar), 126.39 (CH—Ar), 126.26 (CH—Ar), 126.05 (CH—Ar), 122.76 (CH—Ar), 122.38 (CH—Ar), 120.68 (C5), 120.61 (C5), 116.64 (d, $^3J_{C-P}$=3.75 Hz, CH—Ar), 116.13 (d, $^3J_{C-P}$=3.75 Hz, CH—Ar), 91.60 (d, $^3J_{C-P}$=7.5 Hz, C1'), 91.43 (d, $^3J_{C-P}$=7.5 Hz, C1'), 82.74 (C4'), 82.27 (C4'), 81.99 (d, $^2J_{C-P}$=5.5 Hz, C2'), 81.12 (d, $^2J_{C-P}$=5.5 Hz, C2'), 67.97 (OCH$_2$Ph), 67.94 (OCH$_2$Ph), 64.16 (C5'), 63.51 (C5'), 51.96 (CH ala), 51.89 (CH ala), 33.89 (d, $^3J_{C-P}$=7.5 Hz, CH$_3$ ala), 33.63 (d, $^3J_{C-P}$=7.5 Hz, CH$_3$ ala).

HPLC Reverse-phase HPLC eluting with H$_2$O/CH$_3$OH from 100/10 to 0/100 in 30 minutes, 1 ml/min, 1=200 nm, showed two peaks of the diastereoisomers with tR 24.84 min. and tR 25.43 min.

Benzyl 2-[({[5-(6-amino-9H-purin-9-yl)-4-hydroxyoxolan-2-yl]methoxy}({[1-(benzyloxy)-1-oxopropan-2-yl]amino})phosphoryl)amino]propanoate J

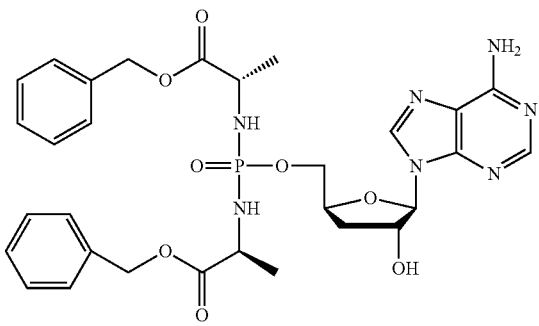 [SMILES: C[C@H](NP(=O)(N[C@@H](C)C(=O)OCc1ccccc1)OC[C@@H]1C[C@H](O)[C@H](n2cnc3c(N)ncnc32)O1)C(=O)OCc1ccccc1]

Using General Procedure 2 above, 3'-deoxyadenosine (200 mg, 0.80 mmol) was suspended in (CH$_3$)$_3$PO$_3$ (5 mL), and POCl$_3$ (75 μL, 0.80 mmol) was added dropwise at −5° C. The reaction mixture was allowed to reach room temperature and left stirring for 4 hours. A solution of (S)-1-(benzyloxy)-1-oxopropan-2-aminium 4-methylbenzenesulfonate (1.4 g, 4.0 mmol) dissolved in anhydrous CH$_2$Cl$_2$ (5 mL) was added followed by diisopropyl ethyl amine (1.4 mL, 8.0 mmol) at −78° C. After stirring at room temperature for 20 hours, water was added and the layers were separated. The aqueous phase was extracted with dichloromethane and the organic phase washed with brine. The combined organic layers were dried over Na$_2$SO$_4$ and concentrated. The residue was purified by column chromatography (gradient elution of CH$_2$Cl$_2$/MeOH=100/0 to 93/7) to give a white foam (256 mg, 49%).

MS (ES+) m/z: Found: 654.2 (M+H$^+$), 676.2 (M+Na$^+$), 1329.5 (2M+Na$^+$) C$_{30}$H$_{36}$N$_7$O$_8$P required: (M) 653.62.

$^{31}$P NMR (202 MHz, CH$_3$OD) S 13.9.

$^1$H NMR (500 MHz, CH$_3$OD) δ 8.28 (s, 1H, H8), 8.22 (s, 1H, H2), 7.37-7.26 (m, 10H, Ph), 6.00 (d, J=1.9 Hz, 1H, H1'), 5.15-5.05 (m, 4H, OCH$_2$Ph), 4.74-4.70 (m, 1H, H2'), 4.63-4.56 (m, 1H, H4'), 4.24-4.18 (m, 1H, H5'), 4.11-4.05 (m, 1H, H5'), 3.97-3.87 (m, 1H, CH ala), 2.35-2.27 (m, 1H, H3'), 2.07-2.01 (m, 1H, H3'), 1.34-1.27 (m, 3H, CH$_3$ ala).

$^{13}$C NMR (125 MHz, CH$_3$OD) δ 175.40 (d, $^3J_{C-P}$=5.0 Hz, C=O), 175.36 (d, $^3J_{C-P}$=5.0 Hz, C=O), 157.36 (C6), 153.91 (C2), 150.25 (C4), 140.64 (C8), 137.33 (C—Ar), 137.29 (C—Ar), 129.58 (CH—Ar), 129.57 (CH—Ar), 129.33 (CH—Ar), 129.31 (CH—Ar), 129.29 (CH—Ar), 120.55 (C5), 93.18 (C1'), 80.67 (d, $^3J_{C-P}$=8.4 Hz, C4'), 76.59 (C2'), 67.90 (OCH$_2$Ph), 67.47 (d, $^2J_{C-P}$=5.2 Hz, C5'), 51.14 (d, $^2J_{C-P}$=1.7 Hz, CH ala), 51.11 (d, $^2J_{C-P}$=1.7 Hz, CH ala), 35.08 (C3'), 20.77 (d, $^3J_{C-P}$=6.5 Hz, CH$_3$ ala), 20.59 (d, $^3J_{C-P}$=6.5 Hz, CH$_3$ ala).

HPLC Reverse-phase HPLC eluting with H$_2$O/CH$_3$CN from 90/10 to 0/100 in 30 minutes, 1 ml/min, 1=254 nm, showed one peak with tR 13.87 min.

(2S)-benzyl 2-((((2S,4R,5R)-5-(6-amino-2-methoxy-9H-purin-9-yl)-4-hydroxytetrahydrofuran-2-yl)methoxy)(naphthalen-1-yloxy)phosphorylamino)propanoate K

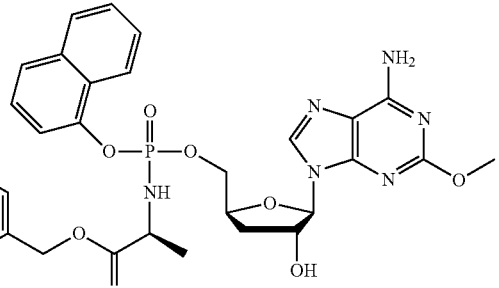

Using General Procedure 1 above, N-methylimidazole (99 μL, 1.24 mmol) and a solution of (2S)-benzyl 2-((chloro(naphthalen-1-yloxy)phosphoryl)amino)propanoate (303 mg, 0.75 mmol) in anhydrous THF (5 mL) were added dropwisely to a suspension of 2-O-methyl-3'-deoxyadenosine (70 mg, 0.25 mmol) in anhydrous THF (10 mL) and the reaction mixture was stirred at room temperature during a period of 16 hours. Purification by column chromatography (eluent system CH$_3$OH/CH$_2$Cl$_2$ 0/100 to 6/94) and preparative TLC (eluent system CH$_3$OH/CH$_2$Cl$_2$ 5/95) afforded the desired compound as white solid (96 mg, 60%).

MS (ES+) m/z: Found: 649.2 (M+H$^+$) C$_{31}$H$_{33}$N$_6$O$_8$P required: 648.21 (M). $^{31}$P NMR (202 MHz, CD$_3$OD): δP 4.38 (s), 4.08 (s). $^1$H NMR (500 MHz, CD$_3$OD): δH 8.14-8.11 (d, J=8.0 Hz, 0.5H, Ar), 8.07 (d, J=8.0 Hz, 0.5H, Ar), 8.05 (s, 0.5H, H8), 8.02 (s, 0.5H, H8), 7.82-7.80 (m, 1H, Ar), 7.61 (d, J=7.0 Hz, Ar), 7.47-7.44 (m, 4H, Ar), 7.35-7.29 (m, 2H, Ar), 7.24-7.22 (m, 3H, Ar), 5.88 (s, 1H, H1'), 4.71-4.68 (m, 1H, H4'), 4.65-6.60 (m, 1H, H2'), 4.42-4.40 (m, 1H, H5'), 4.30-4.27 (m, 1H, H5'), 4.08-3.98 (m, 1H, CH ala) 3.88 (s, 1.5H, OCH$_3$), 3.86 (s, 1.5H, OCH$_3$), 2.37-2.33

(m, 1H, H3'), 2.04-2.01 (m, 1H, H3'), 1.27 (d J=7.0 Hz, 1.5H, CH₃), 1.24 (d J=7.0 Hz, 1.5H, CH₃). $^{13}$C NMR (125 MHz, CH₃OD): δC 174.83 (d, $^3J_{C-P}$=3.7 Hz, C=O), 174.60 (d, $^3J_{C-P}$=3.7 Hz, C=O), 163.70 (C-2), 158.10 (C6), 151.95 (C4), 147.95 (d, $^3J_{C-P}$=7.5 Hz, 'ipso' Nap), 147.91, (d, $^3J_{C-P}$=7.5 Hz, 'ipso' Nap), 139.39 (C8), 139.37 (C8), 137.12, 137.17 (C-ipso CH₂Ph), 136.22 (C—Ar), 129.57, 129.54, 129.48, 129.32, 129.27, 129.12, 129.24 128.89, 128.83, (CH—Ar), 127.85 (d, $^2J_{C-P}$=6.25 Hz, C—Ar), 127.86, 127.76, 127.51, 127.48, 126.49, 126.00, 125.97, 122.73, 122.63 (CH—Ar), 116.86 (C5), 116.72 (C5), 116.29 (d, $^3J_{C-P}$=3.75 Hz, CH—Ar), 116.22 (d, $^3J_{C-P}$=3.75 Hz, CH—Ar), 93.33 (C1'), 93.31 (C1'), 80.24 (d, $^3J_{C-P}$=2.75 Hz, C4'), 76.29 (C2'), 76.26 (C2'), 69.09 (d, $^2J_{C-P}$=5.0 Hz, C5'), 68.16 (d, $^2J_{C-P}$=8.2 Hz, C5'), 67.95 (OCH₂Ph), 55.28, 55.32 (OCH₃), 51.79 (CH ala), 51.71 (CH ala), 35.40 (C-3'), 35.12 (C3'), 20.49 (d, $^3J_{C-P}$=6.7 Hz, CH₃ ala), 20.35 (d, $^3J_{C-P}$=6.7, CH₃ ala). HPLC Reverse-phase HPLC eluting with H₂O/CH₃CN from 100/10 to 0/100 in 30 minutes, F=1 ml/min, λ=280 nm, showed two peaks of the diastereoisomers with tR 16.22 min. and $t_R$ 16.48 min.

(2S)-benzyl 2-((((2S,4R,5R)-5-(6-amino-2-methoxy-9H-purin-9-yl)-4-hydroxytetrahydrofuran-2-yl)methoxy)(naphthalen-1-yloxy)phosphorylamino)propanoate L

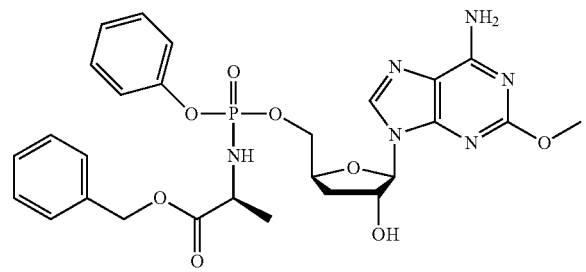 [SMILES: COc1nc(N)c2ncn([C@@H]3O[C@H](COP(=O)(N[C@@H](C)C(=O)OCc4ccccc4)Oc4ccccc4)C[C@@H]3O)c2n1]

Using General Procedure 1 above, N-methylimidazole (99 μL, 1.24 mmol) and a solution of (2S)-benzyl 2-((chloro(phenoxy)phosphoryl)amino)propanoate (264 mg, 0.75 mmol) in anhydrous THF (2 mL) were added dropwisely to a suspension of 2-O-methyl-3'-deoxyadenosine (70 mg, 0.25 mmol) in anhydrous THF and the reaction mixture was stirred at room temperature for 16 hours. Purification by column chromatography (eluent system CH₃OH/CH₂Cl₂ 0/100 to 6/94) and preparative TLC (eluent system CH₃OH/CH₂Cl₂ 5/95) afforded the desired compound as a white solid (13 mg, 10%).

(ES+) m/z, found: 599.2 (M+H⁺), C₂₇H31N₆O₈P required: 598.19 (M).
$^{31}$P NMR (202 MHz, CD₃OD) δ 3.97, 3.64. $^1$H NMR (500 MHz, CD₃OD) δ 8.06 (s, 0.5H, H8), 8.04 (s, 0.5H, H8), 7.33-7.28 (m, 7H, Ph), 7.20-7.14 (m, 3H, Ph), 5.92 (d, J=1.5 Hz, 0.5H, H1'), 5.90 (d, J=1.5 Hz, 0.5H, H1'), 5.14-5.04 (m, 2H, OCH₂Ph), 4.78-4.76 (m, 0.5H, H4'), 4.74-4.72 (m, 0.5H, H4'), 4.63-4.59 (m, 1H, H2'), 4.10-4.34 (m, 1H, H5'a), 4.25-4.20 (m, 1H, H5'b), 3.94, 3.95 (OCH₃), 3.99-3.90 (m, 1H, CH ala), 2.40-2.37 (m, 1H, H3'), 2.07-2.04 (m, 1H, H3'), 1.31 (d J=7.0 Hz, CH₃), 1.26 (d, J=7.0 Hz, CH₃). $^{13}$C NMR (125 MHz, CD₃OD) δ 174.82 (d, $^3J_{C-P}$=3.7 Hz, C=O), 174.62 (d, $^3J_{C-P}$=3.7 Hz, C=O), 163.80 (C-2), 158.16, 158.13 (C6), 152.15 (C4), 152.05 (d, $^3J_{C-P}$=4.8 Hz, C-ipso Ph), 152.00 (d, $^3J_{C-P}$=4.8 Hz, C-ipso Ph), 139.39 (C8), 137.30, 137.21 (C-ipso CH₂Ph), 130.72, 129.57, 129.31, 129.27, 126.122 (CH—Ar), 121.42 (d, $J_{C-P}$=4.5 Hz, CH—Ar), 121.37 (d, $J_{C-P}$=4.5 Hz, CH—Ar), 116.72 (C5), 116.69 (C5), 93.33, 93.24 (C1'), 80.26 (d, $^3J_{C-P}$=8.87, C4'), 80.19 (d, $^3J_{C-P}$=8.87, C4'), 76.35 (C2'), 68.78 (d, $^2J_{C-P}$=5.0 Hz, C5'), 68.35 (d, $^2J_{C-P}$=5.0 Hz, C5'), 67.94 (OCH₂Ph), 67.92 (OCH₂Ph), 55.25, 55.28 (OCH₃), 51.69, 51.57 (CH ala), 35.23 (C3'), 34.96 (C3'), 20.38 (d, $^3J_{C-P}$=6.7, CH₃ ala), 20.26 (d, $^3J_{C-P}$=6.7, CH₃ ala). HPLC Reverse-phase HPLC eluting with H₂O/CH₃CN from 100/10 to 0/100 in 30 minutes, F=1 ml/min, λ=280 nm, showed two peaks of the diastereoisomers with $t_R$14.22 min. and $t_R$ 14.51 min.

2-O-methyl-3'-deoxyadenosine-5'-O-[1-naphthyl(1-pentyloxy-L-leucinyl)] phosphate M

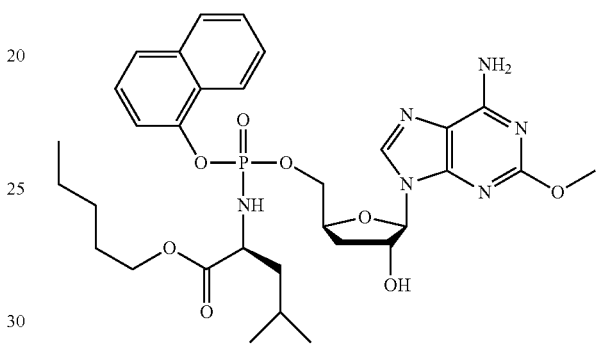

Compound M was prepared according to the general procedure 1 using 2-O-methyl-3'-deoxyadenosine (70 mg, 0.25 mmol), N-methylimidazole (99 μL, 1.24 mmol) and naphthyl(pentyloxy-L-leucinyl) phosphorochloridate (330 mg, 0.75 mmol). Purification by column chromatography (eluent system gradient CH₃OH/CH₂Cl₂ 0/100 to 6/94) and preparative TLC (2000 μM, eluent system CH₃OH/CH₂Cl₂ 7/93) afforded the title compound as a white solid (50 mg, 30%).

$^{31}$P NMR (202 MHz, CD₃OD) δP 4.53, 4.28.
$^1$H NMR (500 MHz, CD₃OD) δH 8.04-7.96 (m, 1H, H8), 7.77-7.71 (m, 1H, Nap), 7.58-7.53 (m, 1H, Nap), 7.45-7.17 (m, 5H, Nap), 5.83-5.75 (m, 1H, H1'), 4.64-4.51 (m, 2H, H2', H4'), 4.40-4.16 (m, 2H, H5'), 3.88-3.75 (m, δH, OCH₃, O(CH₂)₄CH₃, CHCH₂CH(CH₃)₂), 2.38-2.24 (m, 1H, H3'), 2.00-1.91 (m, 1H, H3'), 1.53-1.05 (m, 11H, O(CH₂)₄CH₃, CHCH₂CH(CH₃)₂), 0.77-0.55 (m, 9H, O(CH₂)₄CH₃, CHCH₂CH(CH₃)₂).
$^{13}$C NMR (125 MHz, CD₃OD) δC 175.02 (d, $^3J_{C-P}$=2.5 Hz, C=O), 174.78 (d, $^3J_{C-P}$=2.5 Hz, C=O), 163.76 (C2), 158.14 (C6), 151.03 (C4), 147.96 (d, $^3J_{C-P}$=7.2, 'ipso' Nap), 138.96 (C8), 136.30 (C—Ar), 136.28 (C—Ar), 136.22 (C—Ar), 128.93 (CH—Ar), 128.88 (CH—Ar), 128.81 (CH—Ar), 128.48 (CH—Ar), 127.77 (CH—Ar), 127.73 (CH—Ar), 127.44 (CH—Ar), 127.42 (CH—Ar), 127.06 (CH—Ar), 126.86 (CH—Ar), 126.45 (CH—Ar), 126.44 (CH—Ar), 126.31 (CH—Ar), 125.98 (CH—Ar), 125.88 (CH—Ar), 123.83 (CH—Ar), 123.43 (CH—Ar), 123.24 (CH—Ar), 122.81 (CH—Ar), 122.77 (CH—Ar), 122.69 (CH—Ar), 116.34 (d, $^3J_{C-P}$=3.7 Hz, CH—Ar), 116.02 (d, $^3J_{C-P}$=3.7 Hz, CH—Ar), 115.71 (C5), 93.42 (C1'), 93.32 (C1'), 80.22 (d, $^3J_{C-P}$=5.3 Hz, C4'), 80.15 (d, $^3J_{C-P}$=5.3 Hz, C4'), 76.29 (C2'), 76.27 (C2'), 69.22 (d, $^2J_{C-P}$=5.2 Hz, C5'), 69.028 (d, $^2J_{C-P}$=5.2 Hz, C5'), 66.31 (O(CH₂)₄CH₃), 66.30 (O(CH₂)₄CH₃), 55.29 (OCH₃), 55.24 (OCH₃), 54.79

(CHCH$_2$CH(CH$_3$)$_2$), 54.68 (CHCH$_2$CH(CH$_3$)$_2$), 44.20 (d, $^3J_{C-P}$=7.25 Hz, CHCH$_2$CH(CH$_3$)$_2$), 43.93 (d, $^3J_{C-P}$=7.25 Hz, CHCH$_2$CH(CH$_3$)$_2$), 35.49 (C3'), 35.17 (C3'), 29.31 (O(CH$_2$)$_4$CH$_3$), 29.11 (O(CH$_2$)$_4$CH$_3$), 25.67 (CHCH$_2$CH(CH$_3$)$_2$), 25.44 (CHCH$_2$CH(CH$_3$)$_2$), 23.30 (O(CH$_2$)$_4$CH$_3$), 23.10 (CHCH$_2$CH(CH$_3$)$_2$), 23.00 (CHCH$_2$CH(CH$_3$)$_2$), 22.94 (CHCH$_2$CH(CH$_3$)$_2$), 22.81 (CHCH$_2$CH(CH$_3$)$_2$), 14.27 (O(CH$_2$)$_4$CH$_3$).

(ES+) m/z, found: 671.3 (M+H$^+$), C$_{32}$H$_{43}$N$_6$O$_8$P required: 670.69 (M).

HPLC Reverse-phase HPLC eluting with H$_2$O/CH$_3$CN from 100/10 to 0/100 in 30 minutes, 1 ml/min, 1=254 nm, showed two peaks of the diastereoisomers with tR 20.83 min. and tR 20.93 min.

2-O-methyl-3'-deoxyadenosine-5'-O-[phenyl(1-hexyloxy-L-alaninyl)] phosphate N

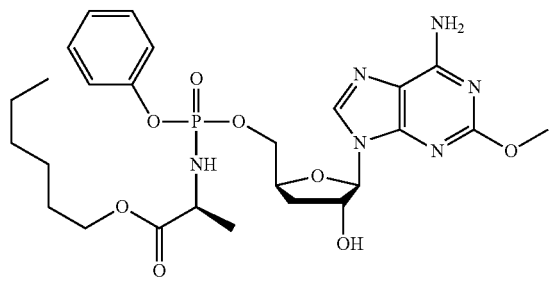 [SMILES: CCCCCCOC(=O)[C@H](C)NP(=O)(OC[C@@H]1C[C@H](O)[C@H](n2cnc3c(N)nc(OC)nc32)O1)Oc1ccccc1]

Compound N was prepared according to the general procedure 1 using 2-O-methyl-3'-deoxyadenosine (70 mg, 0.25 mmol), N-methylimidazole (99 µL, 1.24 mmol) and phenyl(hexyloxy-L-alaninyl) phosphorochloridate (261 mg, 0.75 mmol). Purification by column chromatography (eluent system gradient CH$_3$OH/CH$_2$Cl$_2$ 0/100 to 6/94) and preparative TLC (1000 µM, eluent system CH$_3$OH/CH$_2$Cl$_2$ 7/93) afforded the title compound as a white solid (26 mg, 18%).

$^{31}$P NMR (202 MHz, CD$_3$OD) δP 3.87, 3.65.

1H NMR (500 MHz, CD$_3$OD) δH 8.08 (s, 0.5H, H8), 8.07 (s, 0.5H, H8), 7.36-7.29 (m, 2H, Ph), 7.24-7.14 (m, 3H, Ph), 5.94 (d, J=2.0 Hz, 0.5H, H1'), 5.92 (d, J=2.0 Hz, 0.5H, H1'), 4.81-4.76 (m, 1H, H2'), 4.71-4.62 (m, 1H, H4'), 4.48-4.43 (m, 0.5H, H5'), 4.42-4.36 (m, 0.5H, H5'), 4.33-4.25 (m, 1H, H5'), 4.10-3.83 (m, 8H, OCH$_3$, O(CH$_2$)$_5$CH$_3$, CHCH$_3$), 2.48-2.40 (m, 1H, H3'), 2.13-2.07 (m, 1H, H3'), 1.61-1.51 (m, 2H, O(CH$_2$)$_5$CH$_3$), 1.33-1.24 (m, 9H, O(CH$_2$)$_5$CH$_3$, CHCH$_3$), 0.89 (m, 3H, O(CH$_2$)$_5$CH$_3$).

$^{13}$C NMR (125 MHz, CD$_3$OD) δC 175.13 (d, $^3J_{C-P}$=4.3 Hz, C=O), 174.94 (d, $^3J_{C-P}$=4.3 Hz, C=O), 163.80 (C2), 163.78 (C2), 158.17 (C6), 158.15 (C6), 152.17 (d, $^2J_{C-P}$=6.3 Hz, C—Ar), 152.15 (d, $^2J_{C-P}$=6.3 Hz, C—Ar), 152.03 (C4), 151.99 (C4), 139.42 (C8), 139.39 (C8), 130.75 (CH—Ar), 130.74 (CH—Ar), 126.13 (CH—Ar), 121.43 (CH—Ar), 121.41 (CH—Ar), 121.39 (CH—Ar), 121.37 (CH—Ar), 116.74 (C5), 116.69 (C5), 93.40 (C1'), 93.27 (C1'), 80.30 (C4'), 80.23 (C4'), 76.40 (C2'), 68.85 (d, $^2J_{C-P}$=5.2 Hz, C5'), 68.42 (d, $^2J_{C-P}$=5.2 Hz, C5'), 66.43 (O(CH$_2$)$_5$CH$_3$), 55.30 (OCH$_3$), 55.26 (OCH$_3$), 51.64 (CHCH$_3$), 51.54 (CHCH$_3$), 35.30 (C3'), 35.04 (C3'), 32.58 (O(CH$_2$)$_5$CH$_3$), 29.67 (O(CH$_2$)$_5$CH$_3$), 29.64 (O(CH$_2$)$_5$CH$_3$), 26.61 (O(CH$_2$)$_5$CH$_3$), 23.59 (O(CH$_2$)$_5$CH$_3$), 20.56 (d, $^3J_{C-P}$=6.4 Hz, CHCH$_3$), 20.41 (d, $^3J_{C-P}$=6.4 Hz, CHCH$_3$), 14.36 (O(CH$_2$)$_5$CH$_3$).

(ES+) m/z, found: 593.3 (M+H$^+$), C$_{32}$H$_{43}$N$_6$O$_8$P required: 592.58 (M).

HPLC Reverse-phase HPLC eluting with H$_2$O/CH$_3$CN from 100/10 to 0/100 in 30 minutes, 1 ml/min, 1=254 nm, showed two peaks of the diastereoisomers with tR 17.02 min. and tR 17.23 min.

2-Fluoro-3'-deoxyadenosine-5'-O-[1-naphthyl(benzyloxy-L-alaninyl)] phosphate O

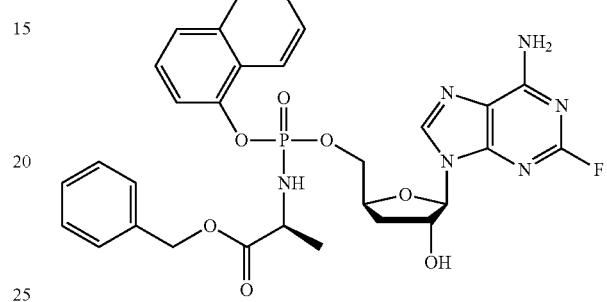

Compound O was prepared according to the general procedure 1 using 2-Fluoro-3'-deoxyadenosine (50 mg, 0.18 mmol), N-methylimidazole (74 µL, 0.93 mmol) and phenyl (benzyloxy-L-alaninyl) phosphorochloridate (196 mg, 0.56 mmol). Purification by column chromatography (eluent system gradient CH$_3$OH/CH$_2$Cl$_2$ 0/100 to 6/94) and preparative TLC (500 µM, eluent system CH$_3$OH/CH$_2$Cl$_2$ 5/95) afforded the title compound as a white solid (5 mg, 4%).

$^{31}$P NMR (202 MHz, CD$_3$OD) δP 4.33, 4.08.

$^1$H NMR (500 MHz, CD$_3$OD) δH 8.17 (s, 0.5H, H8), 8.14 (s, 0.5H, H8), 8.14-8.09 (m, 1H, Ar), 7.89-7.85 (m, 1H, Ar), 7.70-7.66 (m, 1H, Ar), 7.54-7.42 (m, 4H, Ar), 7.40-7.24 (m, 5H, Ar), 5.89 (d, J=2.3 Hz, 0.5H, H1'), 5.88 (d, J=2.3 Hz, 0.5H, H1'), 5.08-5.01 (m, 2H, OCH$_2$Ph), 4.70-4.60 (m, 2H, H2', C4'), 4.46-4.39 (m, 1H, C5'), 4.32-4.24 (m, 1H, C5'), 4.09-3.97 (m, 1H, CHCH$_3$), 2.36-2.25 (m, 1H, H3'), 2.06-1.98 (m, 1H, H3'), 1.32-1.25 (m, 3H, CHCH$_3$).

$^{13}$C NMR (125 MHz, CD$_3$OD) δC 175.54 (CO), 175.22 (CO), 161.02 (d, $^1J_{C-F}$=207.3 Hz, C2), 160.89 (d, $^1J_{C-F}$=207.3 Hz, C2), 158.45 (d, $^3J_{C-F}$=18.2 Hz, C6), 158.23 (d, $^3J_{C-F}$=18.2 Hz, C6), 150.63 (d, $^3J_{C-F}$=18.4 Hz, C4), 140.67 (C8), 136.26 (C—Ar), 131.62, 131.54, 129.56 (CH—Ar), 129.52 (CH—Ar), 129.37 (CH—Ar), 129.31 (CH—Ar), 129.26 (CH—Ar), 128.87 (CH—Ar), 128.81 (CH—Ar), 128.29 (CH—Ar), 128.02 (CH—Ar), 127.79 (CH—Ar), 127.76 (CH—Ar), 127.51 (CH—Ar), 127.49 (CH—Ar), 127.47 (CH—Ar), 126.47 (CH—Ar), 126.33 (C—Ar), 126.27 (C—Ar), 125.97 (CH—Ar), 122.78 (CH—Ar), 122.74 (CH—Ar), 122.64 (CH—Ar), 122.62 (CH—Ar), 116.35 (d, $^4J_{C-F}$=3.0 Hz, C5), 116.15 (d, $^4J_{C-F}$=3.0 Hz, C5), 93.25 (C1'), 93.20 (C1'), 80.41 (d, $^3J_{C-P}$=7.5 Hz, C4'), 80.33 (d, $^3J_{C-P}$=7.5 Hz, C4'), 76.43 (C2'), 76.35 (C2'), 68.84 (d, $^2J_{C-P}$=5.5 Hz, C5'), 68.45 (d, $^2J_{C-P}$=5.5 Hz, C5'), 67.92 (OCH$_2$Ph), 67.92 (OCH$_2$Ph), 51.75 (CHCH$_3$), 51.52 (CHCH$_3$), 34.97 (C3'), 34.74 (C3'), 20.42 (d, $^3J_{C-P}$=6.7 Hz, CHCH$_3$), 20.20 (d, $^3J_{C-P}$=6.7 Hz, CHCH$_3$).

$^{19}$F NMR (470 MHz, CD$_3$OD) δF −53.14, −53.22.

(ES+) m/z, found: 637.2 (M+H$^+$), C$_3$H$_{30}$FN$_6$O$_7$P required: 636.57 (M).

HPLC Reverse-phase HPLC eluting with H₂O/CH₃CN from 100/10 to 0/100 in 30 minutes, 1 ml/min, l=254 nm, showed two peaks of the diastereoisomers with tR 17.09 min. and tR 17.34 min.

(2S)-benzyl 2-(((((2S,4R,5R)-5-(6-amino-2-fluoro-9H-purin-9-yl)-4-hydroxytetrahydrofuran-2-yl)methoxy)(phenoxy)phosphoryl)amino)propanoate P

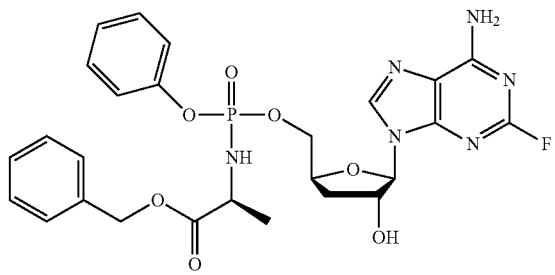 [SMILES: C[C@H](NP(=O)(OC[C@@H]1C[C@H](O)[C@H](n2cnc3c(N)nc(F)nc32)O1)Oc1ccccc1)C(=O)OCc1ccccc1]

Using General Procedure 1 above, N-methylimidazole (74 µL, 0.93 mmol) and a solution of (2S)-benzyl 2-((chloro(phenoxy)phosphoryl)amino)propanoate (196 mg, 0.56 mmol) in anhydrous THF (2 mL) were added dropwisely to a suspension of 2-Fluoro-3'-deoxyadenosine (50 mg, 0.18 mmol) in anhydrous THF (5 mL) and the reaction mixture was stirred at room temperature for 16 hours. Purification by column chromatography (eluent system CH₃OH/CH₂Cl₂ 0/100 to 6/94) and preparative TLC (eluent system CH₃OH/CH₂Cl₂ 5/95) afforded the desired compound as a white solid (5 mg, 7%).

(ES+) m/z, found: 587.1 (M+H⁺), $C_{26}H_{28}FN_6O_7P$ required: 586.17 (M). ¹⁹F NMR (470 MHz, CD₃OD): δF −53.17, −53.23. ³¹P NMR (202 MHz, CD₃OD): δP 3.95 (s), 3.67 (s). ¹H NMR (500 MHz, CDCl₃): δH 8.19 (s, 0.5H, H8), 8.16 (s, 0.5H, H8), 7.36-7.27 (m, 7H, Ar), 7.22-7.13 (m, 3H, Ar), 5.91 (d, J=1.5 Hz, 0.5H, H1'), 5.89 (d, J=1.7 Hz, 0.5H, H1'), 5.15-5.06 (m, 2H, OCH₂Ph), 4.73-4.58 (m, 2H, H2', H4'), 4.42-4.34 (m, 1H, H5'), 4.02-3.90 (m, 1H, H5'), 3.27-3.24 (m, 1H, H3'), 2.08-2.00 (m, 1H, H3'), 1.33 (d, J=7.1 Hz, 1.5H, CH₃ ala), 1.29 (d, J=7.1 Hz, 1.5H, CH₃ ala). ¹³C NMR (125 MHz, CD₃OD): δC 175.85 (d, $^3J_{C-P}$=3.7 Hz, C=O), 174.63 (d, $^3J_{C-P}$=5.0 Hz, C=O), 160.58 (d, $^1J_{C-F}$=207.5 Hz, C2), 160.53 (d, $^1J_{C-F}$=207.5 Hz, C2), 159.06 (d, $^3J_{C-F}$=18.7 Hz, C6), 159.05 (d, $^3J_{C-F}$=17.5 Hz, C6), 152.11 (d, $^2J_{C-P}$=8.75 Hz, C—Ar), 152.08 (d, $^2J_{C-P}$=8.7 Hz, C—Ar), 151.58 (d, $^3J_{C-F}$=19.7 Hz, C4), 151.56 (d, $^3J_{C-F}$=19.5 Hz, C4), 140.63 (C8), 137.28 (C—Ar), 137.21 (C—Ar), 130.78 (CH—Ar), 130.75 (CH—Ar), 129.58 (CH—Ar), 129.38 (CH—Ar), 129.34 (CH—Ar), 129.32 (CH—Ar), 129.28 (CH—Ar), 128.3 (CH—Ar), 128.02 (CH—Ar), 121.16 (CH—Ar), 121.18 (CH—Ar), 121.47 (CH—Ar), 121.51 (CH—Ar), 121.42 (CH—Ar), 121.39 (CH—Ar), 121.36 (CH—Ar), 118.75 (d, $^4J_{C-F}$=3.7 Hz, C5), 118.72 (d, $^4J_{C-F}$=3.7 Hz, C5), 93.25 (C1'), 93.18 (C1'), 80.48 (d, $^3J_{C-P}$=8.3 Hz, C4'), 80.46 (d, $^3J_{C-P}$=8.1 Hz, C4'), 76.51 (C2'), 76.49 (C2'), 68.54 (d, $^2J_{C-P}$=5.2 Hz, C5'), 68.18 (d, $^2J_{C-P}$=5.6 Hz, C5'), 67.94 (CH₂ Bn), 67.91 (CH₂ Bn), 51.71 (CH ala), 51.56 (CH ala), 34.85 (C3'), 34.64 (C3'), 20.42 (d, $^3J_{C-P}$=7.1 Hz, CH₃ ala), 20.25 (d, $^3J_{C-P}$=7.5 Hz, CH₃ ala). HPLC Reverse-phase HPLC eluting with H₂O/CH₃CN from 100/10 to 0/100 in 30 minutes, 1 ml/min, l=280 nm, showed two peaks of the diastereoisomers with $t_R$ 14.98 min. and $t_R$ 15.12 min.

2-Fluoro-3'-deoxyadenosine-5'-O-[1-naphthyl(1-pentyloxy-L-leucinyl)] phosphate

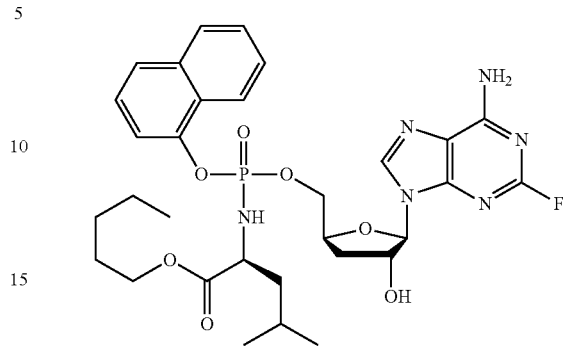

Compound Q was prepared according to the general procedure 1 using 2-Fluoro-3'-deoxyadenosine (50 mg, 0.18 mmol), N-methylimidazole (74 µL, 0.93 mmol) and naphthyl(pentyloxy-L-leucinyl) phosphorochloridate (246 mg, 0.56 mmol). Purification by column chromatography (eluent system CH₃OH/CHCl₃ 0/100 to 6/94) and preparative TLC (1000 µm, eluent system CH₃OH/CH₂Cl₂ 5/95) afforded the title compound as a white solid (65 mg, 53%).

³¹P NMR (202 MHz, CD₃OD): 4.60, 4.35.
¹H NMR (500 MHz, CD₃OD): δH 8.23 (s, 0.5H, H8), 8.20 (s, 0.5H, H8), 8.18-8.12 (m, 1H, Ar), 7.92-7.86 (m, 1H, Ar), 7.73-7.68 (m, 1H, Ar), 7.57-7.46 (m, 3H, Ar), 7.42-7.36 (m, 1H, Ar), 5.93-5.91 (m, 1H, H1'), 4.74-4.62 (m, 2H, H2', H4'), 4.55-4.50 (m, 0.5H, H5'), 4.49-4.44 (m, 0.5H, H5'), 4.43-4.37 (m, 0.5H, H5'), 4.36-4.31 (m, 0.5H, H5'), 4.02-3.86 (m, 3H, CHCH₂CH(CH₃)₂, O(CH₂)₄CH₃), 2.43-2.29 (m, 1H, H3'), 2.12-2.04 (m, 1H, H3'), 1.67-1.20 (m, 11H, O(CH₂)₄CH₃, CHCH₂CH(CH₃)₂), 0.89-0.67 (m, 9H, O(CH₂)₄CH₃, CHCH₂CH(CH₃)₂)
¹³C NMR (125 MHz, CD₃OD): δC 175.03 (d, $^3J_{C-P}$=2.5 Hz, C=O), 174.93 (d, $^3J_{C-P}$=2.5 Hz, C=O), 161.45 (d, $^1J_{C-F}$=205.5 Hz, C2), 160.39 (d, $^1J_{C-F}$=205.5 Hz, C2), 158.33 (C6), 151.60 (C4), 147.92 (C—Ar), 140.69 (C8), 136.30 (C—Ar), 128.88 (CH—Ar), 128.83 (CH—Ar), 127.80 (CH—Ar), 127.76 (CH—Ar), 127.49 (CH—Ar), 127.46 (CH—Ar), 126.48 (CH—Ar), 126.45 (CH—Ar), 126.02 (CH—Ar), 125.91 (CH—Ar), 123.03 (C—Ar), 122.81 (CH—Ar), 122.69 (CH—Ar), 116.39 (d, $^3J_{C-P}$=2.9 Hz, CH—Ar), 116.28 (C5), 116.26 (C5), 115.97 (d, $^3J_{C-P}$=2.9 Hz, CH—Ar), 93.29 (C1'), 93.23 (C1'), 80.45 (d, $^3J_{C-P}$=6.0 Hz, C4'), 80.38 (d, $^3J_{C-P}$=6.0 Hz, C4'), 76.45 (C2'), 76.41 (C2'), 68.99 (d, $^2J_{C-P}$=5.4 Hz, C5'), 68.78 (d, $^2J_{C-P}$=5.4 Hz, C5'), 66.31 (O(CH₂)₄CH₃), 66.29 (O(CH₂)₄CH₃), 54.78 (CHCH₂CH(CH₃)₂), 54.66 (CHCH₂CH(CH₃)₂), 44.16 (d, $^3J_{C-P}$=7.25 Hz, CHCH₂CH(CH₃)₂), 43.84 (d, $^3J_{C-P}$=7.3 Hz, CHCH₂CH(CH₃)₂), 35.09 (C3'), 34.79 (C3'), 29.31 (O(CH₂)₄CH₃), 29.12 (O(CH₂)₄CH₃), 25.65 (CHCH₂CH(CH₃)₂), 25.41 (CHCH₂CH(CH₃)₂), 23.33 (O(CH₂)₄CH₃), 23.11 (CHCH₂CH(CH₃)₂), 23.00 (CHCH₂CH(CH₃)₂), 21.95 (CHCH₂CH(CH₃)₂), 21.68 (CHCH₂CH(CH₃)₂), 14.29 (O(CH₂)₄CH₃).

¹⁹F NMR (470 MHz, CD₃OD): δF −53.15, −53.20.
(ES+) m/z, found: 659.3 (M+H⁺), $C_{31}H_{40}FN_6O_7P$ required: 658.66 (M).
HPLC Reverse-phase HPLC eluting with H₂O/CH₃CN from 100/10 to 0/100 in 30 minutes, 1 ml/min, l=254 nm, showed one peak of the overlapping diastereoisomers with tR 21.95 min.

(2S)-hexyl 2-(((((2S,4R,5R)-5-(6-amino-2-fluoro-9H-purin-9-yl)-4-hydroxytetrahydrofuran-2-yl)methoxy)(phenoxy)phosphoryl)amino)propanoate R

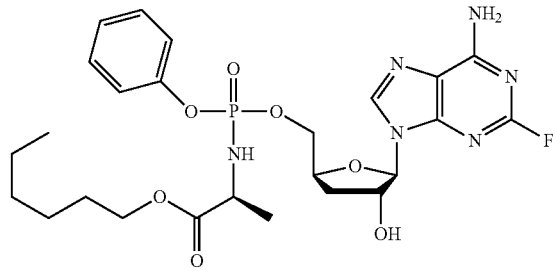 [SMILES: CCCCCCOC(=O)[C@H](C)NP(=O)(OC[C@@H]1C[C@H](O)[C@H](n2cnc3c(N)nc(F)nc32)O1)Oc1ccccc1]

Using General Procedure 1 above, N-methylimidazole (74 µL, 0.93 mmol) and a solution of (2S)-hexyl 2-((chloro(phenoxy)phosphoryl)amino)propanoate (196 mg, 0.56 mmol) in anhydrous THF (2 mL) were added dropwisely to a suspension of 2-Fluoro-3'-deoxyadenosine (50 mg, 0.18 mmol) in anhydrous THF (5 mL) and the reaction mixture was stirred at room temperature for 16 hours. Purification by column chromatography (eluent system $CH_3OH/CH_2Cl_2$ 0/100 to 6/94) and preparative TLC (eluent system $CH_3OH/CH_2Cl_2$ 5/95) afforded the desired compound as a white solid (5 mg, 7%).

(ES+) m/z, found: 587.1 (M+H$^+$), $C_{26}H_{28}FN_6O_7P$ required: 586.17 (M). $^{19}F$ NMR (470 MHz, $CD_3OD$): δF −53.15, −53.20. $^{31}P$ NMR (202 MHz, $CD_3OD$): 3.91 (s), 3.73 (s). $^1H$ NMR (500 MHz, $CDCl_3$): δH 8.21 (s, 0.5H, H8), 8.20 (s, 0.5H, H8), 7.37-7.29 (m, 7H, Ar), 7.26-7.13 (m, 3H, Ar), 5.94-5.91 (m, 1H, H1'), 4.76-4.64 (m, 2H, H2', H4'), 4.49-4.44 (m, 0.5H, H5'), 4.43- 4.37 (m, 0.5H, H5'), 4.33-4.26 (m, 1H, H5'), 4.11-3.99 (m, 2H, $CH_2$ Hex), 3.97-3.83 (m, 1H, CH ala), 2.41-2.32 (m, 1H, H3'), 2.13-2.06 (m, 1H, H3'), 1.62-1.52 (m, 2H, $CH_2$ Hex), 1.37-1.23 (m, 9H, $CH_3$ ala, $CH_2$ Hex), 0.92-0.85 (m, 3H, $CH_3$ Hex).

$^{13}C$ NMR (125 MHz, $CD_3OD$): δC 175.15 (d, $^3J_{C-P}$=3.7 Hz, C=O), 174.96 (d, $^3J_{C-P}$=5.0 Hz, C=O), 160.59 (d, $^1J_{C-F}$=207.5 Hz, C2), 160.56 (d, $^1J_{C-F}$=207.5 Hz, C2), 159.09 (d, $^3J_{C-F}$=21.2 Hz, C6), 159.08 (d, $^3J_{C-F}$=20.0 Hz, C6), 152.16 (d, $^2J_{C-P}$=7.5 Hz, C—Ar), 152.14 (d, $^2J_{C-P}$=6.3 Hz, C—Ar), 151.71 (d, $^3J_{C-F}$=20.0 Hz, C4), 151.67 (d, $^3J_{C-F}$=20.0 Hz, C4), 140.70 (d, $^5J_{C-F}$=2.5 Hz, C8), 140.68 (d, $^5J_{C-F}$=2.5 Hz, C8), 130.77 (CH—Ar), 130.74 (CH—Ar), 126.16 (CH—Ar), 126.24 (CH—Ar), 121.48 (CH—Ar), 121.44 (CH—Ar), 121.41 (CH—Ar), 121.37 (CH—Ar), 118.80 (d, $^4J_{C-P}$=3.7 Hz, C5), 118.77 (d, $^4J_{C-P}$=3.7 Hz, C5), 93.37 (C1'), 93.25 (C1'), 80.52 (d, $^3J_{C-P}$=3.7 Hz, C4'), 80.45 (d, $^3J_{C-P}$=4.1 Hz, C4'), 76.52 (C2'), 76.49 (C2'), 68.69 (d, $^2J_{C-P}$=5.4 Hz, C5'), 68.30 (d, $^2J_{C-P}$=4.9 Hz, C5'), 66.46 ($CH_2$ Hex), 51.68 (CH ala), 51.57 (CH ala), 35.02 (C3'), 34.80 (C3'), 32.58 ($CH_2$ Hex), 29.65 ($CH_2$ Hex), 26.61 ($CH_2$ Hex), 23.59 ($CH_2$ Hex), 20.60 (d, $^3J_{C-P}$=7.1 Hz, $CH_3$ ala), 20.43 (d, $^3J_{C-P}$=7.5 Hz, $CH_3$ ala), 14.35 ($CH_3$ Hex). HPLC Reverse-phase HPLC eluting with $H_2O/CH_3CN$ from 100/10 to 0/100 in 30 minutes, 1 ml/min, 1=280 nm, showed two peaks of the diastereoisomers with tR 17.83 min. and tR 18.02 min.

(2R)-benzyl 2-((((2S,4R,5R)-5-(6-amino-2-chloro-9H-purin-9-yl)-4-hydroxytetrahydrofuran-2-yl)methoxy)(naphthalen-1-yloxy)phosphorylamino)propanoate S

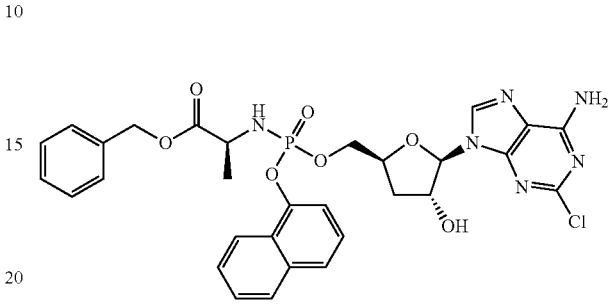

To a stirring solution of 2-chloro-3'-deoxyadenosine (100 mg, 1.0 mol/eq.) in 10 mL of anhydrous THF, 424 mg of (2S)-benzyl 2-(chloro(naphthalen-1-yloxy)phosphorylamino)propanoate (3.0 eq/mol) dissolved in 10 mL of anhydrous THF were added dropwise. To that reaction mixture, 0.14 mL of NMI (5 mol/eq.) were added dropwise at room temperature under an argon atmosphere. The reaction mixture was stirred for 88 h. The solvent was removed under reduced pressure and the residue was purified by column chromatography with gradient of eluent ($CH_3OH/CH_2Cl_2$ 0/100 to 5/95) to give a desired product as a yellow solid. (7 mg, yield=3%). MS (ES+) m/z: Found: 653 (M+H$^+$), 675 (M+Na$^+$) $C_{30}H_{30}ClN_6O_7P$ required: 652.16 (M); $^{31}P$ NMR (202 MHz, $CD_3OD$): δP 4.39 (s), 4.12 (s); $^1H$ NMR (500 MHz, $CD_3OD$): δH 8.10 (s, 0.5H, H8), 8.07 (s, 0.5H, H8), 8.02-7.97 (m, 3H, $CH_2Ph$ and Naph), 7.43-7.14 (m, 9H, $CH_2Ph$ and Naph), 5.80-5.81 (m, 1H, H1'), 4.89-4.97 (m, 2H, $CH_2Ph$) 4.49-4.53 (m, 2H, H4' and H2'), 4.30-4.35 (m, 1H, H5'), 4.15-4.21 (m, 1H, H5'), 3.87-3.95 (m, 1H, $CHCH_3$), 2.12-2.23 (m, 1H, H3'), 1.86-1.93 (m, 1H H3'), 1.14-1.17 (m, 3H, $CHCH_3$); 13C NMR (125 MHz, $CD_3OD$): δC 174.85 (d $J_{CP}$=4.0 Hz, C=O), 174.55 (d $J_{CP}$=4.3 Hz, C=O), 158.07, 158.04 (C6), 155.31, 155.28 (C2), 151.34, 151.31 (C4), 149.69 (C—Ar), 147.96 (d $^3J_{CP}$=7.25 Hz, C-ipso Naph), 147.90 (d $^3J_{CP}$=7.0 Hz, C-ipso Naph), 140.70 (C8), 137.21, 137.16 (C-ipso $CH_2Ph$), 136.26 (C—Ar), 130.92, 130.80, 129.56, 129.53, 129.31, 129.27, 129.25, 128.88, 128.81 (CH—Ar), 127.78 (d $J_{CP}$=4.7 Hz, CH—Ar), 127.50 (d $J_{CP}$=6.2 Hz, CH—Ar), 126.48, 126.02, 125.97 (CH—Ar), 119.46, 119.42 (C5), 116.33 (d, $J_{CP}$=3.0, CH—Ar), 116.16 (d, $J_{CP}$=3.4, CH—Ar), 93.30, 93.27 (C1'), 80.56 (d J=8.3 Hz, C4'), 80.51 (d J=8.4 Hz, C4'), 76.61, 76.54 (C2'), 68.74 (d $J_{CP}$=5.3 Hz, C5'), 68.54 (d $J_{CP}$=5.1 Hz, C5'), 67.93, 67.90 ($CH_2Ph$), 51.81, 51.70 ($CHCH_3$), 34.79, 34.53 (C3'), 20.42 (d $J_{CP}$=6.5 Hz, $CHCH_3$), 20.23 (d $J_{CP}$=7.7 Hz, $CHCH_3$); HPLC Reverse-phase HPLC eluting with $H_2O/CH_3CN$ from 90/10 to 0/100 in 30 minutes, F=1 ml/min, 1=254 nm, $t_R$ 18.03 min.

2-Chloro-3'deoxyadenosine 5'-O-[1-phenyl (2,2-dimethylpropoxy-L-alanine)]phosphate T

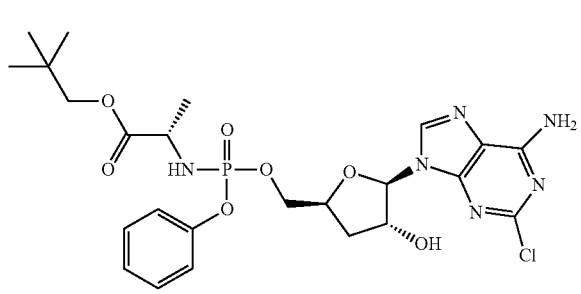 [SMILES: C[C@H](NP(=O)(OC[C@@H]1C[C@@H](O)[C@H](n2cnc3c(N)nc(Cl)nc32)O1)Oc1ccccc1)C(=O)OCC(C)(C)C]

Compound T was prepared according to the general procedure 1 using 2-chloro-3'-deoxyadenosine (350 mg, 1.25 mmol), N-methylimidazole (490 μL, 6.15 mmol) and phenyl(2,2-dimethylpropoxy-L-alaninyl) phosphorochloridate (1231 mg, 3.69 mmol). Purification by column chromatography (eluent system $CH_3OH/CH_2Cl_2$ 0/100 to 5/95) and preparative TLC (1000 m, eluent system $CH_3OH/CH_2Cl_2$ 4/96) afforded the title compound as a white solid (181 mg, 25%).

$^{31}$P NMR (202 MHz, $CD_3OD$): δP 3.93, 3.72.

$^1$H NMR (500 MHz, $CD_3OD$): δH 8.12 (s, 0.5H, H8), 8.10 (s, 0.5H, H8), 7.19-7.23 (m, 2H, Ph), 7.03-7.12 (m, 3H, Ph), 5.84 (d J=2, 0.5H, H1'), 5.83 (d J=2, 0.5H, H1'), 4.54-4.60 (m, 2H, H4' and H2'), 4.34-4.38 (m, 0.5H, H5'), 4.27-4.31 (m, 0.5H, H5'), 4.16-4.23 (m, 1H, H5'), 3.80-3.90 (m, 1H, $CHCH_3$), 3.57-3.73 (m, 2H $OCH_2C(CH_3)_3$), 2.18-2.28 (m, 1H, H3'), 1.94-1.99 (m, 1H, H3'), 1.20-1.24 (m, 3H, $CHCH_3$), 0.81 (s, 4.5H $OCH_2(CH_3)_3$), 0.79 (s, 4.5H $OCH_2C(CH_3)_3$).

$^{13}$C NMR (125 MHz, $CD_3OD$): δC 175.09 ($d^3J_{CP}$=4.75 Hz, C=O), 174.90 ($d^3J_{CP}$=5.37 Hz, C=O), 158.10, (C6), 155.31, 155.28 (C2), 152.14 ($d^2J_{CP}$=6.37 Hz, C-ipso Ph), 152.13 ($d^2J_{CP}$=6.25 Hz, C-ipso Ph), 151.33, 151.30 (C4), 140.87, 140.76 (C8), 130.78, 130.77 (CH—Ar), 126.17, 126.42 (CH—Ar), 121.45 ($d^3J_{CP}$=11.75 Hz, CH—Ar), 121.41 ($d^3J_{CP}$=11.75 Hz, CH—Ar), 119.52, 119.48 (C5), 93.49, 93.35 (C1'), 80.67 ($d^3J$=8.62 Hz, C4'), 80.65 ($d^3J$=8.25 Hz, C4'), 76.70, 76.67 (C2'), 75.43, ($OCH_2C(CH_3)_3$), 68.68 ($d^2J_{CP}$=5.12 Hz, C5'), 68.42 ($d^2J_{CP}$=5.12 Hz, C5'), 51.77, 51.60 ($CHCH_3$), 34.94, 34.67 (C3'), 32.36, 32.32 ($OCH_2C(CH_3)_3$), 26.78, 26.76 ($OCH_2C(CH_3)_3$), 20.83 (d $J_{CP}$=6.25 Hz, $CHCH_3$), 20.61 (d $J_{CP}$=7.12 Hz, $CHCH_3$).

MS (ES+) m/z: Found: 583 (M+H$^+$), 605 (M+Na$^+$) $C_{24}H_{32}ClN_6O_7P$ required: 582.18 (M).

HPLC Reverse-phase HPLC eluting with $H_2O/CH_3CN$ from 90/10 to 0/100 in 30 minutes, F=1 ml/min, 1=254 nm, $t_R$ 16.37, 16.55 min.

2-Chloro-3'deoxyadenosine 5'-O-[1-naphtyl (2,2-dimethylpropoxy-L-alanine)] phosphate U

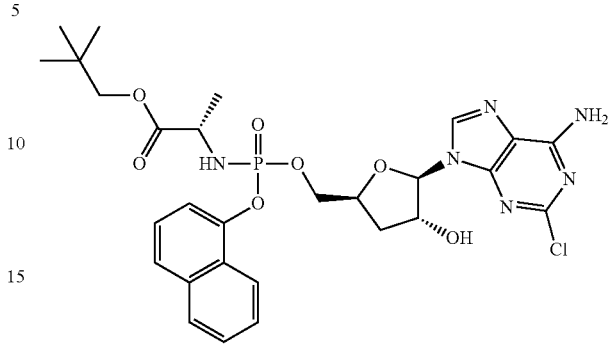

Compound U was prepared according to the general procedure 1 using 2-chloro-3'-deoxyadenosine (350 mg, 1.25 mmol), N-methylimidazole (490 μL, 6.15 mmol) and naphtyl(2,2-dimethylpropoxy-L-alaninyl) phosphorochloridate (1416 mg, 3.69 mmol). Purification by column chromatography (eluent system $CH_3OH/CH_2Cl_2$ 0/100 to 5/95) and preparative TLC (1000 μm, eluent system $CH_3OH/CH_2Cl_2$ 4/96) afforded the title compound as a white solid (264 mg, 34%).

$^{31}$P NMR (202 MHz, $CD_3OD$): δP 4.35, 4.20.

$^1$H NMR (500 MHz, $CD_3OD$): δH 8.23 (s, 0.5H, H8), 8.21 (s, 0.5H, H8), 8.11-8.16 (m, 1H, Naph), 7.86-7.89 (m, 1H, Naph), 7.69-7.70 (m, 1H, Naph), 7.54-7.46 (m, 3H, Naph), 7.37-7.41 (m, 1H, Naph), 5.95 (d J=2, 0.5H, H1'), 5.94 (d J=1.5, 0.5H, H1'), 4.67-4.73 (m, 2H, H4' and H2'), 4.34-4.55 (m, 2H, H5'), 4.00-4.08 (m, 1H, $CHCH_3$), 3.66-3.81 (m, 2H $OCH_2C(CH_3)_3$), 2.28-2.41 (m, 1H, H3'), 2.03-2.10 (m, 1H, H3'), 1.31-1.34 (m, 3H, $CHCH_3$), 0.90 (s, 4.5H $OCH_2C(CH_3)_3$), 0.89 (s, 4.5H $CH_2(CH_3)_3$).

$^{13}$C NMR (125 MHz, $CD_3OD$): δC 175.11 (d $J_{CP}$=4.1 Hz, C=O), 174.85 (d $J_{CP}$=5.0 Hz, C=O), 158.10, 158.04 (C6), 155.32, 155.30 (C2), 151.33 (C4), 147.96 ($d^2J_{CP}$=7.25 Hz, C-ipso Naph), 147.93 ($d^2J_{CP}$=7.25 Hz, C-ipso Naph), 140.84, 140.76 (C8), 136.29 (C—Ar), 128.87, 128.82 (CH—Ar), 127.85 (C—Ar), 127.77, 127.74, 127.48, 127.45, 126.47, 125.99, 125.96, 122.74, 122.66 (CH—Ar), 119.47 (C5), 116.29 ($d^3J_{CP}$=3.4 Hz, CH—Ar), 116.17 ($d^3J_{CP}$=2.9 Hz, CH—Ar), 93.42, 93.34 (C1'), 80.57 ($d^3J_{CP}$=8.1 Hz, C4'), 80.53 ($d^3J_{CP}$=5.1 Hz, C4'), 76.61, 76.53 (C2'), 75.41, 75.38 ($OCH_2C(CH_3)_3$), 68.95 ($d^2J_{CP}$=5.3 Hz, C5'), 68.82 ($d^2J_{CP}$=5.2 Hz, C5'), 51.84, 51.73 ($CHCH_3$), 35.04, 34.75 (C3'), 32.29 ($OCH_2C(CH_3)_3$), 26.70 ($OCH_2C(CH_3)_3$), 20.76 ($d^3J_{CP}$=6.4 Hz, $CHCH_3$), 20.55 ($d^3J_{CP}$=7.2 Hz, $CHCH_3$).

MS (ES+) m/z: Found: 633 (M+H$^+$), 655 (M+Na$^+$) $C_{28}H_{34}ClN_6O_7P$ required: 652.16 (M).

HPLC Reverse-phase HPLC eluting with $H_2O/CH_3CN$ from 90/10 to 0/100 in 30 minutes, F=1 ml/min, 1=254 nm, $t_R$ 19.16 min.

2-Chloro-3'deoxyadenosine 5'-O-[1-phenyl (ethoxy-L-alanine)] phosphate V

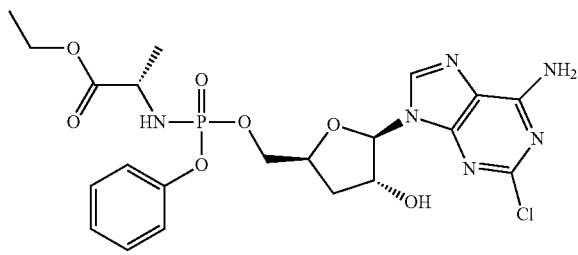 [SMILES: CCOC(=O)[C@H](C)NP(=O)(OC[C@@H]1C[C@@H](O)[C@H](n2cnc3c(N)nc(Cl)nc32)O1)Oc1ccccc1]

Compound V was prepared according to the general procedure 4 using 2-chloro-3'-deoxyadenosine (343 mg, 0.66 mmol), tertbutyldimethylsilyl chloride (328 mg 2.18 mmol) imidazole (297 mg, 4.36 mmol). Purification by column chromatography (eluent system $CH_3OH/CH_2Cl_2$ 0/100 to 12/88) afforded intermediate 1 in a quantitative yield. Next, intermediate 1 (970 mg, 1.89 mmol) was reacted with 12 mL of a solution $THF/H_2O/TFA$ 4/1/1. Purification by column chromatography (eluent system $CH_3OH/CH_2Cl_2$ 0/100 to 12/88) afforded intermediate 2 (544 mg, 72%). Then, intermediate 2 (204 mg, 0.51 mmol) and was reacted with tertbutylmagnesium chloride and a solution of phenyl (ethyloxy-L-alaninyl) phosphorochloridate (348.56 mg, 1.02 mmol) in anhydrous THF (5 mL). Purification by column chromatography (eluent system $CH_3OH/CH_2Cl_2$ 0/100 to 8/92) afforded intermediate 3 (93 mg, 28%). Finally intermediate 3 (93 mg, 0.14 mmol) was reacted with a solution of $THF/TFA/H_2O$ 1/1/1 (3 mL). Purification by preparative TLC (2000 µm, eluent system $CH_3OH/CH_2Cl_2$ 4/96) afforded the title compound as a white solid (50 mg, 66%). (Overall yield 13%)

$^{31}P$ NMR (202 MHz, $CD_3OD$): δP 3.93, 3.72.

$^1H$ NMR (500 MHz, $CD_3OD$): δH 8.12 (s, 0.5H, H8), 8.11 (s, 0.5H, H8), 7.18-7.23 (m, 2H, Ph), 7.03-7.12 (m, 3H, Ph), 5.85 (d J=1.5, 0.5H, H1'), 5.84 (d J=2, 0.5H, H1'), 4.55-4.62 (m, 2H, H4' and H2'), 4.34-4.38 (m, 0.5H, H5'), 4.28-4.32 (m, 0.5H, H5'), 4.16-4.22 (m, 1H, H5'), 3.93-4.03 (m, 2H, $OCH_2CH_3$), 3.70-3.84 (m, 1H, $CHCH_3$), 2.20-2.28 (m, 1H, H3'), 1.95-1.99 (m, 1H, H3'), 1.15-1.21 (m, 3H, $CHCH_3$), 1.06-1.11 (m, 3H, $OCH_2CH_3$).

$^{13}C$ NMR (125 MHz, $CD_3OD$): δC 173.66 ($d^3J_{CP}$=4.5 Hz, C=O), 173.65 ($d^3J_{CP}$=5.3 Hz, C=O), 156.68, 156.70 (C6), 153.93, 153.88 (C2), 150.72 ($d^2J_{CP}$=6.7 Hz, C-ipso Ph), 150.71 (d $^2J_{CP}$=6.5 Hz, C-ipso Ph), 149.89, 149.94 (C4), 139.41, 139.35 (C8), 129.33 (CH—Ar), 124.74, 124.73 (CH—Ar), 120.03 ($d^3J_{CP}$=4.75 Hz, CH—Ar), 119.97 ($d^3J_{CP}$=4.87 Hz, CH—Ar), 118.07, 118.03 (C5), 92.02, 91.88 (C1'), 79.26, 79.19 (C4'), 75.26, 75.24 (C2'), 67.18 ($d^2J_{CP}$=5.25 Hz, C5'), 66.81 ($d^2J_{CP}$=5.12 Hz, C5'), 60.96 ($OCH_2CH_3$), 50.23, 50.12 ($CHCH_3$), 33.46, 33.21 (C3'), 19.16 ($d^3J_{CP}$=6.3 Hz, $CHCH_3$), 18.97 ($d^3J_{CP}$=7.2 Hz, $CHCH_3$), 13.10, 13.07 ($OCH_2CH_3$).

MS (ES+) m/z: Found: 541 (M+H$^+$), 563 (M+Na$^+$) $C_{21}H_{26}ClN_6O_7P$ required: 540 (M).

HPLC Reverse-phase HPLC eluting with $H_2O/CH_3CN$ from 90/10 to 0/100 in 30 minutes, F=1 ml/min, 1=254 nm, $t_R$ 12.41, 12.83 min.

(2S)-isopropyl-2-(((((2S,4R,5R)-5-(6-amino-9H-purin-9-yl)-4-hydroxytetrahydrofuran-2-yl)methoxy)(phenoxy)phosphoryl)amino) propanoate W

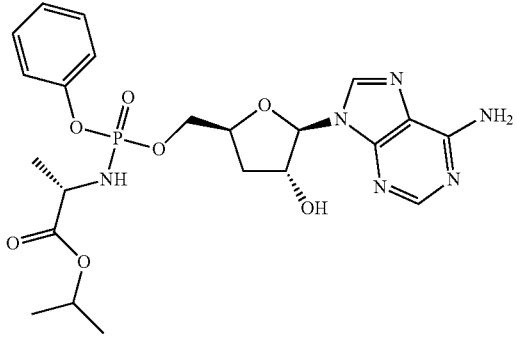 [SMILES: CC(C)OC(=O)[C@H](C)NP(=O)(OC[C@@H]1C[C@@H](O)[C@H](n2cnc3c(N)ncnc32)O1)Oc1ccccc1]

N-methylimidazole (240 µL, 5 mmol) and a solution of (2S)-isopropyl 2-((chloro(phenoxy)phosphoryl)amino)propanoate (546 mg, 3 mmol) in anhydrous THF (5 mL) were added dropwisely to a suspension of (2R,3R,5S)-2-(6-amino-9H-purin-9-yl)-5-(hydroxymethyl)tetrahydrofuran-3-ol (150 mg, 0.6 mmol) in anhydrous THF (3 mL) and the reaction mixture was stirred at room temperature during a period of 16 hours. Purification by column chromatography (eluent system $CH_3OH/CH_2Cl_2$ 0/100 to 6/94) and preparative TLC (2000 µicron, eluent system $CH_3OH/CH_2Cl_2$ 5/95) afforded the desired compound as white solid (40 mg, 13%).

MS (ES+) m/z: Found: 521.2 (M+H$^+$), 543.3 (M+Na$^+$), 1063.4 (2M+Na$^+$) $C_{31}H_{33}N_6O_8P$ required: 520.18 (M).

$^{31}P$ NMR (202 MHz, $CD_3OD$): δP 3.99 (s), 3.82 (s).

$^1H$ NMR (500 MHz, $CD_3OD$): δH 8.16 (s, 0.5H, H8), 8.15 (s, 0.5H, H8), 8.11 (s, 1H, H-2) 7.23-7.20 (m, 2H, Ph), 7.11-7.03 (m, 3H, Ph), 5.91 (d J=2.0 Hz, 0.5H, H1'), 5.90 (d J=2.0 Hz, 0.5H, H1'), 4.85-4.79 (m, 1H, $CH(CH_3)_2$, 4.64-4.63 (m, 1H, H4'), 4.60-6.57 (m, 1H, H2'), 4.37-4.33 (m, 1H, H5'), 4.31-4.28 (m, 1H, H5'), 3.74-4.22-4.17 (m, 1H, H5'), 3.70 (m, 1H, CH ala), 2.02-1.97 (m, 1H, H3'), 2.04-2.01 (m, 1H, H3'), 1.18-1.14 (m, 3H, $CH_3$), 1.24 (m, δH, $CH(CH_3)_2$)

HPLC Reverse-phase HPLC eluting with $H_2O/CH_3CN$ from 100/10 to 0/100 in 30 minutes, F=1 ml/min, λ=200 nm, showed two peaks of the diastereoisomers with $t_R$ 11.58 min. and $t_R$11.92 min.

Solvents and Reagents. The following anhydrous solvents were purchased from Sigma-Aldrich:

dichloromethane ($CH_2Cl_2$), trimethylphosphate (($CH_3O)_3PO$). Amino acid esters commercially available were purchased from Sigma-Aldrich. All reagents commercially available were used without further purification.

Thin Layer Chromatography (TLC).

Precoated aluminium backed plates (60 F254, 0.2 mm thickness, Merck) were visualized under both short and long wave ultraviolet light (254 and 366 nm) or by burning using the following TLC indicators: (i) molybdate ammonium cerium sulphate; (ii) potassium permanganate solution. Preparative TLC plates (20 cm×20 cm, 500-2000 µm) were purchased from Merck.

Flash Column Chromatography. Flash column chromatography was carried out using silica gel supplied by Fisher (60A, 35-70 µm). Glass columns were slurry packed using the appropriate eluent with the sample being loaded as a concentrated solution in the same eluent or preadsorbed onto silica gel. Fractions containing the product were identified by TLC, and pooled and the solvent was removed in vacuo.

High Performance Liquid Chromatography (HPLC). The purity of the final compounds was verified to be >95% by HPLC analysis using either I) ThermoSCIENTIFIC, SPECTRA SYSTEM P4000, detector SPECTRA SYSTEM UV2000, Varian Pursuit XRs 5 C18, 150×4.6 mm (as an analytic column) or II) Varian Prostar (LC Workstation-Varian Prostar 335 LC detector), Thermo SCIENTIFIC Hypersil Gold C18, 5a, 150×4.6 mm (as an analytic column). For the method of elution see the experimental part.

Nuclear Magnetic Resonance (NMR). $^1$H NMR (500 MHz), $^{13}$C NMR (125 MHz), $^{31}$P NMR (202 MHz) and $^{19}$F NMR (470 MHz) were recorded on a Bruker Avance 500 MHz spectrometer at 25° C. Chemical shifts ($\delta$) are quoted in parts per million (ppm) relative to internal MeOH-$d_4$ ($\delta$ 3.34 $^1$H-NMR, $\delta$ 49.86 $^{13}$C-NMR) and CHCl$_3$-$d_4$ ($\delta$ 7.26 $^1$H NMR, $\delta$ 77.36 $^{13}$C NMR) or external 85% $H_3PO_4$ ($\delta$ 0.00 $^{31}$P NMR). Coupling constants (J) are measured in Hertz. The following abbreviations are used in the assignment of NMR signals: s (singlet), d (doublet), t (triplet), q (quartet), m (multiplet), bs (broad singlet), dd (doublet of doublet), dt (doublet of triplet), app (apparent). The assignment of the signals in $^1$H NMR and $^{13}$C NMR was done based on the analysis of coupling constants and additional two-dimensional experiments (COSY, HSQC, HMBC, PENDANT).

Mass spectrometry (MS). Low resolution mass spectra were performed on Bruker Daltonics microTof-LC, (atmospheric pressure ionization, electron spray mass spectroscopy) in either positive or negative mode.

Purity of final compounds. The ≥95% purity of all the final compounds was confirmed using HPLC analysis.

Example 2—Cytoxicity

Exemplified compounds embodying the present invention were assessed in the following procedures for their anti-cancer potency.

In vitro viability assays were performed to assess the effects of compounds on cell viability in 7 selected cell lines over 72 hr using the CellTiterGlo (CTG, Promega-G7573) assay. The tests were performed in duplicates with treatment of compounds at 9 points, 3.16 folds titration in 96 well plates over ~72 hr. The compound starting concentrations were 198 mM. Cell viability assay using CellTiterGlo in 96-well plate were performed. The compound treatment was 72 hrs, under standard growth conditions, and in duplicate. Compounds were dissolved to 40 mM with thawed 100%. Compounds were serially diluted at 3.16 fold in thawed DMSO, and warmed to 37° C. before being dissolved in media (2 µl+200 µl). After compounds were dissolved in media (media was also warmed to 37° C.). Media containing compounds were warmed to 37° C. in incubator and then compounds in media were added to cell plates (50 µl+50 µl), in duplicates. The compounds final concentrations were from 198M to 19.9 nM. All compound solubilities were checked and recorded again, then the plates were transferred to $CO_2$ tissue culture incubator immediately and incubated for 3 days. DMSO final concentration is 0.5%.

The results of the initial screening are presented in Table II. A represents a relative $IC_{50}$ of from 0.1 to 5 µM, B represents a relative $IC_{50}$ greater than 5 µM and up to 15 µM, C represents an relative $IC_{50}$ of greater than 15 µM and up to 100 µM; and D represents an relative $IC_{50}$ of greater than 100 µM.

TABLE II

| Cpnd | MOLT-4[a] $IC_{50}$[f] | M.I. %[g] | KG-1[b] $IC_{50}$ | M.I. % | HL-60[c] $IC_{50}$ | M.I. % | CCRF-CEM[d] $IC_{50}$ | M.I. % | K562[e] $IC_{50}$ | M.I. % |
| --- | --- | --- | --- | --- | --- | --- | --- | --- | --- | --- |
| cordycepin | C | 52 | C | 78 | C | 88 | C | 12 | C | 88 |
| A | A | 98 | B | 92 | B | 97 | A | 100 | A | 92 |
| B | A | 100 | B | 100 | B | 100 | A | 100 | A | 97 |
| C | A | 93 | D | 65 | C | 82 | B | 94 | B | 92 |
| D | A | 100 | B | 100 | B | 100 | B | 100 | B | 99 |
| G | C | 75 | C | 63 | C | 57 | C | 65 | C | 78 |
| H | C | 100 | C | 69 | C | 80 | C | 100 | C | 89 |
| I | C | 100 | C | 93 | C | 99 | C | 99 | C | 87 |
| E | B | 97 | C | 69 | C | 74 | C | 90 | D | 81 |
| J | A | 100 | C | 29 | C | 98 | C | 100 | C | 97 |
| F | A | 100 | C | 98 | C | 100 | S | 99 | C | 91 |

| Compound | MCF-7[h] $IC_{50}$ | M.I. % | HepG2[i] $IC_{50}$ | M.I. % |
| --- | --- | --- | --- | --- |
| cordycepin | C | 78 | C | 66 |
| A | A | 94 | B | 76 |
| B | A | 99 | B | 95 |
| C | B | 87 | C | 59 |
| D | A | 100 | B | 99 |
| G | B | 97 | C | 67 |
| H | A | 94 | B | 55 |

TABLE II-continued

| I | B | 99 | C | 90 |
|---|---|----|---|----|
| E | C | 78 | C | 59 |
| J | C | 97 | C | 55 |
| F | B | 99 | C | 84 |

[a] MOLT-4: acute lymphoblastic leukaemia;
[b] KG-1: acute myelogenous leukaemia;
[c] HL-60: acute promyelocytic leukaemia;
[d] CCRF-CEM: acute lymphoblastic leukaemia;
[e] K562: chronic myelogenous leukaemia;
[f] TC$_{50}$ µM: relative IC$_{50}$;
[g] M.I. %: maximum percentage inhibition of cell viability.
[h] MCF-7: breast adenocarcinoma;
[i] HepG2: hepatocellular carcinoma A subset of compounds of the invention were then assayed for their cytotoxic activity in a broader array of different solid tumours and haematological malignancies using the following assay.

Solid Tumour and Haematological Malignancy Assay

In vitro viability assay were performed to assess the effects of compounds on cell viability in selected cell lines over 72 hr using the CellTiterGlo (CTG, Promega-G7573) assay. The tests were performed in duplicates with treatment of compounds at 9 points, 3.16 folds titration in 96 well plates over ~72 hr. The compound starting concentrations were 198 mM. Cell viability assay using CellTiterGlo in 96-well plate were performed. Compound treatment 72 hrs, standard growth conditions, duplicates. Compounds were dissolved to 40 mM with thawed 100%. Compounds were serially diluted at 3.16 fold in thawed DMSO, and warmed to 37° C. before being dissolved in media (2 µl+200 µl). After compounds were dissolved in media, media containing compounds were warmed to 37° C. in incubator and then compounds in media were added to cell plates (50 µl+50 µl) in duplicates. The compounds' final concentrations were from 198M to 19.9 nM. All compound solubilities were checked and recorded again, then the plates were transferred to CO$_2$ tissue culture incubator immediately and incubated for 3 days. DMSO final concentration is 0.5%.

The following cell lines were tested and are referred to in the Table IV below:

TABLE III

| Cell line | Malignancy | Cell line | Malignancy |
|---|---|---|---|
| MOLT-4 | Acute lymphoblastic leukaemia | HEL92.1.7 | Erythroleukaemia |
| CCRFCEM | Acute lymphoblastic leukaemia | HL-60 | Promyelocytic leukaemia |
| RL | Non-Hodgkin's lymphoma | MV4-11 | Biphenotypic B myelomonocytic leukemia |
| HS445 | Hodgkin lymphoma | HepG2 | Hepatocellular carcinoma |
| RPMI8226 | Human multiple myeloma | HT29 | Colon adenocarcinoma |
| K562 | Chronic myelogenous leukaemia | BxPC-3 | Pancreatic cancer |
| KG-1 | Acute myelogenous leukaemia | MCF-7 | Breast adenocarcinoma |
| THP-1 | Acute monocytic leukaemia | MiaPaCa2 | Breast adenocarcinoma |

TABLE III-continued

| Cell line | Malignancy | Cell line | Malignancy |
|---|---|---|---|
| Z-138 | Mantle cell lymphoma | SW620 | Color adenocarcinoma |
| NCI-H929 | Plasmacytoma | Jurkat | acute T cell leukaemia |

The results of the further screening are presented in Tables IV-VII. For Tables IV to VI: A represents in absolute IC$_{50}$ of from 0.1 µM to 5 µM, B represents an absolute IC$_{50}$ greater than 5 µM and up to 15 µM, C represents an absolute IC$_{50}$ of greater than 15 µM and up to 100 µM; and D represents an absolute IC$_{50}$ of greater than 100 µM. For Table VII: A represents an absolute EC$_{50}$ of from 0.1 µM to 5 µM, B represents an absolute EC$_{50}$ greater than 5 µM and up to 15 µM, C represents an absolute EC$_{50}$ of greater than 15 µM and up to 100 µM; and D represents an absolute EC$_{50}$ of greater than 100 µM.

TABLE IV

| | CCRFCEM | | MOLT-4 | | KG-1 | | Jurkat | |
|---|---|---|---|---|---|---|---|---|
| Cmpd | IC$_{50}$ | MI % | IC$_{50}$ | MI % | IC$_{50}$ | MI % | IC$_{50}$ | MI % |
| Cordycepin | D | 41 | D | 46 | D | 69 | D | 20 |
| A | A | 100 | A | 98 | C | 100 | A | 100 |
| B | A | 100 | A | 98 | B | 97 | A | 100 |
| C | B | 100 | A | 92 | C | 102 | B | 100 |
| F | A | 101 | A | 98 | C | 95 | A | 100 |
| E | A | 100 | A | 98 | C | 100 | B | 95 |

| | THP-1 | | RL | | HS445 | | NCI-H929 | |
|---|---|---|---|---|---|---|---|---|
| Cmpd | IC$_{50}$ | MI % | IC$_{50}$ | MI % | IC$_{50}$ | MI % | IC$_{50}$ | MI % |
| Cordycepin | D | −3 | D | 17 | D | 2 | D | 24 |
| A | C | 74 | A | 93 | C | 98 | B | 100 |
| B | C | 99 | A | 96 | B | 96 | A | 99 |
| C | C | 99 | B | 100 | C | 102 | B | 104 |
| F | C | 100 | B | 90 | C | 92 | B | 100 |
| E | D | 43 | B | 88 | C | 85 | C | 98 |

| | RPMI-8226 | | MV4-11 | | HEL92.1.7 | | K562 | |
|---|---|---|---|---|---|---|---|---|
| Cmpd | IC$_{50}$ | MI % | IC$_{50}$ | MI % | IC$_{50}$ | MI % | IC$_{50}$ | MI % |
| Cordycepin | D | 1 | D | 1 | C | 88 | C | 78 |
| A | B | 96 | A | 99 | B | 100 | A | 96 |
| B | B | 102 | A | 99 | A | 98 | A | 99 |
| C | C | 103 | B | 106 | A | 99 | B | 100 |
| F | C | 106 | A | 100 | B | 99 | A | 93 |
| E | C | 89 | B | 101 | C | 101 | B | 90 |

TABLE IV-continued

| Cmpd | HL-60 IC$_{50}$ | HL-60 MI % | Z138 IC$_{50}$ | Z138 MI % | BxPC-3 IC$_{50}$ | BxPC-3 MI % | HepG2 IC$_{50}$ | HepG2 MI % |
|---|---|---|---|---|---|---|---|---|
| Cordycepin | D | 61 | B | 95 | D | 22 | D | 13 |
| A | B | 99 | C | 95 | C | 81 | C | 75 |
| B | A | 99 | B | 100 | B | 90 | B | 98 |
| C | B | 100 | B | 100 | C | 99 | C | 99 |
| F | B | 96 | C | 76 | C | 78 | C | 79 |
| E | B | 95 | C | 93 | C | 71 | C | 67 |

| Cmpd | HT29 IC$_{50}$ | HT29 MI % | MCF7 IC$_{50}$ | MCF7 MI % | MiaPaCa-2 IC$_{50}$ | MiaPaCa-2 MI % | SW620 IC$_{50}$ | SW620 MI % |
|---|---|---|---|---|---|---|---|---|
| Cordycepin | D | 44 | D | 77 | D | 35 | D | 10 |
| A | B | 93 | A | 99 | B | 96 | C | 85 |
| B | B | 98 | A | 96 | A | 98 | B | 93 |
| C | C | 99 | A | 102 | B | 106 | C | 100 |
| F | C | 89 | B | 103 | B | 101 | C | 90 |
| E | C | 76 | B | 89 | C | 91 | C | 74 |

TABLE V

| Cmpd | CCRFCEM IC$_{50}$ | CCRFCEM M.I. % | KG-1 IC$_{50}$ | KG-1 M.I. % | K562 IC$_{50}$ | K562 M.I. % | MOLT-4 IC$_{50}$ | MOLT-4 M.I. % |
|---|---|---|---|---|---|---|---|---|
| 2-OMe-Cordycepin | D | −4 | D | 1 | D | 40 | D | 1 |
| L | C | 100 | D | 92 | C | 104 | C | 101 |
| K | B | 102 | C | 99 | C | 100 | C | 104 |
| M | B | 100 | C | 102 | B | 100 | B | 101 |
| N | C | 93 | C | 96 | C | 78 | C | 97 |

| Cmpd | HT29 IC$_{50}$ | HT29 M.I. % | MCF7 IC$_{50}$ | MCF7 M.I. % | NCI-H929 IC$_{50}$ | NCI-H929 M.I. % | RL IC$_{50}$ | RL M.I. % |
|---|---|---|---|---|---|---|---|---|
| 2-OMe-Cordycepin | D | 19 | D | 8 | D | 51 | D | 0 |
| L | C | 81 | C | 90 | C | 104 | C | 97 |
| K | C | 98 | B | 99 | B | 102 | C | 104 |
| M | C | 100 | C | 100 | B | 99 | B | 100 |
| N | C | 69 | C | 73 | C | 99 | C | 88 |

TABLE VI

| Cmpd | HepG2 IC$_{50}$ | HepG2 M.I. % | HL-60 IC$_{50}$ | HL-60 M.I. % | HT29 IC$_{50}$ | HT29 M.I. % |
|---|---|---|---|---|---|---|
| 2-F-Cordycepin | C | 82 | B | 96 | C | 73 |
| O | B | 83 | A | 101 | C | 84 |
| P | B | 74 | A | 100 | B | 87 |
| Q | A | 94 | A | 99 | C | 88 |
| R | B | 82 | A | 100 | C | 92 |

TABLE VI-continued

| Cmpd | CCRFCEM | | HEL92.1.7 | | KG-1 | |
|---|---|---|---|---|---|---|
| | IC50 | M.I. % | IC$_{50}$ | M.I. % | IC$_{50}$ | M.I. % |
| 2-F-Cordycepin | C | 101 | B | 99 | B | 99 |
| O | A | 99 | A | 100 | B | 99 |
| P | A | 99 | A | 99 | A | 97 |
| Q | A | 101 | A | 99 | B | 103 |
| R | A | 100 | A | 99 | A | 96 |

| Cmpd | MiaPaCa-2 | | MCF7 | | K562 | |
|---|---|---|---|---|---|---|
| | IC$_{50}$ | M.I. % | IC$_{50}$ | M.I. % | IC$_{50}$ | M.I. % |
| 2-F-Cordycepin | C | 100 | C | 97 | C | 97 |
| O | A | 100 | A | 95 | A | 99 |
| P | A | 98 | A | 95 | A | 97 |
| Q | A | 100 | A | 99 | A | 100 |
| R | B | 98 | A | 87 | B | 96 |

TABLE VII

| | | BxPC-3-Luc | CCRF-CEM | HEL.92.1.7 | HepG2 | HL-60 | HS445 | HT29 | K562 | KG-1 |
|---|---|---|---|---|---|---|---|---|---|---|
| 2-Cl-cordycepin | EC$_{50}$ | D | C | B | D | C | D | D | D | D |
| | MI % | −1.3 | 98.1 | 94.3 | 31.1 | 84.4 | −1.9 | 4.4 | 37.6 | 4.3 |
| Cmpd. S | EC$_{50}$ | C | B | B | C | B | C | C | C | C |
| | MI % | 82.6 | 100 | 100.4 | 84.6 | 101.9 | 105.9 | 88.1 | 101.4 | 99 |

| | | MCF-7 | Mia-Pa-Ca-2 | MOLT-4 | MV4-11 | NCI-H929 | RL | RPMI-8226 | SW620 | THP-1 | Z-138 |
|---|---|---|---|---|---|---|---|---|---|---|---|
| 2-Cl-cordycepin | EC$_{50}$ | D | D | D | C | B | C | D | D | D | C |
| | MI % | −0.9 | 17.7 | 80.4 | 100.2 | 93.6 | 84.1 | 29 | 36.3 | 24.1 | 99.5 |
| Compd. S | EC$_{50}$ | C | C | B | B | B | B | C | C | C | C |
| | MI % | 100.9 | 98.2 | 100.1 | 100.9 | 102.3 | 100.2 | 99.6 | 92.1 | 97 | 90.2 |

All compounds tested showed cytotoxic activity against the cell lines tested. In most cases the compounds of the invention were more potent than the parent nucleoside against all cell lines.

Example 3—Assessment of Cytotoxicity and Cancer Stem Cell Activity

A further comparative analysis of the toxicity of compounds in the acute myeloid leukaemia (AML) cell line KG1a over an extended dose range was carried out, and the relative effect assessed of the compounds on the leukaemic stem cell (LSC) compartment within the KG1a cell line, across the entire dose range.

Materials and Methods

KG1a Cell Culture Conditions

The KG1a cell line was maintained in RPMI medium (Invitrogen, Paisley, UK) supplemented with 100 units/ml penicillin, 100 µg/ml streptomycin and 20% foetal calf serum. Cells were subsequently aliquoted ($10^5$ cells/100 µl) into 96-well plates and were incubated at 37° C. in a humidified 5% carbon dioxide atmosphere for 72h in the presence of nucleoside analogues and their respective pro-Tides at concentrations that were experimentally determined for each series of compounds. In addition, control cultures were carried out to which no drug was added. Cells were subsequently harvested by centrifugation and were analyzed by flow cytometry using the Annexin V assay.

Measurement of In Vitro Apoptosis

Cultured cells were harvested by centrifugation and then resuspended in 195 µl of calcium-rich buffer. Subsequently, 5 µl of Annexin V (Caltag Medsystems, Botolph Claydon, UK) was added to the cell suspension and cells were incubated in the dark for 10 mins prior to washing. Cells were finally resuspended in 190 µl of calcium-rich buffer together with 10 µl of propidium iodide. Apoptosis was assessed by dual-colour immunofluorescent flow cytometry as described previously. Subsequently LD$_{50}$ values (the dose required to kill 50% of the cells in a culture) were calculated for each nucleoside analogue and ProTide.

Immunophenotypic Identification of the Leukaemic Stem Cell Compartment

KG1a cells were cultured for 72h in the presence of a wide range of concentrations of each compound assayed. Cells were then harvested and labelled with a cocktail of anti-lineage antibodies (PE-cy7), anti-CD34 (FITC), anti-CD38 (PE) and anti-CD123 (PERCP cy5). The sub-population expressing a LSC phenotype were subsequently identified and were expressed as a percentage of all viable cells left in the culture. The percentages of stem cells remaining were then plotted on a dose-response graph and the effects of the compounds were compared with each other, and with the parent nucleoside.

Statistical Analysis

The data obtained in these experiments were evaluated using one way ANOVA. All data was confirmed as Gaussian or a Gaussian approximation using the omnibus K2 test. LD$_{50}$ values were calculated from the non-linear regression and line of best-fit analysis of the sigmoidal dose-response curves. All statistical analyses were performed using Graphpad Prism 6.0 software (Graphpad Software Inc., San Diego, Calif.).

Results

The in vitro drug sensitivity was measured using the Annexin V/propidium iodide assay.

Compound A showed increased in vitro potency when compared to Cordycepin (P<0.0001). 2-F-Cordycepin was significantly more potent than Cordycepin (P<0.0001) and all of the ProTides tested showed increased potency when compared to the parental nucleoside (FIG. 1).

Figure 2:
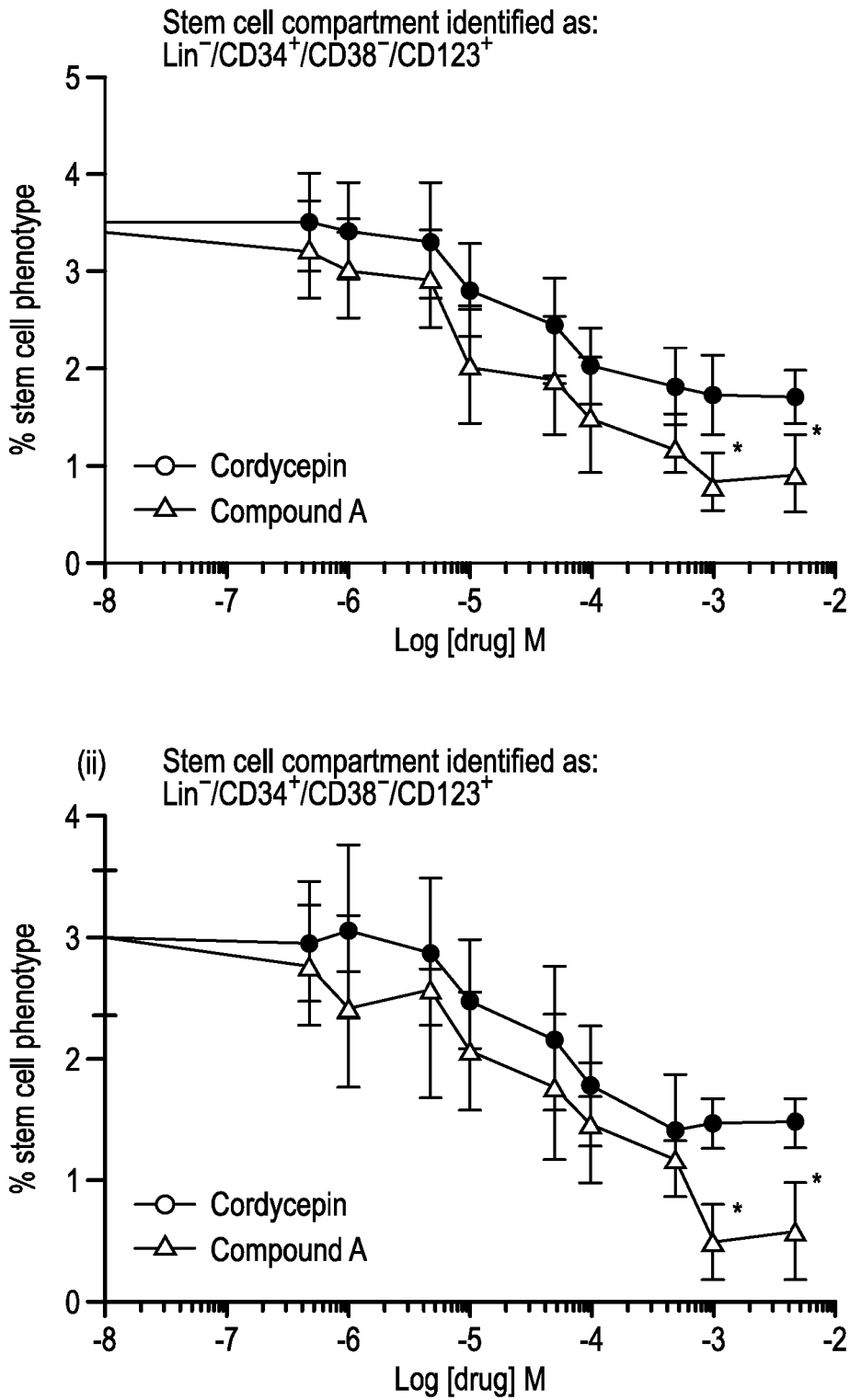
FIG. 2. Analysis of the leukaemic stem cell (LSC) targeting capacity of Cordycepin and Compound A. The previously generated data (ii) is shown for comparison. All data are the mean (±SD) of three independent experiments.

These experiments confirmed that compound A showed evidence of increased potency in the stem cell compartment at concentrations above 1 mM. As can be seen from FIG. 2, compound A demonstrated an ability not only to reduce cancer stem cell numbers in total, but also to reduce numbers of such cells as a proportion of the total of cancer cells present in culture. This indicates the ability of compound A to preferentially target cancer stem cells. At the higher concentrations tested (1 mM and above), the ability of compound A to preferentially target LSCs was significantly greater than that of the parent compound.

Figure 3:
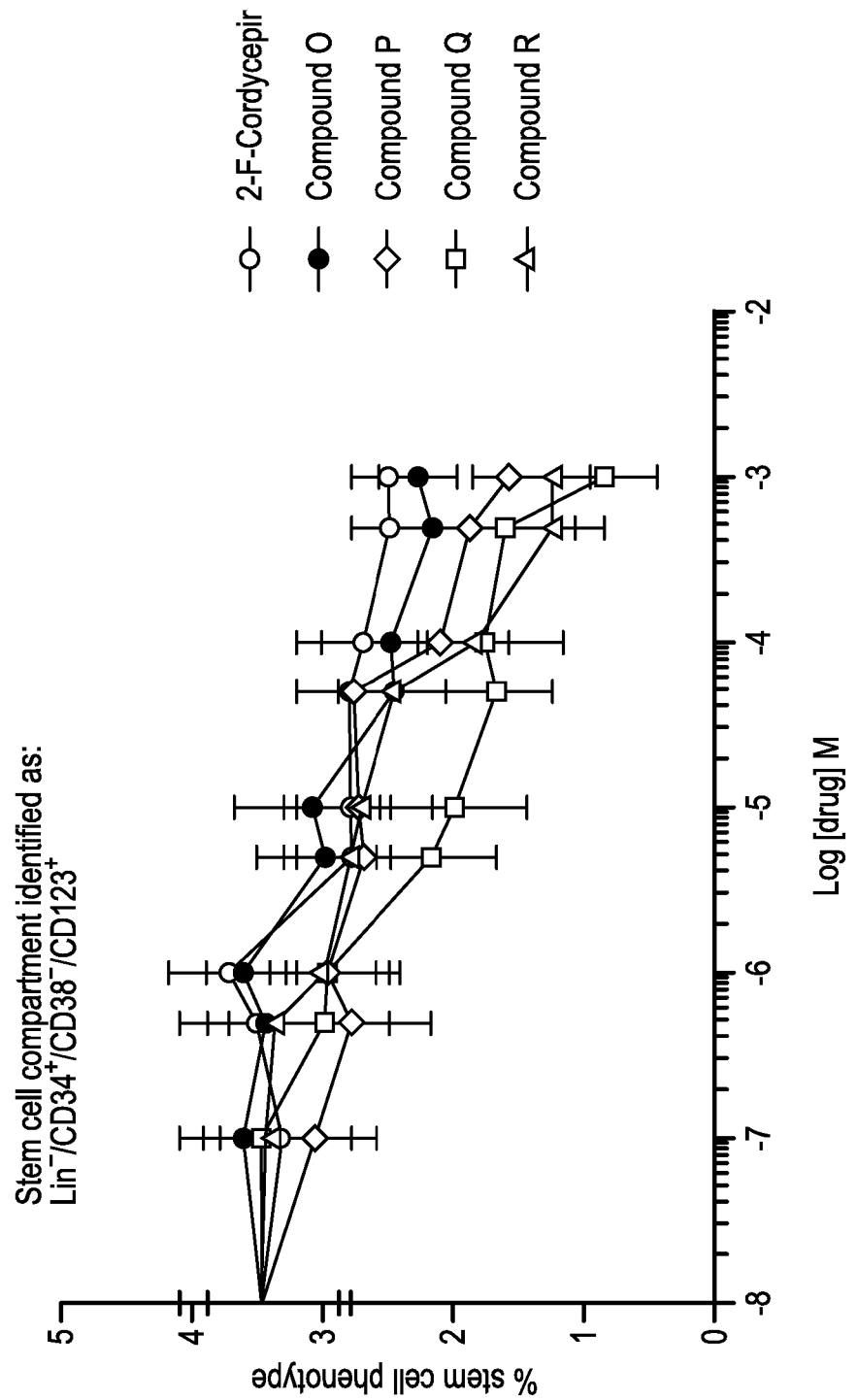
FIG. 3. Analysis of the LSC targeting capacity of 2-F-Cordycepin and Compounds O, P, Q and. All data are the mean (±SD) of three independent experiments.
Figure 4:
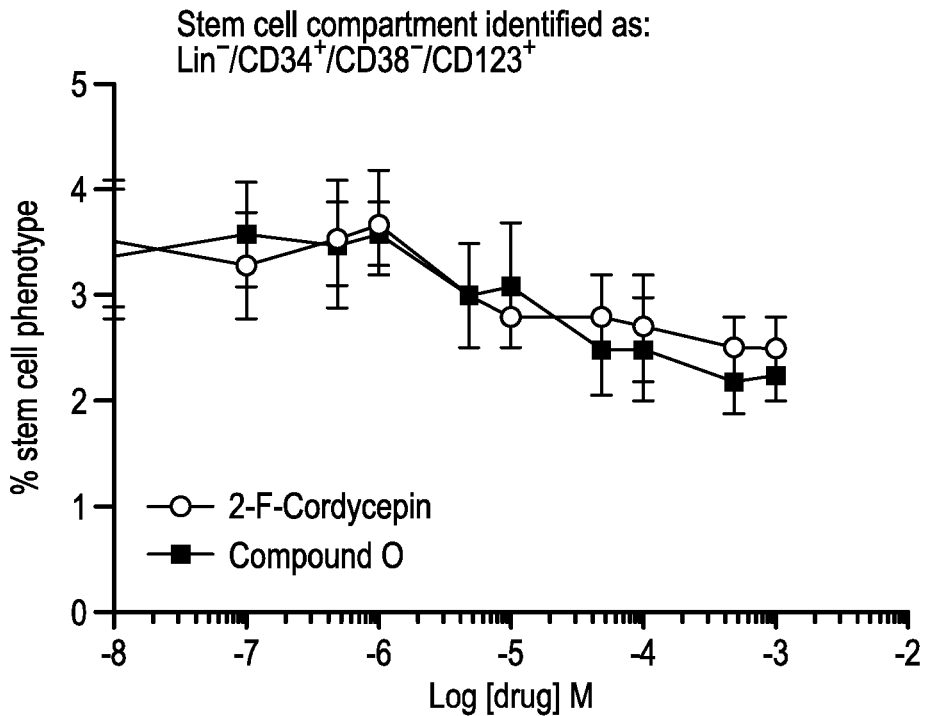
FIG. 4. Comparison of LSC targeting capacity of 2-F-Cordycepin and each proTide. All data are the mean (±SD) of three independent experiments.
Figure 4:
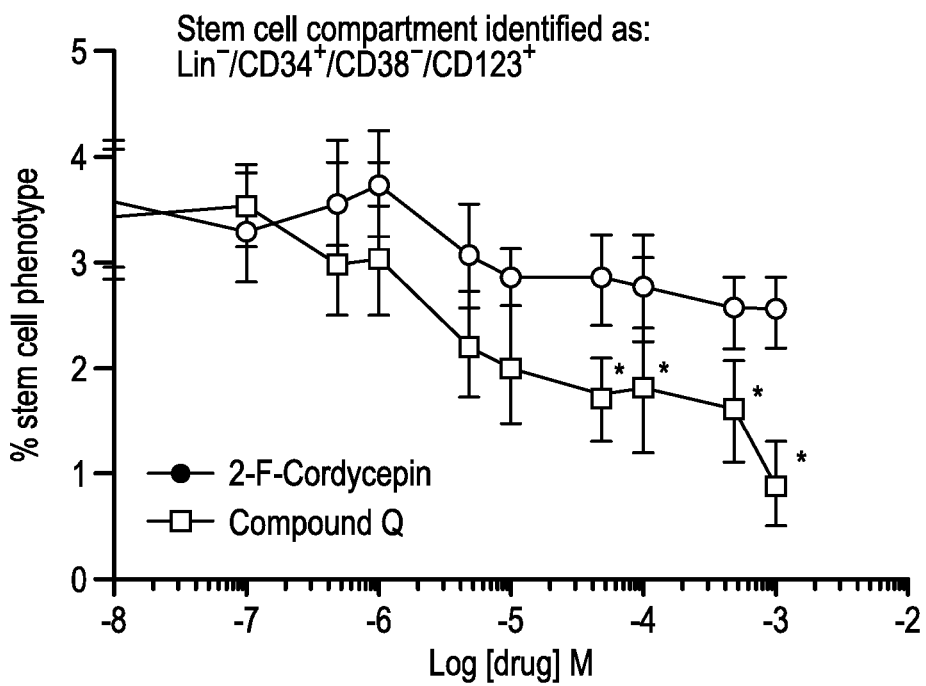
Figure 4:
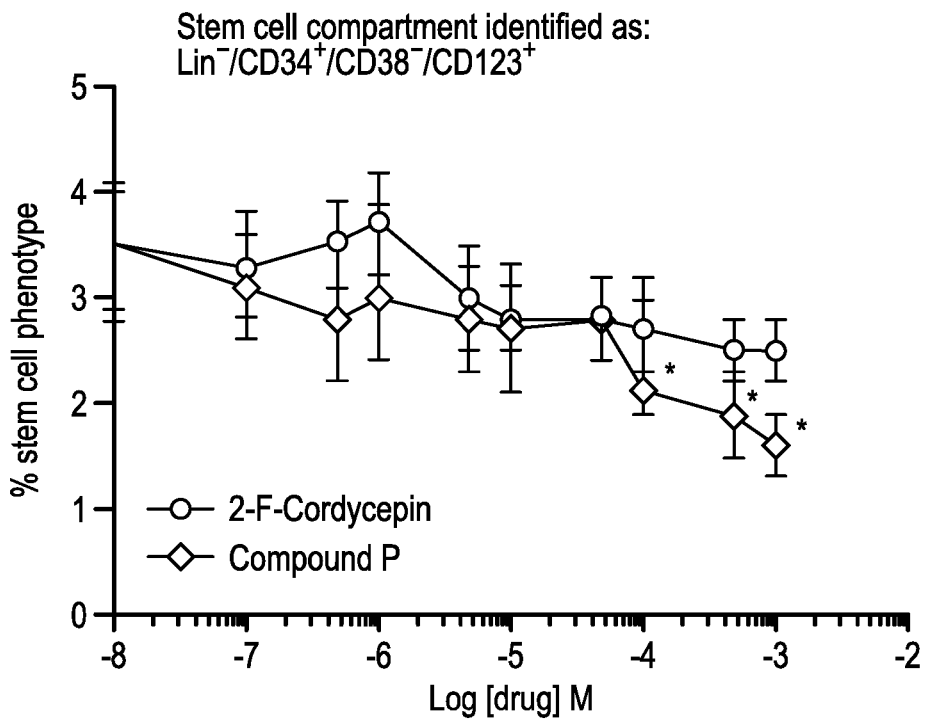
Figure 4:
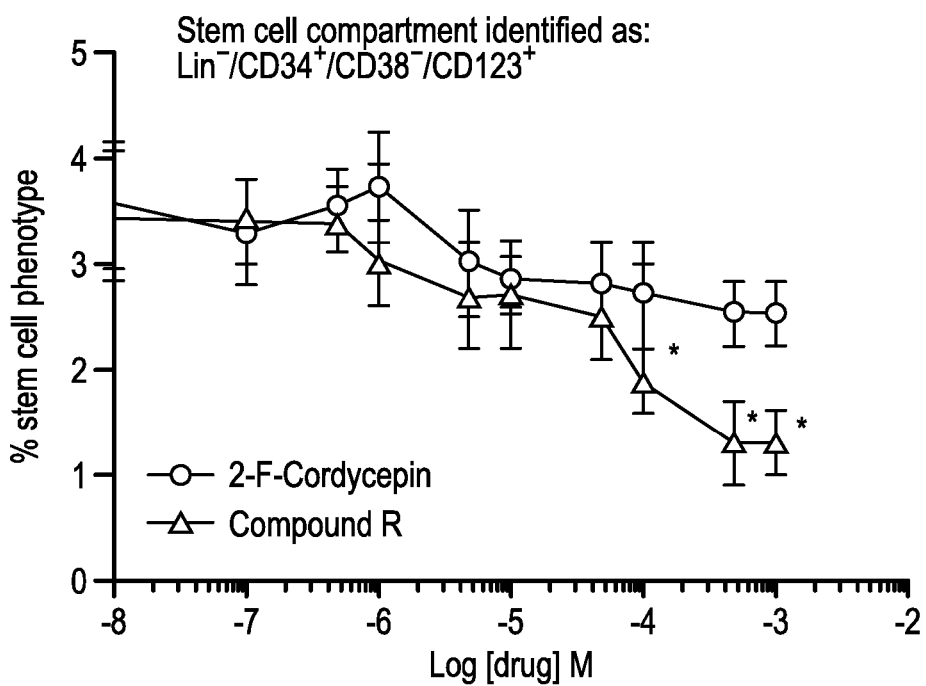

The 2-F-Cordycepin proTides compounds P, Q and R also showed preferential targeting of LSCs that was significantly improved when compared with the parental nucleoside. In contrast, while compound O was able to bring about a reduction in the proportion of LSCs present in treated cell populations (indicating an ability to target LSCs), its activity was not significantly different to 2-F-Cordycepin at any of the concentrations tested. FIG. 3 shows the comparison between 2-F-Cordycepin and all of the proTides tested, while individual comparisons are shown in the panels of FIG. 4.

Example 4—Further Cytotoxicity Assessment and Inhibition Studies

Certain compounds of the invention were subjected to further studies to test the cytotoxic activity of certain compounds of the invention and also to measure their activity against 4 haematological cancer cell lines
TdT positive CEM (Human ALL)
TdT negative K562 (Human CML)
TdT negative H1-60 (Human ANLL)
RL (CRL-2261) non-HD lymphoma The concentrations of the active metabolite dATP (Cordycepin triphosphate) in these cell lines was also measured.

The cytotoxic activity and the intracellular 3'-dATP concentrations were also studied in the presence of hENT1, Adenosine Kinase (AK) and Adenosine Deaminase pharmacological inhibitors in CEM and RL cancer cell lines. Said inhibitors that mimic known cancer resistance mechanisms.

Methods

Cell Culture

HL-60 (ATCC® CCL-240™), K562 (ATCC® CCL-243™), CCRF-CEM (ATCC® CRM-CCL-119™) and RL (ATCC® CRL-2261™) leukaemia cell lines, obtained from the American Type Culture Collection (ATCC), Middlesex. HL-60 and K562 cell lines are deoxynucleotidyl transferase-negative (TdT−ve), whereas CCRF-CEM cell line is TdT+ve.

HL-60 cell line is of acute promyelocytic leukaemia; K562 is a CML cell line, CCRF-CEM cell line is of acute lymphoblastic leukaemia (ALL); and RL is non-Hodgkin's lymphoma cell line.

Maintenance of Cell Lines

HL-60, K562, CCRF-CEM and RL cell lines were cultured in RPMI-1640 medium (Sigma Aldrich, UK), which were supplemented with 10% Fetal Bovine Serum (FBS) (PAA Laboratories), 1% amphotericin B (5.5 ml) and 1% penicillin/streptomycin (5.5 ml) (PAA Laboratories) and grown in flasks at 37° C. incubator with 5% $CO_2$.

Adenosine 5'-triphosphate (ATP) Assay

The amount of ATP was used as a measurement of cell number and cell viability. ATP ViaLight™ plus assay kit (Lonza, USA: Product No. LT07-121) to detect ATP in cells treated in luminescence compatible 96 well plates (initial concentration of cells was $1 \times 10^4$ cells/well) with cordycepin and ProTides at concentrations of: 0, 0.1, 0.5, 1, 5 and 10 μM, followed by incubation for 72 hours at 37° C. incubator with 5% $CO_2$. For inhibitor studies, 10 μM of NBTI or 1 μM EHNA or A-134974 was added and left for 5 minutes before adding the drugs (see section 5 for inhibitor details).

After incubation, 50 μl of cell lysis reagent was added to the 96 well plates to release the intracellular ATP, followed by 100 μl of ATP monitoring reagent (AMR). The luminescent values of each well were determined using FLUOstar OPTIMA microplate reader (BMG Labtech) which convert ATP into light by using luciferase enzyme. Therefore, the amount of luminescence produced was directly proportional to the amount of ATP.

Treating Cells and Extracting Samples for Intracellular Triphosphate Analysis

Cell lines with $5 \times 10^6$ cells/ml were used. Cells were treated with 1 μl of 50 μM of each of cordycepin and compounds A, B, D, E and F and incubated for 2 hours at 37° C. with 5% $CO_2$. After incubation, cells were centrifuged (ambient, 1200 rpm, 5 minutes), the culture medium supernatants were removed, and the cell pellets were washed with 1 ml of PBS and centrifuged (ambient, 1200 rpm, 5 minutes). The supernatants were removed; the pellets were reconstituted in 100 μl of PBS and 100 μl of 0.8M perchloric acid and vortex mixed and kept on ice for 30 minutes. Then centrifuged (ambient, 1200 rpm, 5 minutes) and 180 μl of the supernatant was transferred to new tubes and stored at −80° C. until time of analysis.

During analysis, 90 μl of the extract was transferred to the fresh tubes. 25 μl of 1M ammonium acetate was added to the extract, and then neutralised by addition of 10 μl of 10% ammonia and 5 μl of deionised water, then transferred to LC-MS vials and 10 μl was injected into the UPLC-MS/MS system.

Inhibitor Studies

Cell lines were treated in the same way as described above but before treatment with drugs, a number of inhibitors were added:
1) Nitrobenzylthioinosine (NBTI) (Sigma-Aldrich, St. Louis, Mo., product #N2255) blocks nucleoside transporters
2) EHNA hydrochloride (Sigma-Aldrich, St. Louis, Mo., product #E114) blocks adenosine deaminase
3) Adenosine kinase inhibitor A-134974 dihydrochloride hydrate (Sigma-Aldrich, St. Louis, Mo., product #A2846): blocks adenosine kinase Cells were treated with 10 μM of NBTI or 1 μM EHNA or A-134974 and left for 5 minutes before adding the drug. The cells were then incubated for 2 hours at 37° C. with 5% $CO_2$.

LC-MS/MS Analysis

The analytes were resolved using an ultra-performance liquid chromatography system (Accela UPLC, Thermo Scientific, UK) equipped with a Biobasic Ax5 μm, 50×2.1 mm column (Thermo Electron Corporation, Murrieta, Calif., USA) and mobile phase consisting of a mixture of 10 mM NH4Ac in ACN/$H_2O$ (30:70 v/v), pH6.0 (A), and 1 mM NH4Ac in ACN/$H_2O$ (30:70 v/v), pH10.5 (B). The mobile phase gradient will be employed, comprising: buffer A=95% at 0-0.5 min, from 95 to 0% over 1.25 minutes, held at 0% for 1.75 minutes, from 0-95% over 0.1 min, ending with 95% for 2.9 minutes, all at a flow rate of 500 μl/min.

Eluting compounds of interest were detected using a triple stage quadrupole Vantage mass spectrometry system (Thermo Scientific, UK) equipped with an electrospray ion source. Samples were analysed in the Multiple Reaction Monitoring, negative ion modes at a spray voltage of 3000V. Nitrogen was used as sheath and auxiliary gas at a flow rate of 50 and 20 arbitrary units, respectively. Argon was used as collision gas with pressure of 1.5 mTorr. The optimum transitional daughter ions mass and collision energy of each analyst was as follows: 3' ATP 490.1→392.1 (collision energy 19V) and the internal standard ChloroATP 539.9→442.2 (collision energy 24V).

Statistical Analysis

The dose-response curves of cytotoxicity of the drugs was determined using non-linear regression analysis of percentage cell viability versus concentration and $EC_{50}$ values were obtained. The intracellular assay was conducted in five replicates for each condition. Intracellular assay was determined using paired t test (two-tailed) analysis of 3' ATP/ATP concentration and p-values were obtained. For all the analysis, Prism Software program (GraphPad Software) was used and Microsoft Powerpoint® 2013 was used to plot the results.

Results

Summary $IC_{50}$ Table (µM)

|  | Cordycepin | A (FD) | B (FD) | D (FD) | E (FD) | F (FD) |
|---|---|---|---|---|---|---|
| CEM (TdT$^{+ve}$) | 19.5 | 0.87 (22) | 0.13 (150) | 6.1 (3) | 10.0 (2) | 4.3 (5) |
| K562 | 10.9 | 2.4 (5) | 0.21 (52) | 4.2 (3) | 13.9 (1) | 6.3 (2) |
| HL-60 | 11.4 | 4.6 (3) | 2.6 (4) | 5.4 (2) | 10.2 (1) | 8.3 (1) |
| CRL | 24.5 | 2.1 (12) | 0.4 (61) | 4.8 (5) | 11.0 (2) | 3.4 (7) |

(FD) = fold difference compared to Cordycepin = Cordycepin $IC_{50}$/ProTide $IC_{50}$ Summary Mean Intracellular 3'-dATP levels (µg/ml)

|  | Cordycepin | A (FD) | B (FD) | D (FD) | E (FD) | F (FD) |
|---|---|---|---|---|---|---|
| CEM | 0.2 | 3.7 (19) | 11.5 (58) | 2.9 (15) | 0.2 (1) | 1.1 (6) |
| K562 | 1.7 | 2.6 (13) | 6.2 (4) | 0.9 (0.5) | 0.2 (0.1) | 1.3 (0.8) |
| HL-60 | 1.7 | 3.2 (16) | 5.1 (3) | 0.7 (0.4) | 0.2 (0.1) | 1.2 (0.7) |
| CRL | 0.8 | 6.6 (33) | 10.8 (14) | 1.7 (2) | 1 (1) | 3.4 (4) |

(FD) = fold difference compared to Cordycepin = Protide Intracellular TP/Cordycepin Intracellular TP Compounds A and B were the best performers with $IC_{50}$ from 3 to 150-fold better than cordycepin Compounds A and B produced intracellular 3'-dATP concentrations 3 to 56-fold better than cordycepin.

Summary $IC_{50}$ Table (All in µM)

|  |  | CEM (FD) | CRL (FD) |
|---|---|---|---|
| Cordycepin | Control | 11.5 | 7.3 |
|  | NBTI | 57.7 (5) | 17.9 (2) |
|  | EHNA | 0.7 (−16) | 13.2 (2) |
|  | AK | 29.2 (3) | 28.6 (4) |
| A | Control | 1.4 | 3.6 |
|  | NBTI | 2.0 (1) | 2.6 (1) |
|  | EHNA | 3.1 (2.2) | 2.9 (1) |
|  | AK | 3.6 (3) | 10.2 (3) |
| B | Control | 0.9 | 3.1 |
|  | NBTI | 1.4 (1) | 2.6 (1) |
|  | EHNA | 1.3 (1) | 5.2 (2) |
|  | AK | 1.3 (1) | 2.8 (1) |
| E | Control | 9.9 | 8.2 |
|  | NBTI | 17.1 (2) | 8.2 (1) |
|  | EHNA | 13.4 (1) | 5.9 (1) |
|  | AK | 10.3 (1) | 7.1 (1) |

(FD) = fold difference compared to control

Summary Mean Intracellular 3'-dATP levels (µg/ml)

|  |  | CEM (FD) | CRL (FD) |
|---|---|---|---|
| Cordycepin | Control | 0.24 | 0.10 |
|  | NBTI | 0.14 (1) | 0.06 (1) |
|  | EHNA | 9.01 (38) | 1.85 (19) |
|  | AK | 0.31 (1) | 0.16 (1) |
| A | Control | 1.30 | 0.31 |
|  | NBTI | 0.99 (1) | 0.32 (1) |
|  | EHNA | 135 (1) | 0.27 (1) |
|  | AK | 1.20 (1) | 0.30 (1) |
| B | Control | 4.07 | 0.59 |
|  | NBTI | 3.14 (1) | 0.68 (1) |
|  | EHNA | 3.62 (1) | 0.67 (1) |
|  | AK | 2.99 (1) | 0.77 (1) |
| E | Control | 0.32 | 0.08 |
|  | NBTI | 0.17 (1) | 0.12 (1) |
|  | EHNA | 0.21 (1) | 0.07 (1) |
|  | AK | 0.19 (1) | 0.06 (1) |

(FD) = fold difference compared to control

NBTI, AK and EHNA did not affect the intracellular 3'-dATP generated by the three compounds of the invention tested indicating that these inhibitors do not interfere with the metabolism by which the compounds of the invention generate the active agent 3'-dATP within the hematological cancer cell lines used in this study. As these inhibitors mimic known cancer resistance mechanisms, these results indicate that the compounds of the invention will be less susceptible to cancer resistance mechanisms that cordycepin.

The invention claimed is:
1. A compound of formula (Ib):

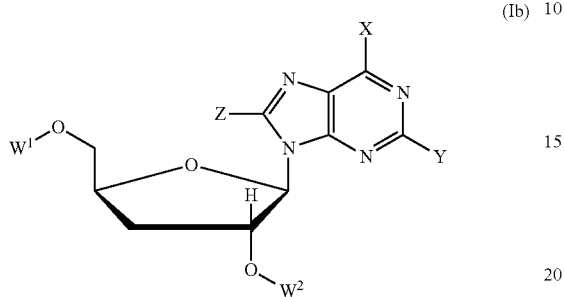

wherein:
$W_1$ and $W_2$ are each independently selected from the group consisting of —P(=O)(U)(V) and H, with the proviso that at least one of $W_1$ and $W_2$ is —P(=O)(U)(V),
where U and V, independently for each of $W_1$ and $W_2$, are selected from the group consisting of:
(a) U is —OAr and V is —NR$_4$—CR$_1$R$_2$—C(=O)OR$_3$,
where Ar is selected from the group consisting of $C_{6-30}$aryl and 5-30-membered heteroaryl, each of which is optionally substituted with one, two, or three substituents selected from halo, $C_1$-$C_4$-alkyl, $C_1$-$C_4$-alkoxy, nitro and cyano;
each of $R_1$ and $R_2$ is independently selected from H, and the group consisting of $C_{1-20}$alkyl, $C_6$aryl $C_{1-6}$alkyl, $C_{2-20}$alkenyl, $C_{1-20}$alkoxy, $C_{1-20}$alkoxyC$_{1-20}$alkyl, $C_{1-20}$alkoxyC$_6$aryl, $C_{2-20}$alkynyl, $C_{3-20}$cycloalkyl, $C_{6-30}$aryl, $C_{6-30}$aryloxy and 5-20-membered heterocyclyl;
$R_3$ is selected from H, and the group consisting of straight, branched, or cyclic butyl, pentyl, hexyl, octyl, nonyl, and dodecyl groups, $C_{6-30}$aryl $C_{1-20}$alkyl, $C_{2-20}$alkenyl, $C_{1-20}$alkoxyC$_{1-20}$alkyl, $C_{1-20}$alkoxyC$_{6-30}$aryl, $C_{2-20}$alkynyl, $C_{3-20}$cycloalkyl, $C_{6-30}$aryl, and 5-20-membered heterocyclyl;
$R_4$ is selected from H, and the group consisting of $C_{1-20}$alkyl, $C_{6-30}$arylC$_{1-20}$alkyl, $C_{2-20}$alkenyl, $C_{1-20}$alkoxy, $C_{1-20}$alkoxyC$_{1-20}$alkyl, $C_{1-20}$alkoxyC$_{6-30}$aryl, $C_{2-20}$alkynyl, $C_{3-20}$cycloalkyl, $C_{6-30}$aryl, $C_{6-30}$aryloxy and 5-20-membered heterocyclyl;
and
(b) each of U and V is selected independently from —NR$_5$R$_6$,
where $R_5$ is selected from the group consisting of H and $C_{1-6}$alkyl and $R_6$ is —CR$_7$R$_8$CO$_2$R$_9$, where $R_7$ and $R_8$ are selected independently from the group consisting of the side chains, including H, of naturally occurring alpha amino acids and $R_9$ is selected from H, and the group consisting of $C_{1-20}$alkyl, $C_{6-30}$arylC$_{1-20}$alkyl-, $C_{2-20}$alkenyl, $C_{1-20}$alkoxyC$_{1-20}$alkyl, $C_{1-20}$alkoxyC$_{6-30}$aryl, $C_{2-20}$alkynyl, $C_{3-20}$cycloalkyl, $C_{6-30}$aryl, and 5-20-membered heterocyclyl; or
$R_5$ and $R_6$ together with the N atom to which they are attached form a ring moiety comprising 5 to 8 ring atoms;
X is selected from the group consisting of: NR$_{12}$R$_{13}$, where each of $R_{12}$ and $R_{13}$ is independently selected from the group consisting of H and $C_{1-6}$alkyl; and —SR$_{14}$ where $R_{14}$ is selected from the group consisting of H and $C_{1-6}$alkyl;
Z is independently selected from the group consisting of H, OH, F, Cl, Br, I, $C_{1-6}$alkyl, —NR$_{12}$R$_{13}$, and —SR$_{14}$ where $R_{14}$ is selected from the group consisting of H and $C_{1-6}$alkyl; and
Y is selected from the group consisting of H, OH, F, Cl, Br, I, —OC$_{1-6}$alkyl, $C_{1-6}$alkyl, $C_{2-8}$alkynyl, —NR$_{15}$R$_{16}$ where each of $R_{15}$ and $R_{16}$ is independently selected from H and $C_{1-6}$alkyl, and —SR$_{17}$ where $R_{17}$ is selected from the group consisting of H and $C_{1-6}$alkyl,
or a pharmaceutically acceptable salt of the compound of formula (Ib).

2. The compound of claim 1, wherein the compound is represented by formula (II):

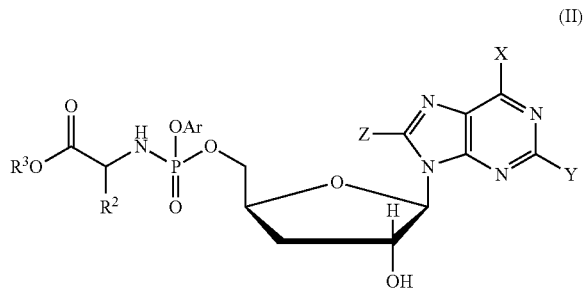

wherein X is —NR$_{12}$R$_{13}$.

3. The compound according to claim 1, wherein Ar is selected from the group consisting of phenyl and napthyl.

4. The compound according to claim 3, wherein Ar is unsubstituted.

5. The compound according to claim 3, wherein Ar is substituted with one, two, or three substituents selected from the group consisting of: halo, $C_1$-$C_4$-alkyl, $C_1$-$C_4$-alkoxy, nitro and cyano.

6. The compound according to claim 1, wherein $R^2$ is $C_1$-$C_4$-alkyl.

7. The compound according to claim 6, wherein $R^2$ is methyl.

8. The compound according to claim 7, wherein the C atom bearing $R_1$ and $R_2$ has the same absolute configuration as of L-alanine.

9. The compound according to claim 1, wherein $R_3$ is selected from the group consisting of benzyl and straight, branched, or cyclic butyl, pentyl, hexyl, octyl, nonyl, and dodecyl groups.

10. The compound according to claim 9, wherein $R_3$ is selected from the group consisting of benzyl and n-pentyl.

11. The compound according to claim 10, wherein R₃ is benzyl.

12. The compound according to claim 1, wherein X is NH₂.

13. The compound according to claim 1, wherein Y is H.

14. The compound according to claim 1, wherein Z is H.

15. The compound according to claim 1, wherein Z is F.

16. The compound according to claim 1, wherein Z is Cl.

17. The compound according to claim 1, wherein Z is OMe.

18. The compound of claim 1, wherein the compound is selected from the group consisting of:
- (2S)-Benzyl 2-(((((2S,4R,5R)-5-(6-amino-9H-purin-9-yl)-4-hydroxytetrahydrofuran-2-yl)methoxy)(naphthalen-1-yloxy)phosphoryl)amino)propanoate;
- Benzyl 2-(((((2S,4R,5R)-5-(6-amino-9H-purin-9-yl)-4-hydroxytetrahydrofuran-2-yl)methoxy)(phenoxy)phosphoryl)amino)acetate;
- (2S)-Pentyl 2-(((((2S,4R,5R)-5-(6-amino-9H-purin-9-yl)-4-hydroxytetrahydrofuran-2-yl)methoxy)(naphthalen-1-yloxy)phosphoryl)amino)-4-methylpentanoate;
- (2S)-Benzyl 2-(((((2S,4R,5R)-5-(6-amino-9H-purin-9-yl)-4-hydroxytetrahydrofuran-2-yl)methoxy)(2-(3-ethoxy-3-oxopropyl)phenoxy)phosphoryl)amino)propanoate;
- (2S)-Benzyl 2-(((((2R,3R,5S)-2-(6-amino-9H-purin-9-yl)-5-(hydroxymethyl)tetrahydrofuran-3-yl)oxy)(phenoxy)phosphoryl)amino)propanoate;
- Benzyl 2-(((((2S,4R,5R)-5-(6-amino-9H-purin-9-yl)-4-(((1-(benzyloxy)-1-oxopropan-2-yl)amino)(phenoxy)phosphoryl)oxy)tetrahydrofuran-2-yl)methoxy)(phenoxy)phosphoryl)amino)propanoate;
- (2S)-Benzyl 2-(((((2R,3R,5S)-2-(6-amino-9H-purin-9-yl)-5-(hydroxymethyl)tetrahydrofuran-3-yl)oxy)(naphthalen-1-yloxy)phophoryl)amino)proponate;
- Benzyl 2-[({[5-(6-amino-9H-purin-9-yl)-4-hydroxyoxolan-2-yl]methoxy}({[1-(benzyloxy)-1-oxopropan-2-yl]amino})phosphoryl)amino]propanoate;
- (2S)-Benzyl 2-((((2S,4R,5R)-5-(6-amino-2-methoxy-9H-purin-9-yl)-4-hydroxytetrahydrofuran-2-yl)methoxy)(naphthalen-1-yloxy)phosphorylamino)propanoate;
- (2S)-Benzyl 2-((((2S,4R,5R)-5-(6-amino-2-methoxy-9H-purin-9-yl)-4-hydroxytetrahydrofuran-2-yl)methoxy)(phenoxy)phosphorylamino)propanoate;
- (2S)-Benzyl 2-(((((2S,4R,5R)-5-(6-amino-2-fluoro-9H-purin-9-yl)-4-hydroxytetrahydrofuran-2-yl)methoxy)(phenoxy)phosphoryl)amino)propanoate;
- (2S)-Hexyl 2-(((((2S,4R,5R)-5-(6-amino-2-fluoro-9H-purin-9-yl)-4-hydroxytetrahydrofuran-2-yl)methoxy)(phenoxy)phosphoryl)amino)propanoate;
- (2R)-Benzyl 2-((((2S,4R,5R)-5-(6-amino-2-chloro-9H-purin-9-yl)-4-hydroxytetrahydrofuran-2-yl)methoxy)(naphthalen-1-yloxy)phosphorylamino)propanoate;
- 2-O-Methyl-3'-deoxyadenosine-5'-O-[1-naphthyl(1-pentyloxy-L-leucinyl)] phosphate;
- 2-O-Methyl-3'-deoxyadenosine-5'-O-[phenyl(1-hexyloxy-L-alaninyl)] phosphate;
- 2-Fluoro-3'-deoxyadenosine-5'-O-[1-naphthyl(benzyloxy-L-alaninyl)] phosphate;
- 2-Fluoro-3'-deoxyadenosine-5'-O-[1-naphthyl(1-pentyloxy-L-leucinyl)] phosphate;
- 2-Chloro-3'deoxyadenosine 5'-O-[1-phenyl (2,2-dimethylpropoxy-L-alanine)] phosphate; and
- 2-Chloro-3'deoxyadenosine 5'-O-[1-naphtyl (2,2-dimethylpropoxy-L-alanine)] phosphate.

19. A pharmaceutical composition, comprising a compound according to claim 1; and a pharmaceutically acceptable excipient.

* * * * *